US008709435B2

(12) United States Patent
Campana et al.

(10) Patent No.: US 8,709,435 B2
(45) Date of Patent: *Apr. 29, 2014

(54) HYPALLERGENIC MOSAIC ANTIGENS AND METHODS OF MAKING SAME

(75) Inventors: Raffaela Campana, Vienna (AT); Rudolf Valenta, Theresienfeld (AT); Susanne Vrtala, Vienna (AT); Ines Swoboda, Vienna (AT); Margarete Focke-Tejkl, Vienna (AT); Anna Gieras, Vienna (AT); Susanne Spitzauer, Vienna (AT); Peter Valent, Vienna (AT); Katharina Blatt, Grossenzersdorf (AT); Birgit Linhart, Weissenkirchen (AT); Dietrich Kraft, Vienna (AT)

(73) Assignee: Biomay AG, Vienna (AT)

( * ) Notice: Subject to any disclaimer, the term of this patent is extended or adjusted under 35 U.S.C. 154(b) by 0 days.

This patent is subject to a terminal disclaimer.

(21) Appl. No.: 13/179,116

(22) Filed: Jul. 8, 2011

(65) Prior Publication Data

US 2012/0009210 A1 Jan. 12, 2012

Related U.S. Application Data

(60) Continuation-in-part of application No. 12/349,614, filed on Jan. 7, 2009, now abandoned, which is a division of application No. 10/542,735, filed as application No. PCT/EP03/14507 on Dec. 18, 2003, now Pat. No. 7,491,396.

(30) Foreign Application Priority Data

Jan. 21, 2003 (EP) .................................... 03001242

(51) Int. Cl.
*A61K 38/00* (2006.01)
*A61K 39/00* (2006.01)
*A61K 39/35* (2006.01)
*A61K 39/36* (2006.01)

(52) U.S. Cl.
USPC ...................... 424/185.1; 424/275.1; 514/1.1

(58) Field of Classification Search
None
See application file for complete search history.

(56) References Cited

U.S. PATENT DOCUMENTS

| 5,547,669 | A | 8/1996 | Rogers et al. |
| 5,605,793 | A | 2/1997 | Stemmer et al. |
| 5,811,238 | A | 9/1998 | Stemmer et al. |
| 5,830,721 | A | 11/1998 | Stemmer et al. |
| 6,489,145 | B1 | 12/2002 | Short |
| 7,491,396 | B2 | 2/2009 | Mothes et al. |
| 2008/0286311 | A1 | 11/2008 | Westritschnig et al. |
| 2009/0098167 | A1 | 4/2009 | Ball et al. |

FOREIGN PATENT DOCUMENTS

| EP | 1 221 317 | 7/2002 |
| EP | 1 817 330 | 12/2008 |
| WO | WO 94/23035 | 3/1994 |
| WO | WO 2007/124526 | 11/2007 |

OTHER PUBLICATIONS

Hartl et al. 'DNA vaccines for allergy treatment.' Methods 32:328-339, 2004.*
Gafvelin, G. et al., *J. Biol. Chem.*, Feb. 2007, vol. 282(6): 3778-3787.
Wallner, M. et al., *J Allergy Clin. Immunol.*, Aug. 2007, vol. 120(2): 374-380.
Akdis, C. et al., *Int. Arch. Allergy Immunol*, 2000, vol. 121(4): 261-269.
Ansari, A. et al., *J. Biol. Chem.*, 1989, vol. 264(19): 11181-11185.
Ball, T et al., *Allergy*, 2009, vol. 64: 569-580.
Blumenthal et al., "Definition of an Allergen/Allergens and Allergen Immunotherapy", Ed. R. Lockey et al., New York, Marcel Decker, 2004, pp. 37-50.
Campana, R. et al., *J. Allergy Clin. Immunol.*, Nov. 2010, vol. 126 (5): 1024-1031.
De Marino, S. et al., *Structure*, Aug. 1999, vol. 7(8): 943-952.
Dolecek, C. et al., *FEBS Letters*, vol. 335(3), 1993, p. 299-304.
Ferreira, F. et al., *Int. Arch. Allergy Immunol.*, Jul. 2002, vol. 128(3): 171-178.
Focke, M. et al., *FASEB*, vol. 19(11), Sep. 2001, vol. 19(11): 2042-2044.
Friedhoff, L. et al., *J. Allergy Clin. Immunol.*, Jul. 1986, vol. 78(8): 1190-1201.
Kuby et al., *Immunology*, Fourth edition, Chapter 18: Vaccines, 2000, p. 449-465.
Mothes-Luksch et al., *J. Immunol.*, 2008, vol. 181(7): 4864-4873.
Rogers et al., *Mol. Immunol.*, 1994, vol. 31(13): 955-966.
Schramm, G. et al., *J. Immunol.*, Feb. 1999, vol. 162(4): 2406-2414.
Valenta, R. et al., *Immunol. Reviews*, Feb. 2001, vol. 179: 119-127.
Valenta, R. et al., *Joint Congress of the British Society for Immunology and the Biochem. Society*, Dec. 10, 1996 (abstract only).
van Hage-Hamsten, M. et al., *J. Allergy Clin. Immunol.*, Nov. 1999, vol. 104(5): 969-977.
Vratala, S. et al., *J. Clin. Investigation*, 1997, vol. 99(7): 1673-1681.

* cited by examiner

*Primary Examiner* — Nora Rooney
(74) *Attorney, Agent, or Firm* — Chalin Smith; Smith Patent

(57) ABSTRACT

Hypoallergenic mosaic antigens assembled from naturally-occurring allergens are disclosed herein. Also disclosed are methods of making such hypoallergenic mosaic antigens, particularly those derived from plant allergens such as timothy grass pollen (Phl p 1 and Phl p 2) and birch pollen (Bet v 1). In a particularly preferred embodiment, the method of making the hypoallergenic mosaic antigen involves the steps of (a) cleaving a naturally-occurring allergen into at least two, preferably at least three non-overlapping peptide fragments and (b) recombining the peptide fragments such that the mosaic antigen includes all or substantially all of the amino acids of the original naturally-occurring allergen, though in a different order.

16 Claims, 22 Drawing Sheets

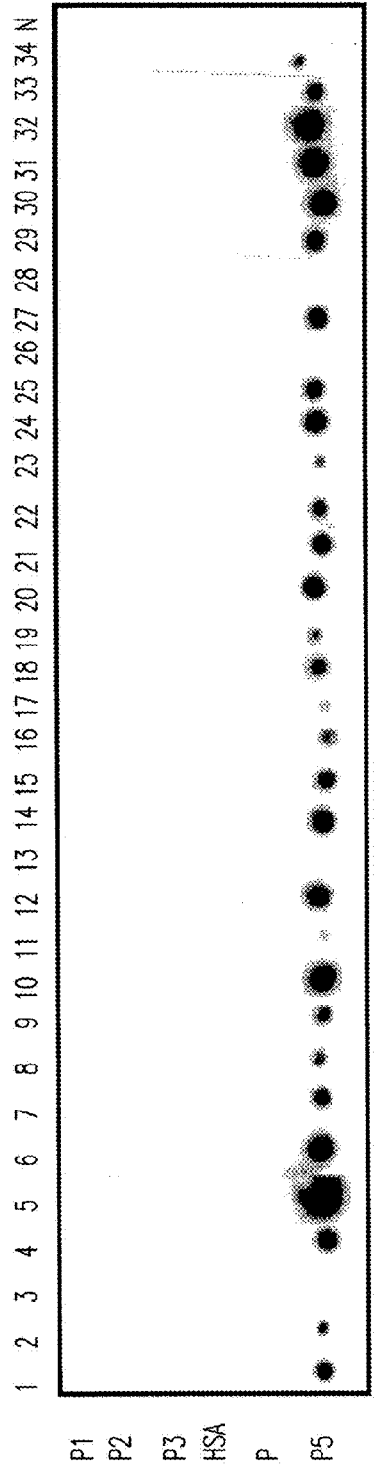 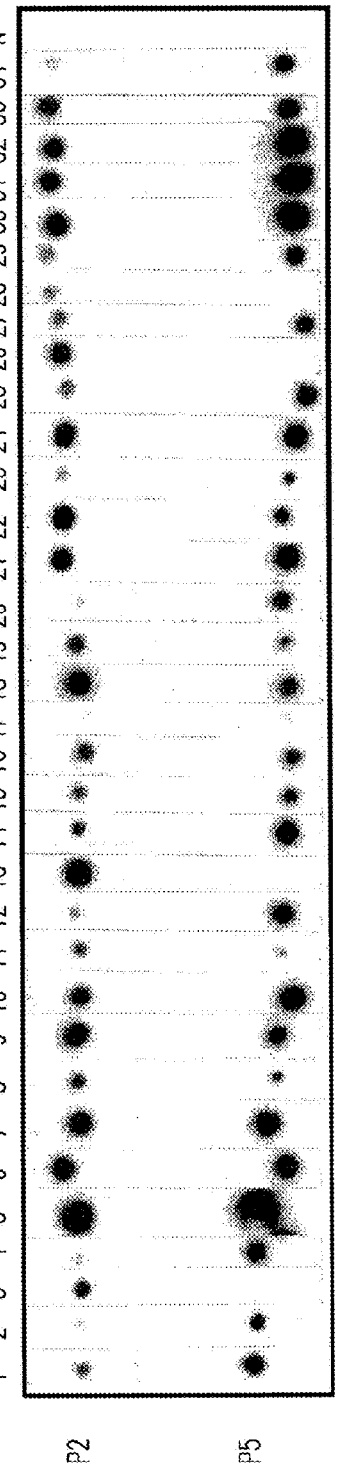

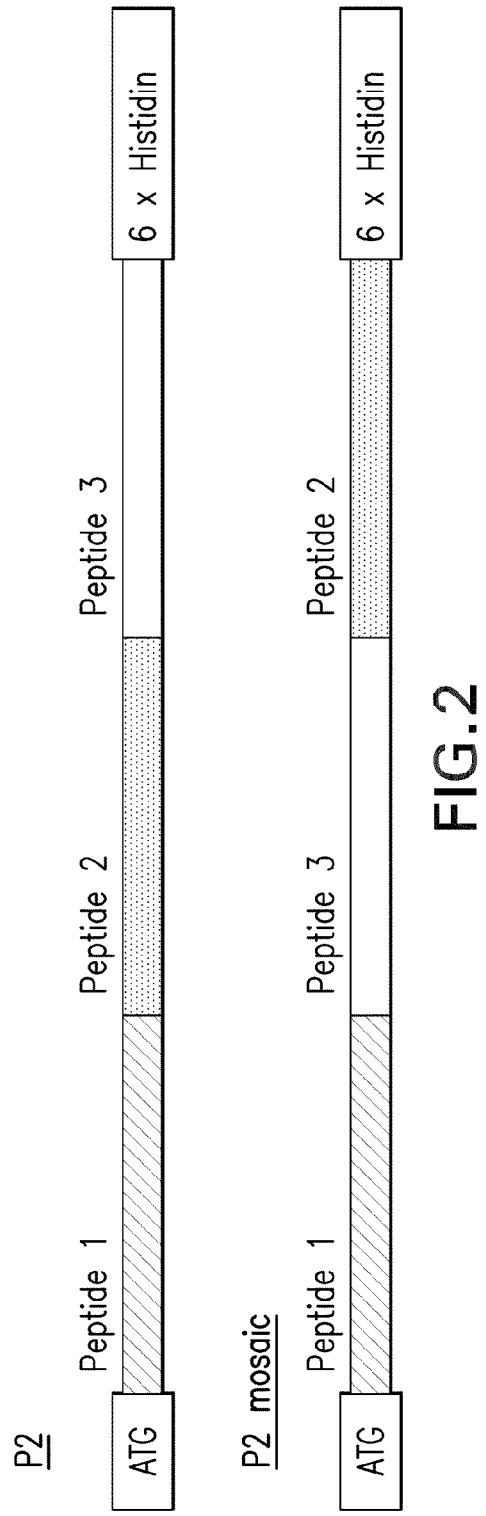

P2/1: 5'- GGA TTT CCA TAT GGT CCC GAA GGT GAC GTT CAC G - 3'  SEQ ID NO: 6
P2/2: 5'- GGT GAG GAA CCG GAA GAG CTC CAC CTC CGC CAT GGT - 3'  SEQ ID NO: 7
P2/3: 5'- GCG GAG GTG GAG CTC TTC CGG TTC CTC ACC GAG AAG - 3'  SEQ ID NO: 8
P2/4: 5'- GGA GCC GTG CTC CCG CTC TTC TGG CGC GTA GGT GGC - 3'  SEQ ID NO: 9
P2/5: 5'- TAC GCG CCA GAA GAG CGG GAG CAC GGC TCC GAG GAG - 3'  SEQ ID NO: 10
P2/6: 5'- CGC GAA TTC TCA GTG GTG GTG GTG GTT GAA GGG CCC CTG GAG CGG - 3'  SEQ ID NO: 11

P2M-Sequence

| | | | | | | | | | | | | | | | | | |
|---|---|---|---|---|---|---|---|---|---|---|---|---|---|---|---|---|---|
| ATG | GTC | CCG | AAG | GTC | ACG | TTC | ACG | GTG | GAG | AAG | GGG | TCC | AAC | GAG | AAG | CAC | SEQ ID NO:1 51 |
| M | V | P | K | V | T | F | T | V | E | K | G | S | N | E | K | H | SEQ ID NO:2 17 |

| | | | | | | | | | | | | | | | | | |
|---|---|---|---|---|---|---|---|---|---|---|---|---|---|---|---|---|---|
| CTG | GCG | GTG | CTG | GTG | AAG | TAC | GAG | GGG | GAC | ACC | ATG | GCG | GAG | GTG | GAG | CTC | SEQ ID NO:1 102 |
| L | A | V | L | V | K | Y | E | G | D | T | M | A | E | V | E | L | SEQ ID NO:2 34 |

| | | | | | | | | | | | | | | | | | |
|---|---|---|---|---|---|---|---|---|---|---|---|---|---|---|---|---|---|
| TTC | CGG | TTC | CTC | ACC | GAG | AAG | GGC | ATG | AAG | AAC | GTC | TTC | GAC | GTC | GTC | | SEQ ID NO:1 153 |
| F | R | F | L | T | E | K | G | M | K | N | V | F | D | D | V | V | SEQ ID NO:2 51 |

| | | | | | | | | | | | | | | | | | |
|---|---|---|---|---|---|---|---|---|---|---|---|---|---|---|---|---|---|
| CCA | GAG | AAG | TAC | ACC | ATT | GGG | GCC | ACC | TAC | GCG | CCA | GAA | GAG | CGG | GAG | CAC | SEQ ID NO:1 204 |
| P | E | K | Y | T | I | G | A | T | Y | A | P | E | E | R | E | H | SEQ ID NO:2 68 |

| | | | | | | | | | | | | | | | | | |
|---|---|---|---|---|---|---|---|---|---|---|---|---|---|---|---|---|---|
| GGC | TCC | GAC | GAG | TGG | GTC | GCC | ATG | ACC | AAG | GGG | GAG | GGC | GTG | TGG | ACG | | SEQ ID NO:1 255 |
| G | S | D | E | W | V | A | M | T | K | G | E | G | V | W | T | | SEQ ID NO:2 85 |

| | | | | | | | | | | | | | | | | | |
|---|---|---|---|---|---|---|---|---|---|---|---|---|---|---|---|---|---|
| TTC | GAC | AGC | GAG | GAG | CCG | CTC | CAG | GGG | CCC | TTC | AAC | CAC | CAC | CAC | CAC | | SEQ ID NO:1 306 |
| F | D | S | E | E | P | L | Q | G | P | F | N | H | H | H | H | | SEQ ID NO:2 102 |

| | |
|---|---|
| CAC | SEQ ID NO:1 309 |
| H | SEQ ID NO:2 103 |

FIG.4 rBet v 1
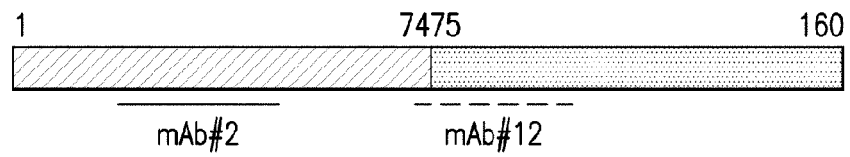
Bet v 1- rs 1
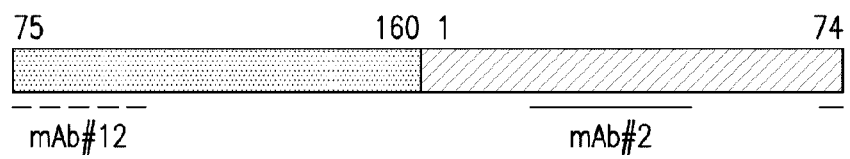
Bet v 1- rs 2
Bet v 1- mosaic
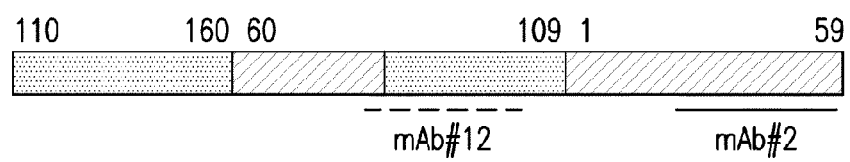
FIG.10A

FIG. 10B rαBet v 1

Bip 1 mAb#2 mAb#12 1

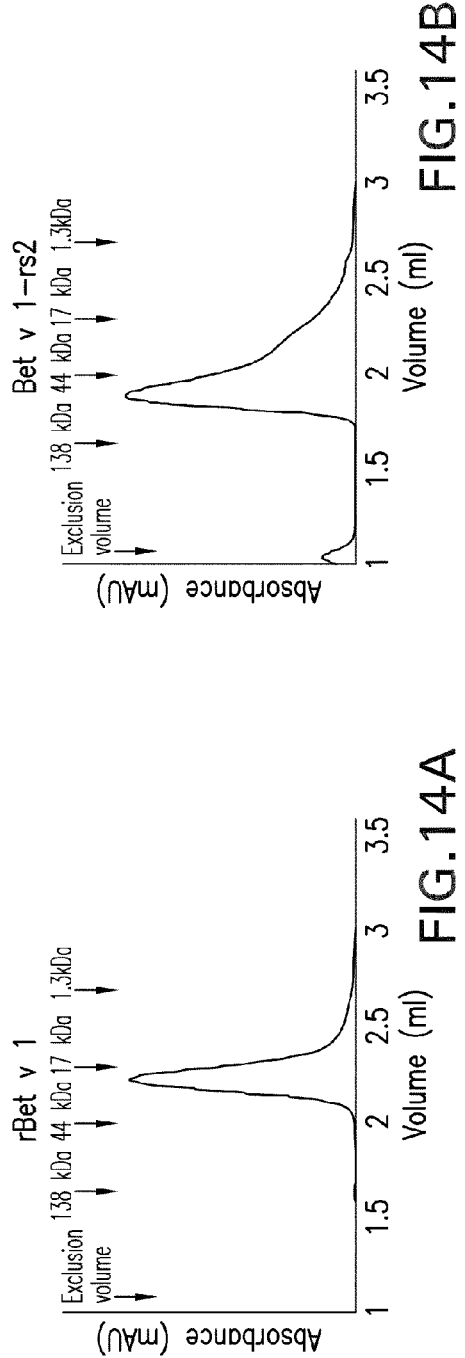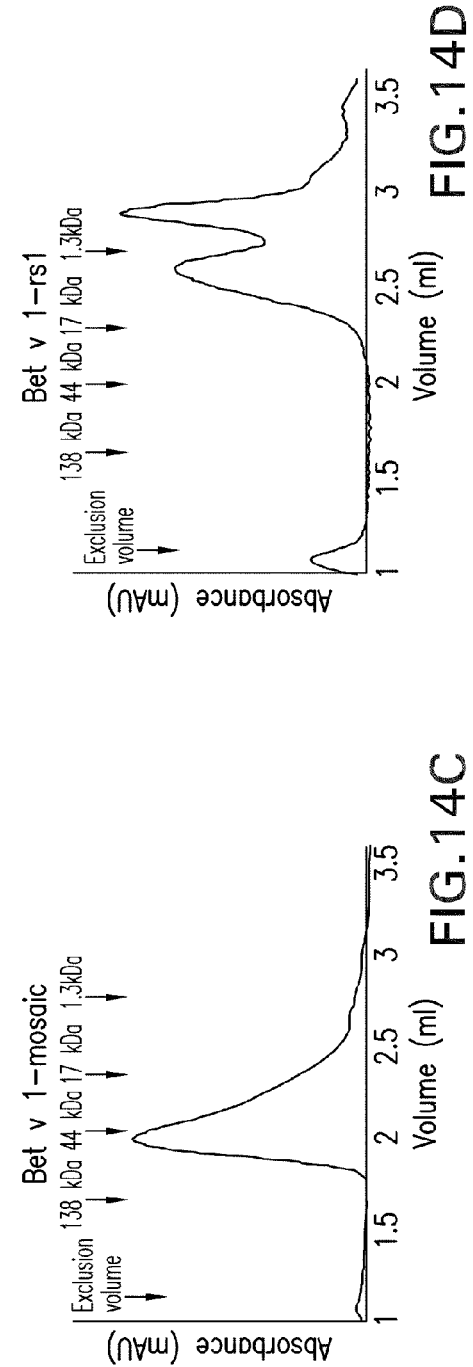
FIG. 14A FIG. 14B FIG. 14C FIG. 14D

Table 1.

| | Position aa | Sequence | | Number of aa | Molecular weight | Isoelectric point |
|---|---|---|---|---|---|---|
| Peptide 1 | 1-33 | VPKVIFTVEKGSNEKHLAVLVKYEGDTMAEVELC | SEQ ID NO: 3 | 34 | 3765.02 | 4.87 |
| Peptide 2 | 34-65 | REHGSDEWAMTKGEGGWTFDSEEPLQGPFNC | SEQ ID NO: 4 | 33 | 3696.8 | 4.03 |
| Peptide 3 | 66-96 | CFRFLTEKGMKNVFDDWPEKYTIGATYAPEE | SEQ ID NO: 5 | 32 | 3698.91 | 4.45 |

FIGURE 19

Induction of immediate skin reactions with Phl p 2 and Phl p 2-Mosaic

| Individual 1 | mean wheal diameter (mm) | | Individual 2 | mean wheal diameter (mm) | |
|---|---|---|---|---|---|
| | P2 | P2M | | P2 | P2M |
| 1 μg/ml | 9 | 0 | 1 μg/ml | 5 | 0 |
| 2 μg/ml | 10 | 0 | 2 μg/ml | 5 | 0 |
| 4 μg/ml | 11 | 5 | 4 μg/ml | 6 | 0 |
| 8 μg/ml | 14 | 4 | 8 μg/ml | 7 | 0 |
| 16 μg/ml | 10 | | 16 μg/ml | 9 | 3 |
| Timothy grass | 15 | | Timothy grass | 10 | |
| Histamine | 8 | | Histamine | 8 | |

Table 2.

FIGURE 20

Rabbit anti P2-Mosaic and rabbit anti rPhl p 2 inhibit IgE binding of grass pollen allergic patients to rPhl p 2

| Patient | % inhibition | |
|---|---|---|
| | anti-P2M | anti-rPhl p 2 |
| 1 | 39.54 | 76.93 |
| 2 | 9.25 | 63.97 |
| 3 | 23.20 | 52.91 |
| 4 | 14.38 | 40.86 |
| 5 | 18.27 | 38.97 |
| Mean | 20.93 | 54.73 |

Table 3.

HYPALLERGENIC MOSAIC ANTIGENS AND METHODS OF MAKING SAME

PRIORITY

This application is a continuation-in-part of U.S. patent application Ser. No. 12/349,614 filed Jan. 7, 2009, which is a divisional of U.S. patent application Ser. No. 10/542,735, filed Jul. 21, 2005 (now U.S. Pat. No. 7,491,396 issued Feb. 17, 2009), which, in turn, is a national stage of PCT Application No. PCT/EP03/14507, filed Dec. 18, 2003, which, in turn, claims priority to European Patent Application No. 03.001242.1 filed Jan. 21, 2003. The contents of these priority applications are hereby incorporated by reference in their entirety.

SEQUENCE LISTING

The instant application contains a Sequence Listing that has been submitted via EFS-Web and is hereby incorporated by reference in its entirety. Said ASCII copy, created on Jul. 8, 2011, is named LNK_002CIP_Sequence_Listing.txt, and is 16,425 bytes in size.

FIELD OF THE INVENTION

The present invention relates to mosaic antigens reassembled from naturally-occurring allergens, in particular plant pollen allergens, more particularly grass and tree pollen allergens. The mosaic antigens described herein display reduced allergenic activity and thus are useful as allergy vaccines for the treatment of allergic disorders and sensitized allergic patients and for prophylactic vaccination.

BACKGROUND OF THE INVENTION

A large percentage of the population suffers from IgE-mediated allergies. Many of those patients suffer from allergic reactions against several antigens. A high percentage of these allergic reactions are caused by plant allergens, particularly pollen from anemophilous (i.e., "wind loving") plants. Among North American plants, the most prolific producers of allergenic pollen are weeds, primarily ragweed, though sagebrush, redroot pigweed, lamb's quarters, Russian thistle (tumbleweed), and English plantain are also important. Grasses and trees are also primary sources of allergenic pollens. Although there are more than 1,000 species of grass in North America, only a few produce highly allergenic pollen. These are mostly summer grasses, examples of which include timothy grass, Kentucky bluegrass, Johnson grass, Bermuda grass, redtop grass, orchard grass, and sweet vernal grass. Examples of trees that produce allergenic pollen include members of the birch, oak, ash, elm, hickory, pecan, box elder, and mountain cedar families. Allergy to pollens from birch and related trees (alder, hazel), are quite prevalent in Northern and Middle Europe, North America, and certain parts of Australia and Asia.

The symptoms of allergy, such as allergic rhino conjunctivitis, asthma, dermatitis, hay fever, hives and even anaphylactic shock, arise from the interaction between antibodies and allergens, more particularly IgE recognition of allergens. In particular, IgE molecules bind to an allergen, for example, a plant pollen. The tail region of the IgE molecule, i.e., the Fc part, binds to Fc receptors that are mainly located on the surface of mast cells in tissues and basophils in the blood. Antigen binding triggers the mast cells or basophils to secrete a variety of cytokines and biologically active compounds, especially histamine. These molecules cause blood vessels to dilate and become leaky which in turn helps white blood cells, antibodies and complements components to enter sites of reaction. Those molecules are on the other hand largely responsible for the symptoms of allergic reactions. There are different degrees of allergic reactions which range from slight itching of the eyes and the symptoms of a slight cold over severe pains to live-threatening symptoms like anaphylactic shock which may occur for example after the sting of a bee.

While drug therapy may reduce the symptoms of an allergic response, only allergen-specific immunotherapy (ASIT) can serve to avoid the allergic reaction and thereby effectively "treat" allergic disorders. ASIT is based on the administration of a small amount of a disease-eliciting allergen to the patient in order to induce antigen-specific nonresponsiveness. More particularly, the administration of a small amount of antigen leads to the production of allergen-recognizing IgG antibodies or "blocking antibodies". These so-called blocking antibodies largely inhibit contact between the allergen and the IgE molecules present in the patient's body; thus, the reaction between the allergen and the mast cells mediated by IgE molecules is largely avoided.

In the field of allergen-specific immunotherapy (ASIT), different allergy vaccines have been developed. Previously, these vaccines simply consisted of small amounts of the native allergen or natural allergen extracts to be applied to the patient. However, with the development of genetic engineering, vaccines based on recombinant allergens have been produced. A major disadvantage of such allergen-containing vaccines is that the application of such vaccines causes in the patient unwanted side-effects. If, for example, the allergen against which the patient is allergic is applied subcutaneously to the patient an unwanted side-effect like itching up to anaphylactic shock can occur since the IgE antibodies present in the patient's body react with the allergen and cause the allergic reaction.

In an effort to overcome the undesired side-effects of conventional immunotherapeutic agents, hypoallergenic allergens, i.e., allergens having reduced allergenic potential as compared to their naturally-occurring counterparts, are eagerly sought.

SUMMARY OF THE INVENTION

To that end, Applicants have developed a process for the preparation of a mosaic antigen derived from a naturally-occurring allergen whereby the complete amino acid sequence of a naturally-occurring allergen (or "native allergen" or "wild-type allergen") is reassembled in a manner in which sequences relevant to the induction of blocking IgG antibodies and the dominant T-cell epitopes are preserved while those sequences associated with IgE recognition are avoided or reduced. Thus, the present invention is directed to a method of making reassembled mosaic antigens and reassembled mosaic antigens obtained therefrom.

Accordingly, it is an object of the present invention to provide a hypoallergenic mosaic antigen assembled from all or substantially all of the amino acids of a native allergen, though with the amino acid components arranged in a different order. In one preferred embodiment, the "different order" arises from exchanging an allergen fragment that includes the naturally-occurring N-terminus with an allergen fragment that includes the naturally-occurring C-terminus. Additionally or alternatively, at least two of fragments that are in adjacent positions in the naturally-occurring allergen may be oriented into non-adjacent positions in the reassembled mosaic antigen.

Hypoallergenic mosaic antigens of the present invention are designed to retain at least one T-cell epitope specific to the naturally-occurring allergen and to be capable of inducing IgG antibodies that hinder IgE binding to the naturally-occurring allergen. Accordingly, it is an object of the present invention to provide a hypoallergenic mosaic antigen capable of inducing allergen-specific IgG antibodies that recognize the naturally-occurring allergen and inhibit recognition of the naturally-occurring allergen by serum IgE from allergic patients. In a preferred embodiment, the mosaic antigen has reduced allergenic activity as compared to the naturally-occurring allergen. For example, the IgE reactivity of the mosaic antigen have an IgE reactivity value that is no more than 10% of that obtained for the naturally-occurring allergen, preferably no more than 5% thereof.

Although the present invention is not limited to any one particular allergen or class or allergen, plant allergens, especially plant pollen allergens, are preferred. In one particularly preferred embodiment, the plant pollen allergen is a birch pollen allergen, for example the major birch pollen allergen, Bet v 1.

Mosaic antigens of the present invention may be defined in terms of their peptide (amino acid) sequences. Illustrative examples of preferred peptide sequences are set forth in SEQ ID NOs: 15, 17, and 19. However, the present invention also extends to nucleotide (DNA, RNA) sequences that code for the hypoallergenic mosaic antigens described herein. Examples of preferred nucleotide sequences include DNA sequences coding for amino acid sequences of SEQ ID NO: 15, 17, and 19, and sequences complementary thereto.

It is a further object of the present invention to provide a method of making a reassembled mosaic antigen of the present invention, the method including the steps of:
  a. providing a wild-type protein allergen;
  b. cleaving the wild-type allergen into at least two, more preferably at least three, four or five preferably non-overlapping allergen fragments; and
  c. reassembling the allergen fragments to yield a mosaic antigen comprising all or substantially all of the amino acids of the original wild-type allergen, though arranged in a different order.

The method of the present invention involves a rational design approach that is distinct from the gene shuffling and molecular breeding techniques of the prior art, such as those described by Wallner et al. (*J. Allergy Clin. Immunol.*, vol. 120(2), August 2007, p. 374-380) and Short (U.S. Pat. No. 6,489,145). Unlike the prior art methods, the mosaic antigens of the present invention are not the result of random shuffling and screening but rather the result of affirmative design, wherein allergen fragments are selected for reassembly according to the following criteria:
  1. The allergen fragments should exhibit little to no IgE reactivity and/or IgE-mediated allergenic activity. Accordingly, one or more of the selected allergen fragments are characterized by a low ability to degranulate mast cells or basophils. Relative IgE reactivity and IgE-mediated allergenic activity may be experimentally determined using conventional assays and protocols.
  2. The allergen fragments should preferably retain important allergen-specific T-cell epitopes. The presence of requisite T-cell epitopes may be experimentally determined, e.g., by measuring the ability of the fragment to induce a T-cell mediated immune response, or, alternatively, may be determined in silico, e.g., using known T-cell epitope motifs.
  3. The allergen fragments should disrupt conformational IgE epitopes but retain peptide sequences capable of focusing IgG antibodies towards the wild-type IgE epitopes. With regard to the latter, by leaving intact portions of IgE epitopes or peptide sequences proximate to such IgE epitopes, one can substantially eliminate IgE reactivity while at the same time retain the ability to induce IgG antibodies that hinder IgE binding to the wild-type allergen (i.e., "blocking IgG antibodies"). Specific IgG antibodies that are directed against defined regions within the allergen sequence and compete with IgE binding to the allergen can be valuable tools in the rational design approach. Such antibodies for which the target binding site within the allergen sequence is roughly or exactly known can be used to localize yet unknown IgE epitopes within the allergen.

Accordingly, the method of the present invention allows for the production of mosaic antigens having a reduced or eliminated capacity to bind IgE while conserving at the same time those features of the allergen that are required to induce a T-cell mediated immune response. Thus, the reassembled mosaic antigens of the present invention are capable of inducing a strong allergen-specific IgG response, i.e., therapeutic levels of blocking IgG antibodies, while simultaneously inhibiting or suppressing IgE production. In this manner, the allergic and/or inflammatory response to the native allergen may be substantially avoided. As such, the mosaic antigens of the present invention find particular utility in the treatment of allergies and allergic disorders. Accordingly, it another object of the present invention to provide a method of treating an allergic disorder in a subject in need thereof including the step of administering to the subject a therapeutically effective amount of a mosaic antigen of the present invention or a DNA sequence coding for such an allergen.

The reassembled mosaic antigens of the present invention find utility in the treatment of an allergic disorder. Accordingly, it is yet another object of the present invention to provide methods for treating or preventing allergic disorders that include the step of administering one or more hypoallergenic mosaic antigens of the present invention to a subject in need thereof. In a preferred embodiment, the allergic disorder is a pollen allergy, more preferably birch pollen allergy, even more preferably allergic disorders caused by reaction to the major birch pollen allergen Bet v 1.

The mosaic antigens obtained according to the present invention may be easily combined with a pharmaceutically acceptable carrier, diluent and/or excipient and finished to a pharmaceutical preparation or medicament. Accordingly, is yet another object of the present invention to provide a medicament for the treatment or prevention of an allergic disorder.

The reassembled mosaic antigens of the present invention also find utility in the preparation of a vaccine for the treatment or prophylaxis of an allergic disorder. Accordingly, it is a further object of present invention to provide vaccines for the treatment of allergic disorders, more particularly vaccines that include one or more hypoallergenic mosaic antigens of the present invention. To that end, the mosaic antigens obtained according to the present invention may be combined with a suitable vaccine adjuvant and finished to a pharmaceutical acceptable vaccine preparation. A vaccine preparation of the instant invention may include further allergens, preferably wild-type allergens, especially a mixture of wild-type allergens, recombinant wild-type allergens, derivatives of wild-type protein allergens or mixtures thereof. Such mixtures may be specifically tailored for the needs (i.e., allergen profile) of a particular patient.

In addition to mosaic antigens per se, a nucleic acid coding for a mosaic antigen of the present invention or a nucleotide sequence complementary thereto may also serve as a suitable vaccine. Accordingly, it is yet another object of the present invention to provide a vaccine for the treatment or prevention of an allergic disorder comprising a nucleotide sequence coding for one or more mosaic antigen(s) of the present invention.

It will be understood by those skilled in the art that one or more aspects of this invention can meet certain objectives, while one or more other aspects can meet certain other objectives. Each objective may not apply equally, in all its respects, to every aspect of this invention. As such, the preceding and subsequently presented objects can be viewed in the alternative with respect to any one aspect of this invention.

These and other objects and features of the invention will become more fully apparent when the following detailed description is read in conjunction with the accompanying figures and examples. However, it is to be understood that both the foregoing summary of the invention and the following detailed description are of a preferred embodiment and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

BRIEF DESCRIPTION OF THE FIGURES

Various aspects and applications of the present invention will become apparent to the skilled artisan upon consideration of the brief description of the tables and figures and the detailed description of the present invention and its preferred embodiments that follows:

FIG. 1: Comparison of the IgE reactivity of synthetic Phl p 2-derived peptides and complete rPhl p 2 (recombinantly produced wild type allergen). Nitrocelluloses containing (A) dotted Phl p 2 peptides (P1, P2, P3), human serum albumin (HSA), a control peptide (P), and a non-cross-reactive timothy grass pollen allergen (rPhl p 5) and (B) rPhl p 5 and Phl p 2 (rPhl p 2) were exposed to sera from 35 grass pollen allergic patients (1-35) and to serum from a non-allergic individual (N).

FIG. 2: Schematic representation of recombinant his-tagged Phl p 2 wild-type and recombinant his-tagged Phl p 2 mosaic. The position of the three peptides is indicated. FIG. 2 discloses "6× Histidine" as SEQ ID NO: 23.

FIG. 4: cDNA (SEQ ID NO:2) and deduced amino acid sequence (SEQ ID NO:1) and of the his-tagged Phl p 2 mosaic. Amino acids are displayed in the single letter code, base pair and amino acid numbers are shown on the right margin.

FIG. 10: Hypoallergenic rBet v 1 derivatives. (A) Construction scheme of the rBet v 1 derivatives. The amino acids at the borders of the protein segments and the binding sites of two monoclonal antibodies mAb#2 and mAb#12 are indicated. (B) SDS-PAGE of purified rBet v 1 and rBet v 1 derivatives. M, molecular mass markers (kDa).

FIG. 14: Gel filtration profiles of rBet v 1 (A), Bet v 1-rs2 (B), Bet v 1-mosaic (C) and Bet v 1-rs1 (D). The x-axes show the elution volumes (ml) and the y-axes the absorbance of the proteins at 280 nm. Arrows indicate the approximate molecular masses (kea) as determined with the standards.

FIG. 16: Reactivity of IgG antibodies with rBet v 1 and rBet v 1 derivatives. Different dilutions (x-axes) of rabbit anti-rBet v 1 (anti-Bet v 1: ●), anti-rBet v 1 derivative antibodies (anti-Bet v 1-rs1: ■; anti-Bet v 1-rs 2: ▲; anti-Bet v 1-mosaic: x) or antibodies from a normal rabbit (—) were reacted with rBet v 1 (A), rBet v 1-rs1 (B), rBet v 1-rs2 (C) or rBet v 1-mosaic (D). Optical density (OD) values (y-axes) correspond to the amounts of bound antibodies.

FIG. 17: Reactivity of rabbit antibodies raised with aluminum hydroxide-adsorbed proteins by ELISA. Different dilutions (x-axes) of rabbit anti-rBet v 1 (anti-Bet v 1: ●), anti-rBet v 1 derivative antibodies (anti-Bet v 1-rs1: ■; anti-Bet v 1-rs 2: ▲; anti-Bet v 1-mosaic: x) or antibodies from a normal rabbit (—) were reacted with rBet v 1. Optical density (OD) values (y-axes) correspond to the amounts of bound antibodies.

FIG. 18 (Table 1): Characteristics of Phl p 2-derived synthetic peptides. Sequence, number of amino acids, position in the Phl p 2 allergen; molecular weight and bioelectric point of the peptides are displayed. Peptide 1 corresponds to SEQ ID NO:3, Peptide 2 corresponds to SEQ ID NO:4 and Peptide 3 corresponds to SEQ ID NO:5.

FIG. 19 (Table 2): Immediate type skin reactions to complete rPhl p 2 and to Phl p 2 mosaic (P2M). Two timothy grass pollen allergic patients (Individual 1,2) were tested for skin reactivity with P2 and P2M. The mean wheal diameters (mm) are displayed for five different concentrations of rPhl p 2 and Phl p 2 mosaic, as well as for timothy grass pollen extract and histamine.

FIG. 20 (Table 3): Inhibition of grass pollen allergic patients IgE binding to rPhl p 2 by rabbit αP2M and rabbit αP2 antibodies. The percentage inhibition of IgE binding is displayed for 5 patients.

DETAILED DESCRIPTION OF THE PRESENT INVENTION AND PREFERRED EMBODIMENTS

Figure 3:
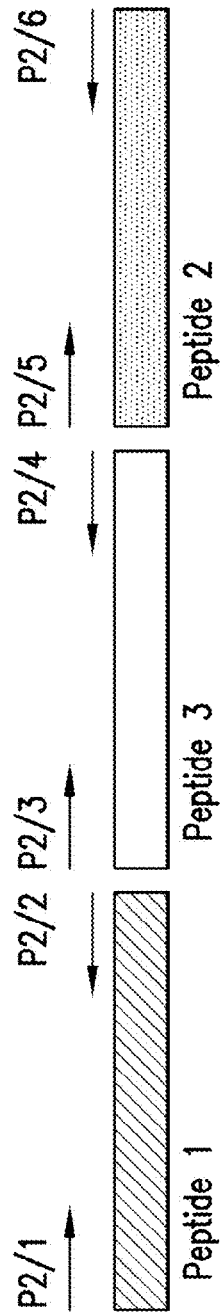
FIG. 3: DNA sequence of the primers used for the construction of the Phl p 2 mosaic and schematic representation of PCR approach used for the assembly of the cDNA coding for the rPhl p 2 mosaic. The Nde I and Eco R I restriction sites are underlined in primer P2/1 and P2/6, respectively. The primers correspond to SEQ ID NO:6 to SEQ ID NO:11.
Figure 5:
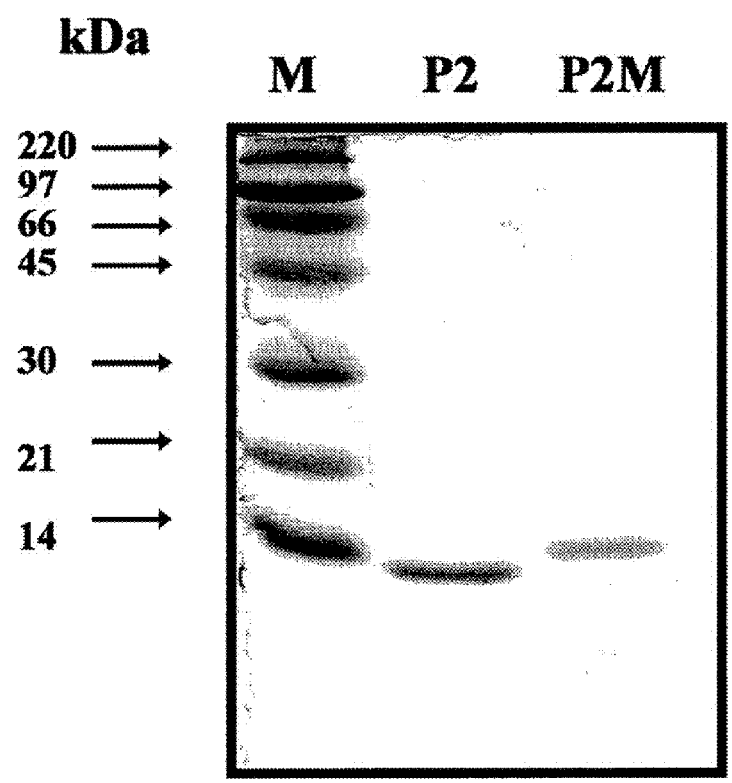
FIG. 5: Purity of rPhl p 2 mosaic and rPhl p 2. Compassion stained gel containing Phl p 2 (lane P2), Phl p 2 mosaic (lane P2M) and a molecular weight marker (lane M).

The present invention relates to a mosaic antigen assembled from all or substantially of the component amino acids of a naturally-occurring allergen, in particular a plant allergen, more particularly an allergen derived from tree and grass pollen. The reassembled mosaic antigens described herein display reduced allergenic activity as compared to their naturally-occurring counterparts and thus are useful as medicaments for the treatment of sensitized allergic patients as well as allergy vaccines for prophylactic vaccination. Particular embodiments of the mosaic antigen of the present invention, the therapeutic constructs associated therewith, and the methods of making and using same are described in greater detail below.

Although any methods and materials similar or equivalent to those described herein can be used in the practice or testing of embodiments of the present invention, the preferred methods, devices, and materials are now described. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the present invention which will be limited only by the appended claims.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the present invention, the following definitions apply:

1. Definitions

As used herein and in the appended claims, the singular forms "a", "an" and "the" include plural reference unless the context clearly dictates otherwise. Thus, for example, reference to a "molecule" is a reference to one or more molecules and equivalents thereof known to those skilled in the art, and so forth.

As used herein, the term "allergen" refers to a nonparasitic environmental antigen capable of stimulating a type-I hypersensitivity reaction (i.e., an IgE response) in atopic individuals.

As used herein, the phrases "naturally-occurring allergen" and "native allergen" are interchangeably used to refer to the complete wild-type form of the allergen as it is found in nature.

In the context of the present invention, the native allergen may be an indoor, animal, food or seasonal allergen. A list of illustrative allergens is found in Table A of co-pending U.S. application Ser. No. 11/720,598, published as US 2008/0286311, the contents of which are incorporated by reference herein and of which Table A is reproduced herein below.

Of the indoor allergens, the major house dust mite allergens, in particular Der p 1 and Der p 2, and the major storage mite allergens, especially Lep d 2, are particularly preferred. In terms of animal allergens, the present invention contemplates mosaics of the major cat allergen, Fel d 1, as well as those derived from the major bee and wasp allergens. In terms of food allergens, olive allergens, particularly major allergens of *Olea europea* such as Ole e 1 are particularly preferred.

In terms of seasonal allergens, plant allergens, particularly anemophilous or wind-carried plant pollens, even more preferably grass, weed and tree pollens, are particularly preferred. Examples of preferred grass pollens include, but are not limited to, those derived from timothy grass, Kentucky bluegrass, Johnson grass, Bermuda grass, redtop grass, orchard grass, and sweet vernal grass. Of the grass pollens, the major allergens of timothy grass, especially Phl p 1 (see US 2009/0098167), Phl p 2 (see U.S. Pat. No. 7,491,396), Phl p 5, Phl p 6, Phl p 7, and Phl p 12 (see US 2008/0286311) are particularly preferred.

Examples of preferred weed pollens include, but are not limited to, those derived from ragweed, sagebrush, pigweed, tumbleweed, cockleweed, sticky-weed and Russian thistle. Of the weed pollens, the major allergens of short ragweed (*Ambrosia artemisiifoli*), e.g., Amb a 1, and sticky-weed (*Parietaria judaica*), e.g., Par j 2, are particularly preferred.

Examples of preferred tree pollens include, but are not limited to, those derived from members of the birch, oak, ash, elm, hickory, pecan, box elder, and mountain cedar families. Of the tree pollens, the birch pollen allergens, Bet v 1 and Bet v 4, are of particular interest. As noted above, the present invention relates to a hypoallergenic mosaic antigen having a rearranged amino acid sequence as compared to its naturally-occurring counterpart. In the context of the present invention, term "mosaic antigen" refers to a polypeptide allergen assembled from all or substantially all of amino acids of a naturally-occurring allergen, though arranged in a different order. The reassembled mosaic antigen of the present invention may be derived from a naturally-occurring allergen that has been cleaved into at least two, preferably at least 3 or 4, preferably non-overlapping subset components or fragments. When the amino acid sequence of the native allergen is known, it is common general knowledge of a person skilled in the art to prepare peptides of varying lengths therefrom using conventional technologies. For example, the subset peptide fragments can be prepared by chemical synthesis. Alternatively, the peptides can be readily prepared by Polymerase Chain Reaction since suitable primers can be easily synthesized when the sequence is known.

Once the native allergen has been cleaved into two, three or more fragments, those fragments can be newly assembled to provide the mosaic antigen of the present invention. The mosaic antigen is preferably "hypoallergenic", i.e., has reduced allergenic potential as compared to the native allergen. In the context of the present invention, the term "hypoallergenic" means that the IgE reactivity of the mosaic antigen has been reduced to not more than 20%, preferably not more than 10%, even more preferably not more than 5% of an IgE reactivity value obtained for the native allergen.

In the simplest case, the naturally-occurring allergen is divided at single a cleavage site into two non-overlapping peptide fragments. In the context of the present invention, the term "cleavage site" refers to the position in the polypeptide where one fragment ends and another fragment starts. Thus, the two allergen fragments include fragment A having the N-terminus and ending at the cleavage site and fragment B starting with the cleavage site and ending with the carboxy terminus of the polypeptide. The two fragments may then be rearranged in such a manner that now fragment B represents the N-terminus and fragment A represents the C-terminus. This resulting "B-A" configuration is an example of a reassembled mosaic antigen.

The mosaic allergen of the present invention is preferably produced recombinantly, though the subset allergen fragments may also be chemically synthesized and subsequently linked together.

As noted above, the reassembled mosaic antigens of the present invention find particular utility in the treatment and prevention of allergic disorders. In the context of the present invention, the terms "allergy" and "allergic disorder" are interchangeably used to refer to any disorder that is caused by a hypersensitive reaction of the immune system, typically a type I or immediate hypersensitivity, to a normally harmless environmental substance (i.e., an allergen). Examples of allergic disorders include asthma, eczema, contact dermatitis, hives, hay fever, allergic rhinitis and rhinoconjunctivitis, airborne allergies and hay fevers (such as ragweed and birch pollen allergies). The present invention is particularly suited to the treatment of allergy to airborne particles such pollens. In these cases, symptoms typically arise in areas in contact with air, such as eyes, nose and lungs. For instance, allergic rhinitis, also known as "hay fever", causes irritation of the nose, sneezing, and itching and redness of the eyes Inhaled allergens can also lead to asthmatic symptoms, caused by narrowing of the airways (bronchoconstriction) and increased production of mucus in the lungs, shortness of breath (dyspnea), coughing and wheezing.

Although applications of the reassembled mosaic antigen of the present invention are described in detail below in the context of human therapy, one of skill in the art will readily recognize that the present invention has both human medical and veterinary applications. Accordingly, the terms "subject" and "patient" are used interchangeably herein to refer to the person or animal being treated or examined. Exemplary animals include house pets (e.g., dogs and cats), livestock (e.g., cows, horses, etc.) and zoo animals. In a preferred embodiment, the subject is a mammal, more preferably a human.

2. Methods of Making Mosaic Antigens

The present invention relates to hypoallergenic mosaic antigens assembled from all or substantially all of the amino acid components of a naturally-occurring allergen, though rearranged into a different order. In the context of the present invention, the mosaic antigen may be obtained by (a) cleaving the naturally-occurring allergen into at least two allergen fragments, preferably at least three non-overlapping allergen fragments; and reassembling the allergen fragments to yield an amino acid sequence that includes substantially all of the amino acids of the original naturally-occurring allergen, though arranged in a different order.

As noted above, mosaic antigens of the present invention result from the intentional selection of allergen fragments that meet certain criteria. Firstly, the allergen fragments selected for reassembly should exhibit reduced allergenic activity. The allergenic activity of the allergen fragments and/or mosaic antigen may be experimentally confirmed, for example, by reacting the peptide of interest with sera from patients that are allergic to the naturally-occurring allergen.

Accordingly, it is an important aspect of the present invention to divide the wild-type allergen into such fragments that substantially do not react with IgE antibodies. As noted above, the IgE reactivity of the mosaic antigen is preferably reduced to not more than 20%, preferably not more than 10%, even more preferably not more than 5% of an IgE reactivity value obtained for the native allergen. If a particular allergen fragment still reacts with IgE antibodies in a substantial amount, such fragment should not be used for the preparation of the mosaic antigen. It is advisable to test the fragments of the naturally occurring antigen to be used in the mosaic antigen with sera from different allergic patients since there may be variations with regard to specificity and amount of IgE concentration in each serum.

Reduced allergenic activity may also be characterized by a low ability to degranulate mast cells or basophils. Relative IgE reactivity and IgE-mediated allergenic activity may be experimentally determined using conventional assays and protocols such as those described in the Examples section herein. Examples of conventional in vitro assays suitable for assessing allergenic activity include RAST (Sampson and Albergo, J. Allergy Clin. Immunol. 74:26, 1984), ELISAs (Burks et al., N. Engl. J. Med. 314:560, 1986), immunoblotting (Burks et al., J. Allergy Clin. Immunol. 81:1135, 1988), basophil histamine release assays (Nielsen, Dan. Med. Bull. 42:455, 1995 and du Buske, Allergy Proc. 14:243, 1993) and others (Hoffmann et al., Allergy 54:446, 1999).

It is also imperative that the selected allergen fragments retain important allergen-specific T-cell epitopes. The presence of requisite T-cell epitopes may be experimentally determined, e.g., by measuring the ability of the fragment to induce a T-cell mediated immune response, or, alternatively, may be determined in silico, e.g., using known T-cell epitope motifs, such as those available in the Swiss-Prot protein database, alone or in combination with conventional mapping techniques, such as those described by Thomas Zeiler and Tuomas Virtanen in their chapter entitled "The Mapping of Human T-Cell Epitopes of Allergens" from *Methods in Molecular Medicine: Allergy Methods and Protocols*, Humana Press, 2008, Volume 138, pp. 51-56.

As a further selection criteria, the cleavage/fragmentation process preferably disrupts conformational IgE epitopes but preserves peptide sequences capable of focusing IgG antibodies towards the wild-type IgE epitopes. With regard to the former, IgE antibodies present in sera will react with the peptide if an IgE epitope is present on the peptide. If there are, however, no linear IgE epitopes or if conformational IgE epitopes are destroyed by separating the whole naturally occurring allergen there will be no binding of IgE with the peptide. The IgE antibodies can subsequently easily be detected by reaction with specific anti-antibodies that bind to the IgE antibody. Those anti-antibodies are usually labeled for detection.

With regard to the latter, by leaving intact portions of IgE epitopes or peptide sequences proximate to such IgE epitopes, one can substantially eliminate IgE reactivity while at the same time retain the ability to induce IgG antibodies that hinder IgE binding to the wild-type allergen (i.e., "blocking IgG antibodies").

Bearing in mind the above-noted criteria, the optimum cleavage site(s) and resulting allergen fragments may be readily determined. For example, using sequence analysis techniques and rational design approaches that are conventional in the art, one of skill in the art can readily identify B-cell epitopes capable of inducing allergen-specific blocking IgG antibodies and major T-cell epitopes. Preferred mosaic antigens retain the ability to induce immunotherapeutic levels of allergen-specific blocking IgG antibodies and the major T-cell epitopes while simultaneously exhibiting reduced allergenic activity. When the naturally-occurring allergen is to be split into two non-overlapping fragments, only one cleavage site is required. The resulting fragments are referred to herein as "A" and "B", wherein the A fragment includes the N-terminus and the B fragment includes the C-terminus. Following the guidance herein, the reassembled mosaic antigen will have a B-A order, wherein the B fragment that now constitutes the N-terminus and the A fragment includes the C-terminus.

However, the instant mosaic techniques of the present invention are not restricted to two fragments. In fact, the naturally-occurring allergen may divided into three (A, B, C), four (A, B, C, D), five (A, B, C, D, E), six (A, B, C, D, E, F), and indeed any number of subset peptide components. The more parts formed, the more options for providing mosaic antigen are provided. Nevertheless, for best results, it is preferable that the peptide fragments to be reassembled be of approximately equal size and be as large as possible. Each fragment should include at least 10 amino acid residues, especially at least 15 amino acid residues. The ideal fragment size may vary, ranging from as little as 10 to 40 amino acids, upwards to 100 to 120 amino acids, more preferably from 30 to 70 amino acids.

When a naturally-occurring allergen having a native order of A-B—C is to be split into three fragments, the possible mosaic antigens include: B—C-A; B-A-C; C—B-A; C-A-B and A-C—B. However, when reassembling the fragments to form the mosaic antigen, it is preferable to avoid combining fragments that are localized in adjacent positions in the naturally-occurring allergen, e.g. C, A, B. The theory is that IgE binding epitopes may be formed again on the mosaic antigen. It is, however, essential that the mosaic antigen contain substantially all amino acids of the naturally-occurring antigen. Certainly some amino acids that clearly have no functions may be deleted and other amino acids may be deleted for production reasons. Nevertheless, the mosaic antigen should maintain many amino acids as possible. However, additional amino acids may be added to the mosaic antigen to facilitate production or the expression.

3. Mosaic Antigen Embodiments

The mosaic approach to hypoallergenic allergen design disclosed herein may be applied to any of a number of native allergens, though plant allergens, particularly grass and tree pollen allergens are most preferred.

In the context of grass pollen allergens, allergens of groups I and II. Preferred group II allergens are described in the following publications:

Freidhoff L R, Ehrlich-Kautzky E, Grant J H, Meyers D A, Marsh D G. A study of the human immune response to *Lolium perenne* (rye) pollen and its components, Lol p I and Lol p II (rye I and rye II). I. Prevalence of reactivity to the allergens and correlations among skin test, IgE antibody, and IgG antibody data. J Allergy Clin Immunol 1986, 78, 1190-1201.

Freidhoff L R, Ehrlich-Kautzky E, Meyers D A, Marsh D G. A study of the human immune response to *Lolium perenne* (rye) pollen and its components, Lol p I and Lol p II (Rye I and Rye II). II. Longitudinal variation of antibody levels in relation to symptomatology and pollen exposure and correction of seasonally elevated antibody levels to basal values. J Allergy Clin Immunol 1987, 80, 646-655.

Ansari A A, Shenbagamurthi P, Marsh D G. Complete amino acid sequence of a *Lolium perenne* (perennial rye grass) pollen allergen, Lol p II. J Biol Chem 1989, 264, 11181-11185.

Dolecek C, Vrtala S, Laffer S, Steinberger P, Kraft D, Scheiner 0, Valenta R. Molecular characterization of Phl p II, a major timothy grass (*Phleum pratense*) pollen allergen. FEBS Lett 1993, 335, 299-304.

Figure 6A:
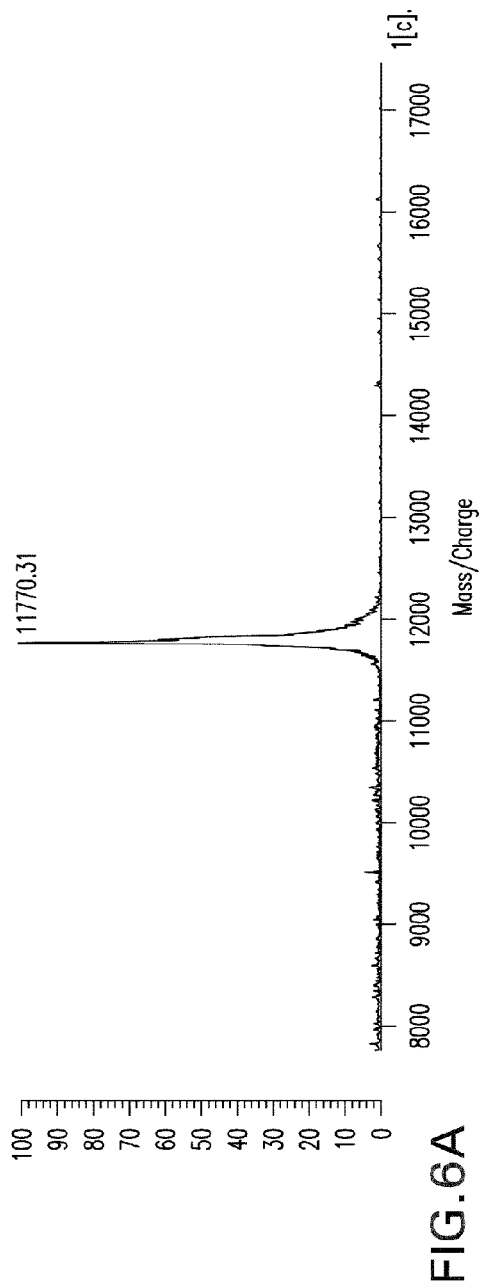
FIG. 6: Mass spectroscopical analysis of purified rPhl p 2 mosaic (A) and rPhl p 2 (B). The mass/charge ratio is shown on the x-axis and the signal intensity is expressed as percentage of the most intensive signal obtained in the investigated mass range.
Figure 6B:
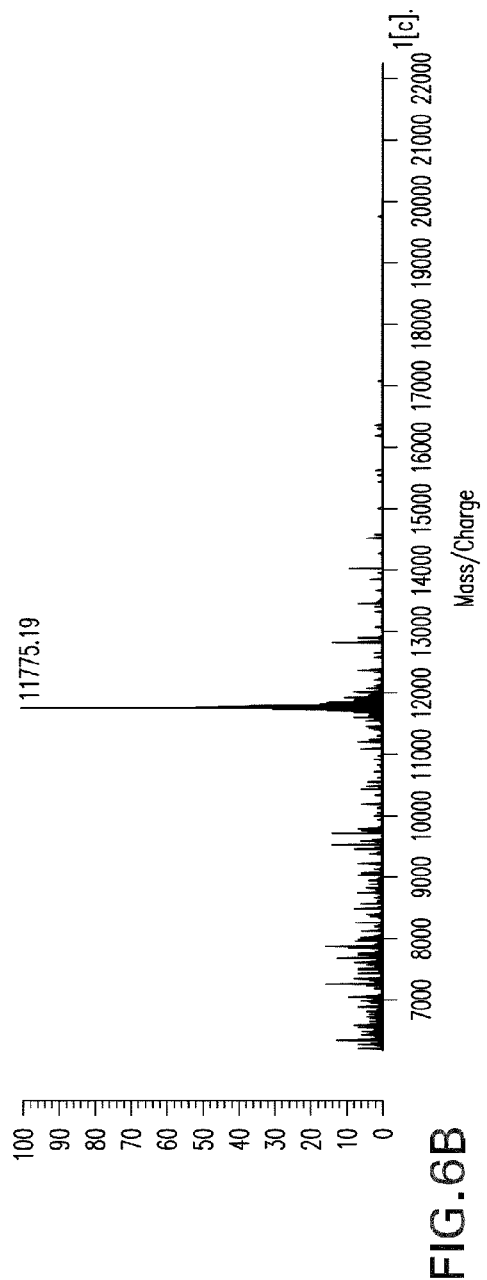
Figure 7:
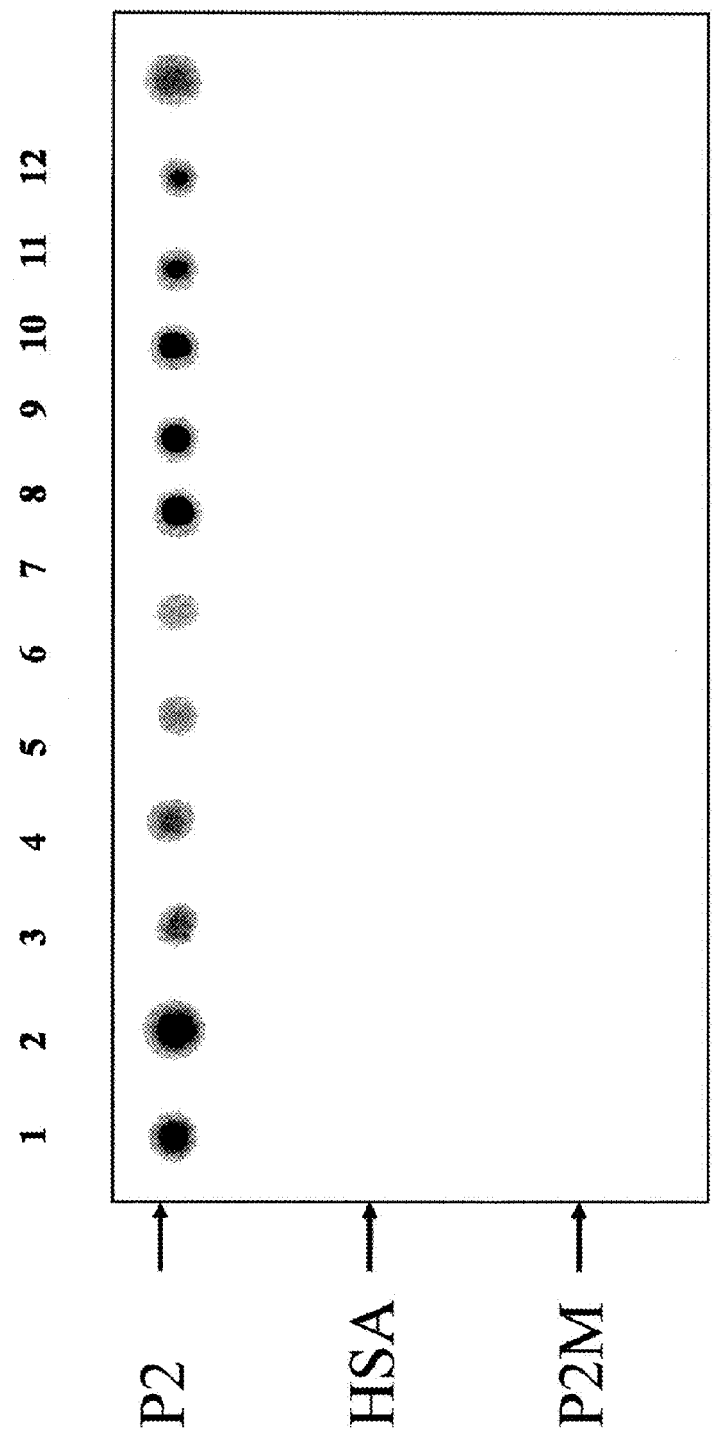
FIG. 7: Comparison of the IgE binding capacity of rPhl p 2 (P2) and the rPhl p 2 mosaic (P2M). Nitrocellulose dotted rPhl p 2 (P2) and rPhl p 2 mosaic (P2M), as well as human serum albumine (HSA) were probed with serum from 12 Phl p 2-reactive grass pollen allergic patients (1-12). Bound IgE antibodies were detected with $^{125}$I-labeled anti-human IgE antibodies and visualized by autoradiography.

In one particularly preferred embodiment, the allergen used for the mosaic antigen is the timothy grass pollen allergen Phl p 1 or Phl p 2. The mature sequence of the timothy grass pollen allergen Phl p 1 is found in Genbank Accession Number X78813. The three-dimensional structure of Phl p 1 has been solved by X-ray crystallography and is available in the PDB (1N10). From this 3D structure, IgE and T-cell epitopes have been experimentally determined and suitable mosaic proteins have been devised. See Ball et al., "Reducing Allergenicity by Altering Allergen Fold: A Mosaic Protein of Phl p 1 for Allergy Vaccination", *Allergy* 2009, vol. 64: pp. 569-580, the contents of which are incorporated herein in their entirety. In particular, Ball et al. describe a recombinant Phl p 1 mosaic, P1M, having a B-D-A-C rearrangement that, as compared to wild-type rPhl p 1 (P1):

exhibits a substantial reduction in IgE activity (see FIG. 3);

exhibits virtually no allergenic activity as demonstrated by basophil activation and histamine release assays (see FIGS. 4 and 6); and induces IgG antibodies in vivo that inhibit the binding of allergic patients' serum IgE to wild-type allergen (i.e., "blocking antibodies") (see FIG. 7).

As such, the mosaic antigen is able to provide the benefits of wild-type allergen vaccination with virtually none of the undesired allergic side reactions associated therewith.

The amino acid and nucleotide sequences for the timothy grass pollen allergen 2 are disclosed in WO 94/23035. A more detailed description of the Phl p 2 from timothy grass pollen is provided in De Marino et al., Structure (1999) Vol. 7, No. 8, p. 943-952. The Phl p 2 antigen is preferred since it reacts with serum IgE from about 70% of grass pollen allergic individuals and elicits histamine release from basophils of sensitized patients.

In the course of the present invention, it has been found that the Phl p 2 allergen is preferably split into three peptides, namely peptide 1 having amino acids 1-33, peptide 2 having amino acids 34-64 and peptide 3 having amino acids 65-96. By rearranging the peptides in the order 1, 3 and 2 a mosaic antigen is provided which can be used for hypoallergenic vaccination. This mosaic antigen has the advantage that a sufficient amount of blocking IgE antibodies is produced, but the undesired side-reactions associated with the vaccination are nearly completely avoided. The amino acid sequence of the preferred Phl p 2 mosaic antigen has SEQ ID NO:1. The DNA coding for this preferred mosaic antigen has SEQ ID NO:2.

In the context of tree pollen allergens, pollens derived from members of the birch, oak, ash, elm, hickory, pecan, box elder, and mountain cedar families. Of these, the major birch pollen allergen, Bet v 1, is of particular interest. The amino acid and nucleotide sequences for wild-type Bet v 1 and proposed mosaics thereof are set forth herein in SEQ ID Nos: 13-20.

In the course of the present invention, it has been found that the Bet v 1 allergen may be split into two or three peptides. In a first embodiment, referred to herein as Bet v 1 rs1, the native allergen is split into two peptide fragments, fragment A' composed of amino acids 1-74 of SEQ ID NO: 13 and fragment B' composed of amino acids 75-160 of SEQ ID NO: 13. The fragments are reassembled in a B'-A' configuration [(75-160)-(1-74)] to give rise to Bet v 1 rs1, the amino acid and nucleotide sequences for which are set forth herein in SEQ ID NOs; 15 and 16.

In a second embodiment, referred to herein as Bet v 1 rs2, the native allergen is again split into two peptide fragments, with fragment A" composed of amino acids 1-109 of SEQ ID NO: 13 and fragment B" composed of amino acids 110-160 of SEQ ID NO: 13. The fragments are reassembled in a B"-A" configuration [(110-160)-(1-109)] to give rise to Bet v 1 rs2, the amino acid and nucleotide sequences for which are set forth herein in SEQ ID NOs; 17 and 18.

In a third embodiment, referred to herein as Bet v 1 m, the native allergen is split into three peptide fragments, with fragment A composed of amino acids 1-59 of SEQ ID NO: 13, fragment B composed of amino acids 60-109, and fragment C composed of amino acids 110-160 of SEQ ID NO: 13. The fragments are reassembled in a C—B-A configuration [(110-160)-(60-109)-(1-59)] to give rise to Bet v 1 m, the amino acid and nucleotide sequences for which are set forth herein in SEQ ID NOs; 19 and 20.

In all three cases, as compared to wild-type rBet v 1, the derivatives:
  exhibited no detectable IgE activity (see FIG. 12);
  exhibited more than 100 fold reduction in allergenic activity as demonstrated by basophil activation assay (see FIG. 13); and
  induced IgG antibodies that inhibit the binding of allergic patients' serum IgE to wild-type allergen (i.e., "blocking antibodies") (see FIG. 14).

As such, the mosaic antigen is able to provide the benefits of wild-type allergen vaccination, with virtually none of the undesired allergic side-reactions associated therewith.

4. Therapeutic Methods, Medicaments and Vaccines

As noted above, the reassembled hypoallergenic mosaic antigens of the present invention, being capable of inducing a strong allergen-specific IgG response, i.e., therapeutic levels of blocking IgG antibodies, while simultaneously inhibiting or suppressing IgE production, find particular utility in the treatment of allergies and allergic disorders.

Accordingly, one aspect of the present invention relates to a method of treating an allergic disorder in a subject in need thereof including the step of administering to the subject a therapeutically effective amount of a mosaic antigen of the present invention or a nucleic acid coding for such an allergen. In a preferred embodiment, the mosaic antigen is formulated for parenteral administration, more preferably for intradermal or subcutaneous injection, including, as needed, suitable pharmaceutical carrier(s), excipients(s) and diluent(s) such as are conventional in the art. The pharmaceutically formulated allergen may be singly or repeatedly administered, for example in accordance with conventional immunotherapy protocols.

Another aspect of the present invention relates to the use of a mosaic antigen in connection with the preparation of a medicament for the treatment or prevention of an allergic disorder. In the context of medicament preparation, the mosaic antigen is preferably formulated with a suitable pharmaceutical carrier and administered together with an adjuvant. Examples of suitable adjuvants include alum compositions, such aluminum hydroxide gel. Alternatively, the mosaic antigen may be covalent bound to another component that generally enhances the immunologic reaction of the body. Carbohydrate bead compositions such as described in co-pending U.S. application Ser. No. 10/510,655 filed Nov. 30, 2004, the contents of which are incorporated herein, are also contemplated.

Yet another aspect of the present invention relates to the use of a mosaic antigen of the present invention in connection with the preparation of a vaccine for the treatment or prophylaxis of an allergic disorder. To that end, a nucleic acid coding for a mosaic antigen of the present invention or a nucleotide sequence complementary thereto may serve as a DNA or RNA vaccine. Accordingly, it is yet another object of the present invention to provide a vaccine for the treatment or prevention of an allergic disorder comprising a nucleic acid coding for one or mosaic antigen(s) of the present invention. The vaccine is preferably formulated for subcutaneous administration, optionally including a pharmaceutically acceptable carrier and/or suitable vaccine adjuvant. For nucleic acid vaccines, a suitable polynucleotide sequence is inserted into the target cells. In addition to the sequence coding for the mosaic antigen, such a nucleotide vaccine may also contain regulatory elements like promoters, ribosome binding sites or termination sequences. Such nucleotide sequences are preferably incorporated into a suitable carrier that allows the nucleotide to come to the protein synthesizing machinery of the cells.

Hereinafter, the present invention is described in more detail by reference to the Examples. However, the following materials, methods and examples only illustrate aspects of the invention and in no way are intended to limit the scope of the present invention. As such, methods and materials similar or equivalent to those described herein can be used in the practice or testing of the present invention.

EXAMPLES

Example 1

Mosaic Derivatives of the Phl p 2 Timothy Grass Allergen

A. Preparation of Synthetic Phl p 2-Derived Peptides Lacking Allergenic Activity In order to identify Phl p 2 fragments without allergenic activity, peptides, each comprising about ⅓ of the Phl p 2 protein were chemically synthesized (FIG. 18-Table 1). The peptides had a length between 32 and 34 amino acids with molecular weights of around 3.7 kDa and together covered the complete Phl p 2 amino acid sequence.

The three peptides were synthesized using Fmoc (9-fluorenylmethoxycarbonyl)-strategy with HBTU (2-(1H-benzotriazol-1-yl) 1,1,3,3,tetramethyluronium hexafluorophosphat)-activation (0.1 mmol small-scale cycles) on the Applied Biosystems (Foster City, Calif.) peptide synthesizer Model 433A. Preloaded PEG-PS (polyethylenglycol polysterene) resins (0.15-0.2 mmol/g loading) (per Septive Biosystems, Warrington, UK) were used as solid phase to build up the peptides. Chemicals were purchased from Applied Biosystems. Coupling of amino acids was confirmed by conductivity monitoring in a feedback control system. One cysteine residue was added to each peptide at the N- or C-terminus to facilitate coupling of the peptides to carriers. Peptides were cleaved from the resins with a mixture of: 250 µl distilled water, 250 µl Triisopropylsilan (Flukan, Buchs, Switzerland), 9.5 ml TFA for 2 h and precipitated in tert-Butylmethylether (Flukan, Buchs, Switzerland). The identitiy of the peptides was checked by mass-spectrometry and they were purified to >90% purity by preparative HPLC (PiChem, Graz; Austria) (Focke M, Mahler V, Ball T., Sperr. W R, Majlesi Y, Valent P, Kraft D, Valenta R. Nonanaphylactic synthetic peptides derived from B cell epitopes of the major grass pollen allergen, Phl p 1, for allergy vaccination. FASEB J. 2001, 15: 2042-2044.

The allergenic activity of the Phl p 2-derived peptides was evaluated by comparing the IgE-reactivity of complete rPhl p 2 with the peptides by dot blot analysis (FIG. 1). Nitrocellulose-dotted Phl p 2-derived peptides (P1-P3), an immunologically unrelated major grass pollen allergen, rPhl p 5 (Vrtala S, Sperr W R, Reimitzer I, van Ree R, Laffer S, Müller W D, Valent P. Lechner K, Rumpold H, Kraft D, Scheiner O, Valenta R. cDNA cloning of a major allergen from timothy grass (*Phleum pratense*) pollen; characterization of the recombinant Phl p V allergen. J. Immunol. 1993, 151: 4773-4781), and for control purposes, human serum albumin as well as a control peptide were exposed to sera from grass pollen allergic patients and to serum from a non-allergic individual.

Bound IgE antibodies were detected as described previously (Valenta R. Duchene M, Ebner C, Valent P, Sillaber C, Deviller P, Ferreira F, Tejkl M, Edelmann H, Kraft D, Scheiner O. Profilins constitute a novel family of functional plant pan-allergens. J. Exp. Med. 1992, 175: 377-385). Sera from all 35 grass pollen allergic patients showed IgE reactivity to nitrocellulose-dotted rPhl p 2 but no serum reacted with any of the three Phl p 2-derived peptides (FIG. 1). Serum from the non-allergic individual displayed no IgE reactivity to any of the peptides or proteins.

B. Characterization of the Recombinant Phl p 2 Mosaic Protein

A recombinant Phl p 2 mosaic protein was obtained by recombination of the three Phl p 2-derived peptides in altered sequence. This mosaic protein was created under the assumption that recombination of three non-allergenic Phl p 2 fragments in altered order will deliver a mosaic protein with disrupted three-dimensional structure and consequently reduced allergenic activity. In addition it was expected that the mosaic protein will exhibit better immunogenicity compared to the individual smaller peptide units and preserve the entire primary amino acid sequence of Phl p 2 thus containing the relevant T cell epitopes of Phl p 2.

FIG. 2 shows the assembly of the three peptides in the natural Phl p 2 allergen compared to that of the Phl p 2 mosaic protein. In order to compare the two proteins a recombinant Phl p 2 containing: a C-terminal hexahistidine tail (SEQ ID NO: 23) and a recombinant Phl p 2 mosaic protein was produced which also contained a C-terminal hexahistidine tail (SEQ ID NO: 23) (FIG. 2) to allow the purification of both proteins by Nickel affinity chromatography (Quailed, Hilden, Germany).

The recombinant Phl p 2 mosaic was constructed by PCR-based gene amplification of codas coding for the three peptides in the order shown in FIG. 2 using the primers displayed in FIG. 3 and the Phl p 2-encoding cDNA (Dolecek C, Vrtala S, Laffer S, Steinberger P, Kraft D, Scheiner O, Valenta R. Molecular characterization of Phl p II, a major timothy grass (*Phleum pratense*) pollen allergen. FEBS Lett. 1993, 335: 299-304) as template as described (Linhart B. Jahn-Schmid B, Verdino P, Keller W, Ebner C, Kraft D, Valenta R. Combination vaccines for the treatment of grass pollen allergy consisting of genetically engineered hybrid molecules with increased immunogenicity. FASEB J. 2002, 16: 1301-1303).

FIG. 4 shows the DNA and deduced amino acid sequence of the recombinant Phl p 2 mosaic protein. The his-tagged mosaic protein is encoded by a DNA of 309 by coding for a protein with a calculated molecular of 11769 Da almost identical to the his-tagged recombinant Phl p 2 allergen (11784 Da).

The cDNA coding for a his-tagged rPhl p 2 allergen was obtained by PCR using a combination of the 5' primer P2/1 (SEQ ID NO:6) and the 3' primer P2/7 (SEQ ID NO:12): CGC GAA TTC TCA GTG GTG GTG GTG GTG GTG CTC TTC TGG CGC GTA GGT GGC and the cDNA coding for Phl p 2 as a template.

The cDNAs coding for the his-tagged Phl p 2 mosaic and the his-tagged Phl p 2 allergen were separately ligated into Nde I/Eco RI cut plasmids pET17b (Novagen). The DNA sequences of the two plasmid constructs was confirmed by sequence analysis and the recombinant proteins were expressed in *Escherichia coli* BL21 (DE3) (Novagen) by induction with 0.5-mM isopropyl-β-thiogalactopyranoside at an optical density at 600 nm of 0.4 in liquid culture (LB, medium containing 100 mg/l ampicillin) for additional 4 hours at 37° C. *E. coli* cells from a 500 ml culture were harvested by centrifugation and prepared for purification under native (rPhl p 2) or denaturing conditions (rPhl p 2 mosaic) according to the manufacturers advice (Quiagen, Hilden, Germany). Protein samples were analyzed for purity by sodium codicil sulfate-polyacrylamide gel electrophoresis (SDS-PAGE) and protein staining (Fling S P, Gregerson D S. Peptide and protein molecular weight determination by electrophoresis using a high-molarity Tris buffer system without urea. Anal. Biochem. 1986, 155:83-88) (FIG. 4).

FIG. 5 shows the purity of the his-tagged recombinant proteins (rPhl p 2: P2; rPhl p 2 mosaic: P2M). Although the two proteins did not show a completely identical migration behavior in the SDS-PAGE, mass spectroscopical analysis performed as described by Niederberger V, Hayek B, Vrtala S, Laffer S, Twardosz A, Vangelista L, Sperr W R, Valent P, Rumpold H, Kraft D, Ehrenberger K, Valenta R, Spitzauer S. Calcium-dependent immunoglobulin E recognition of the apo- and calcium-bound form of a cross-reactive two EF-hand timothy grass pollen allergen, Phl p 7. FASEB J. 1999, 13: 843-856 showed almost identical molecular weights of the two proteins (rPhl p 2: 11775 Da; rPhl p 2 mosaic: 11770 Da) which were in good agreement with the deduced molecular weights including the methionines at their N-terminus (FIG. 6).

C. The rPhl p 2 Mosaic Lacks IgE Reactivity and Allergenic Properties

The IgE binding capacity of purified Phl p 2 mosaic (P2M) was compared with that of Phl p 2 wild-type by dot blot experiments as described for the peptides using sera from twelve timothy grass pollen allergic patients (FIG. 7). Sera from all 12 grass pollen allergic patients contained IgE antibodies against rPhl p 2 but no serum exhibited IgE reactivity to the rPhl p 2 mosaic or the negative control, human serum albumin (FIG. 7). The strongly reduced allergenic activity of the rPhl p 2 mosaic was further demonstrated by basophil histamine release and skin test experiments. Basophils from a grass pollen allergic patient were enriched by dextran sedimentation and exposed to increasing concentrations of purified rPhl p 2 or rPhl p 2 mosaic as described (Valent P, Besemer J, Muhm M, Majdic O; Lechner K, Bettelhei P. Interleukin 3 activates human blood basophils via high-affinity binding sites. Proc. Natl. Acad. Sci. USA 1989, 86: 5542-5546).

Histamine released in the cell free supernatants was determined in triplicates by radioimmunoassay and is expressed as mean percentage of the total histamine content of the cells as described by Valent et al.

Figure 8:
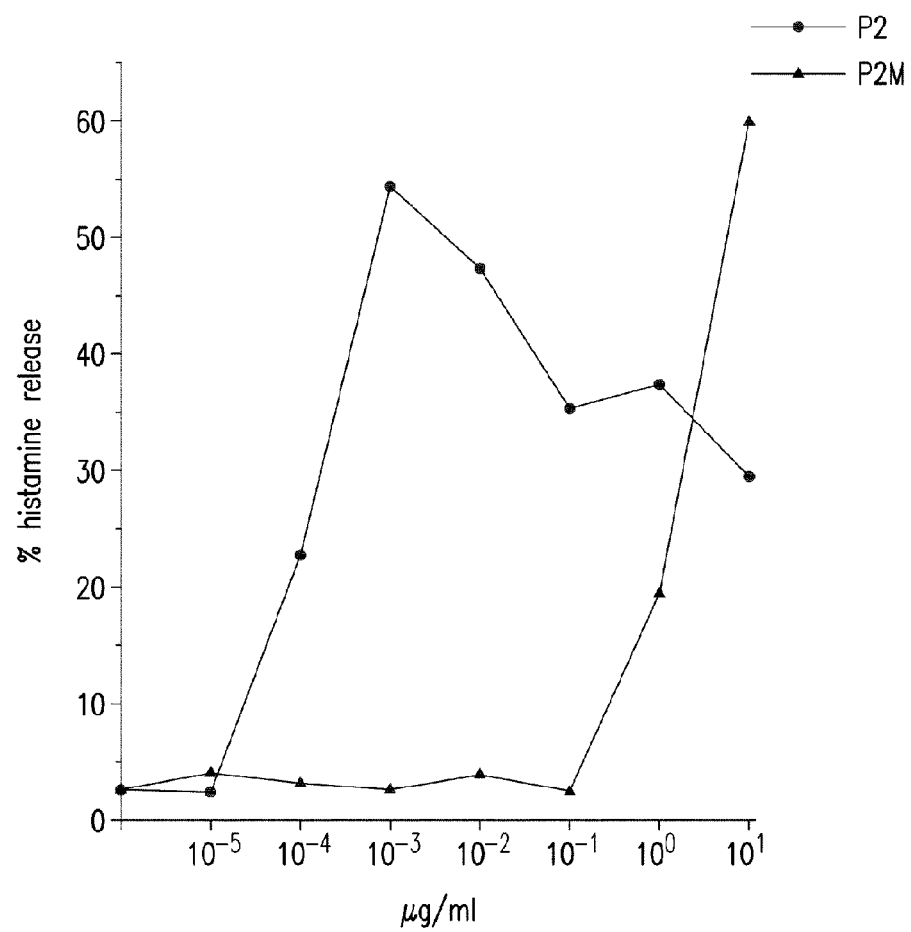
FIG. 8: Reduced allergenic activity of rPhl p 2 mosaic determined by basophil histamine release. Basophils from a grass pollen allergic patient were exposed to increasing concentrations of rPhl p 2 and rPhl p 2 mosaic (x-axis). Histamine release is expressed as percentage of total histamine release on the y-axis.

FIG. 8 shows that the rPhl p 2 mosaic (maximal release between 1 and 10 µg/ml) exhibited a more than 1000 fold reduced allergenic activity compared to the rPhl p 2 allergen (maximal release $10^{-3}$ µg/ml).

The strongly reduced allergenic activity of rPhl p 2 mosaic was confirmed by skin testing in grass pollen allergic patients (FIG. 19-Table 2). SPTs (skin prick tests) were performed on the individuals' forearms. Twenty microliter aliquots containing 5 concentrations of rPhl p 2 and of Phl p 2-derived mosaic P2M (1 µg/ml, 2 µg/ml, 4 µg/ml, 8 µg/ml, 16 µg/ml) were applied. In addition, standardized skin prick solutions (timothy grass pollen extract and histamine) (Allergopharma, Reinbeck, Germany) were tested. Reactions were recorded 20 minutes after SPT by photography and by transferring the ballpoint pen-surrounded wheal area with a scotch tape to paper. The mean wheal diameter (Dm) was calculated by measuring the maximal longitudinal and transversal diameter and dividing their sum by 2 as described by Focke et al., 2001.

rPhl p 2 induced strong wheal reactions already at the lowest concentration tested, i.e., 1 µg/ml, whereas rPhl p 2 mosaic induced only mild wheal reactions at the maximal concentrations tested (i.e., 8-16 µg/ml) thus confirming the reduced allergenic activity of the mosaic protein.

D. Immunization with the rPhl p 2 Mosaic Induces IgG Antibodies that Recognize rPhl p 2 Wild-type and Inhibits Allergic Patients' IgE Binding to Phl p 2

In order to test whether immunization with Phl p 2 mosaic and Phl p 2 mosaic will induce IgG antibodies that react with natural Phl p 2, rabbits were immunized with rPhl p 2 mosaic, KLH-coupled rPhl p 2 mosaic or rPhl p 2 using Freund's adjuvant as described by Focke et al.

Figure 9:
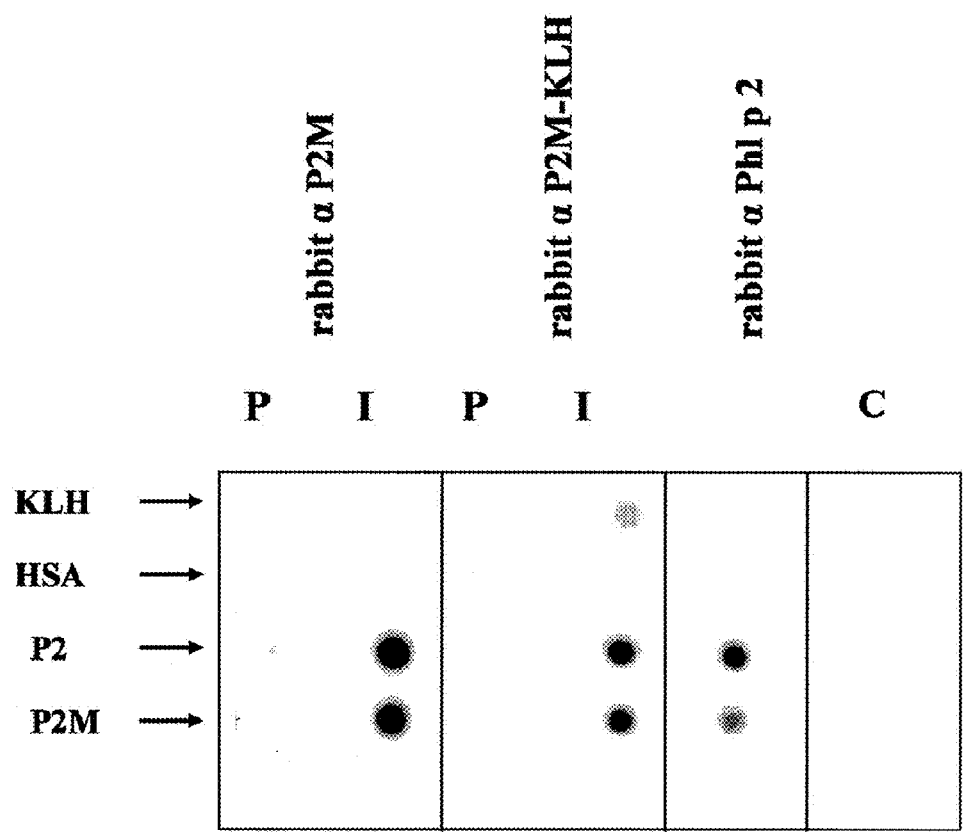
FIG. 9: Rabbit anti-rPhl p 2 mosaic antibodies recognize the rPhl p 2 wild-type allergen. Rabbit antisera raised against the rPhl p 2 mosaic (aP2M), KLH-coupled mosaic (aP2M-KLH) and rPhl p 2 (aPhl p 2) as well as buffer (C) were exposed to dot-blotted KLH, human serum albumin (HSA), rPhl p 2 (P2) and rPhl p 2 mosaic (P2M). Bound rabbit antibodies were detected with $^{125}$I-labeled donkey anti-rabbit IgG and visualized by autoradiography.

The reactivity of rabbit IgG antibodies with rPhl p 2 was studied by dot blot experiments (FIG. 9). Phl p 2 wild-type (P2) as well as the corresponding immunogen Phl p 2 mosaic (P2M) were dotted onto nitrocellulose-strips (1 µg/dot). Nitrocelluloses were exposed to the rabbits preimmune or immune sera (1:500) and bound rabbit antibodies were detected with a 1:1000 diluted $^{125}$I-labeled donkey anti-rabbit antiserum (Amersham Pharmacia Biotech) as described by Valenta et al., 1992.

The rabbit anti-rPhl p 2 mosaic antiserum reacted strongly with the immunogen (rPhl p 2 mosaic) as well as with the rPhl p 2 allergen (FIG. 9). The antibody reactivity was of comparable intensity as that obtained with the antiserum produced by immunization with the KLH-coupled mosaic and stronger than the reactivity induced by immunization with the rPhl p 2 allergen (FIG. 9).

E. Measurement of Blocking Antibodies

It was studied whether IgG antibodies induced by immunization with the rPhl p 2 mosaic inhibit the binding of allergic patients' serum IgE to complete rPhl p 2 by ELISA competition using sera from five grass pollen allergic patients (FIG. 20-Table 3). ELISA plates (Nunc Maxisorp, Rokslide, Denmark) were coated with rPhl p 2 (1 µg/ml) and preincubated either with a 1:100 dilution of each of the anti-Phl p 2 mosaic and anti-Phl p 2 antiserum and, for control purposes, with the corresponding preimmunsera. After washing plates were incubated with 1:3 diluted sera from five Phl p 2-sensitized grass pollen allergic patients and bound IgE antibodies were detected with alkaline phosphate conjugated monoclonal rat anti-human IgE antibody (Pharmingen, San Diego, Calif.), diluted 1:1000. The percentage inhibition of IgE binding achieved by preincubation with the anti-Phl p 2 mosaic and Phl p 2 was calculated as follows: % inhibition of IgE binding=100–$OD_I$/$OD_P$×100. $OD_I$ and $OD_P$ represent the extinctions after preincubation with the rabbits immune and preimmune serum, respectively as described by Focke et al., 2001.

The anti-Phl p 2 mosaic antibodies inhibited the binding of grass pollen allergic patients IgE binding to Phl p 2 (20.93% average inhibition) albeit to a lower degree as was achieved by preincubation with antibodies induced by immunization with the rPhl p 2 allergen (54.73% average inhibition).

The results of the immunization studies thus show that antibodies raised against the rPhl p 2 mosaic recognize the Phl p 2 wild-type allergen and inhibit allergic patients IgE recognition of Phl p 2.

Example 2

Mosaic Derivatives of the Bet v 1 Birch Pollen Allergen

A. Materials and Methods
Patients' Sera, Plasmids and Recombinant Allergen:

Patients suffering from birch pollen allergy were characterized by case history and positive skin prick testing. Serum IgE Abs specific to birch pollen extract and rBet v 1 were determined by immuno CAP measurements (Phadia, Uppsala, Sweden) as described[3] (Table 6, below). Control sera were taken from two non-allergic volunteers.

The plasmid pET 17b (Novagen Inc., Madison, Wis., USA), used for the expression of rBet v1 and of the rBet v 1 derivatives is as described by Hoffman-Sommergruber et al.[17] The recombinant *Escherichia coli*-expressed (BL 21-DE3) (Stratagene, La Jolla, Calif., USA) birch pollen allergen Bet v 1 (batch #21), was obtained from Biomay (Vienna, Austria).
Monoclonal Antibodies:

Bip 1, a monoclonal antibody with specificity for the major birch pollen allergen Bet v 1, was previously described by Laffer et al.[18] The mouse mAb 4A6 was raised against purified recombinant birch pollen profiling (see Widemann et al.[19]). Anti-IgE mAb E-124.2.8 was purchased from Immunotech (Marseille, France).

Mouse IgG mAbs against peptide 2 (mAb#2) (aa 30-59) and against peptide 6 (mAb#12) (aa 74-104) of Bet v 1 were obtained by immunization of mice using KLH-coupled synthetic peptides (peptide 2: LFPKVAPQAISSVENIEGNGG-PPTIKKISF (SEQ ID NO: 21); peptide 6: EDVHTN-FKYNYSVIEGGPIGDTLEKISNEIK (SEQ ID NO: 22).
Construction of Hypoallergenic Bet v 1 Derivatives:

Based on the Bet v 1 sequence described by Mothes et al.[2], synthetic genes were generated giving rise to three different recombinant Bet v 1 derivatives: Restructured Bet v 1 #1 (Bet v 1-rs1) comprising amino acids 75-160+1-74, Restructured Bet v 1 #2 (Bet v 1 rs2) comprising amino acids 110-160+1-109, and Bet v 1 mosaic comprising amino acids 110-160+60-109+1-59 (FIG. 10A).

The synthetic genes of each of the recombinant Bet v 1 derivatives were cloned into the pET17b (Novagen Inc., Madison, Wis., USA) cloning vector via NdeI and EcoR1 restriction sites. The correct sequence of the derivative molecules was confirmed by double stranded DNA sequencing (Eurofins Medigenomix GmbH, Ebersberg, ATG Biosynthetics GmbH, Merzhausen, Germany).

Expression and Purification of the Recombinant Hypoallergenic Bet v 1 Derivatives:

Batch fermentation of *E. coli* BL 21 (DE3) transformed with pET-17b-Bet v 1-rs1, -rs2 or mosaic was carried out at 37° C. in a 10 L fermenter (New Brunswick, Bioflow 3000) in LB medium with the addition of 0.05% (v/v) glycerol, 0.25% (w/v) $MgSO_4$. 7 $H_2O$, and 0.18% $Na_2HPO_4$. 2 $H_2O$ for 8 h at 37° C. until a cell density ($0D_{600nm}$) of 0.4 to 0.6 was reached. Protein expression was induced by adding 0.5 mM isopropyl-B-thiogalactopyranoside (IPTG) (Calbiochem, Merck, Darmstadt, Germany). Recombinant proteins were produced and characterized as follows:

Inclusion bodies were isolated from the cells using lysozyme (0.1 mg/g cell wet weight) (Sigma-Aldrich, St. Louis, Mo., USA) and repetitive freezing and thawing in buffer I (50 mM Tris base, 1 mM EDTA and 0.1% Triton X-100) for Bet v 1-rs1 and Bet v 1-mosaic, or buffer II (25 mM $NaH_2PO_4$, pH 7.4 and 0.1% Triton X-100) for Bet v 1-rs 2 (5 mL/g cell wet weight). NaCl was added to a final concentration of 200 mM, and the suspensions were centrifuged (10000 g for 30 min. at 4° C.) leaving the proteins containing inclusion bodies in the pellet.

Bet v 1-rs1 and Bet v 1-rs2 pellets were washed with 1% Triton X-100, 2 mM EDTA, 2 mM B-mercaptoethanol, 20 mM Tris/HCl pH 8.0 (3 times) and afterwards with 50% ethanol, 20 mM Tris/HCl pH 8.0 (2 times). The Bet v 1-mosaic pellet was washed once with 1% Triton X-100, 20 mM $NaH_2PO_4$ pH 7.4 and once with 25% ethanol, 20 mM $NaH_2PO_4$ pH 7.0. Inclusion bodies were suspended and stirred for 30 min in buffer A (6 M urea, 10 mM Tris/HCl, 1 mM EDTA, pH 7.0) in case of Bet v 1-rs1, or in buffer B (5 M urea in 20 mM sodium acetate buffer, pH 5.0) in case of Bet v 1-rs2 and mosaic. The suspensions were centrifuged (10000 g for 30 min. at 4° C.) and the final supernatant used for purification.

Recombinant Bet v 1-rs1 was first purified by anion exchange chromatography (AIEC) on a Q-Sepharose FF column (GE Healthcare, UK Limited) by applying a linear gradient from 0-250 mM NaCl in buffer A. Fractions containing Bet v 1-rs1 were dialyzed against buffer C (6 M urea, 20 mM $NaH_2PO_4$, 1.5 M NaCl, pH 4.5) and subjected to hydrophobic interaction chromatography (HIC) using a Phenyl Sepharose FF column (GE Healthcare, UK Limited) equilibrated with buffer C. Purified Bet v 1-rs1 was eluted with a linear gradient from 0% to 100% buffer D (6 M urea, 20 mM Tris base, pH 9.3) and pure fractions were dialyzed first against 6M urea and then against 1 mM acetic acid. Finally, the protein was subjected to 0.2 μm filtration and stored at −20° C.

Recombinant Bet v 1-rs2 and -mosaic were purified by cation exchange chromatography (CIEC) using a SP-Sepharose FF column (GE Healthcare, UK Limited) equilibrated with buffer B and eluted with a linear gradient from 0-400 mM NaCl in the same buffer. To the fractions containing Bet v 1-rs2 NaCl was added to a final concentration of 1.7 M. Protein was centrifuged (10000 g for 30 min at 4° C.) and the supernatant subjected to hydrophobic interaction chromatography (HIC) using a Phenyl Sepharose FF column (GE Healthcare, UK Limited), equilibrated with buffer E (6 M urea, 1.7 M NaCl in a 20 mM sodium acetate buffer, pH 5.0). Bet v 1-rs2 was then eluted with a linear gradient from 1.7-0 M NaCl in buffer E and fractions containing >90% pure rBet v 1-rs2 were dialyzed against buffer F (6 M Urea, 20 mM $NaH_2PO_4$ pH 7.0) and subjected to anion exchange chromatography (AIEC) using a Q-Sepharose FF column (GE Healthcare, UK Limited) equilibrated with the buffer F. To the fractions containing Bet v 1-mosaic urea and NaCl were added to a final concentration of 6.5 M and 3.5 M respectively. The protein was centrifuged (10000 g for 30 min at 4° C.) and the supernatant subjected to hydrophobic interaction chromatography (HIC) using a Phenyl Sepharose FF column (GE Healthcare, UK Limited), equilibrated buffer G (6.5 M urea, 3.5 M NaCl in a 20 mM sodium acetate buffer, pH 5.0). Bet v 1-mosaic was eluted with a linear gradient from 3.5-0 M NaCl in buffer G.

Finally, Bet v 1-rs2 or -mosaic fractions containing >90% purity were pooled, dialyzed against 5 mM $NaH_2PO_4$ pH 7.4 and subjected to 0.2 μm filtration and stored at −20° C.

Purified rBet v 1 and each of the rBet v 1 derivatives (5 μg protein/slot) were resolved on 12.5% sodium dodecyl sulfate-polyacrylamide gel electrophoresis (SDS-PAGE) in the presence or absence of 2-mercaptoethanol[36]. Proteins were visualized by staining with Coomassie brilliant blue. The presence of endotoxin was determined in a *limulus amebocyte* lysate (LAL) chromogenic assay (QCL-1000$^R$ Chromogenic LAL Endpoint Assay, Bio-Whittaker, Walkersville, USA).

Laser desorption mass spectra of the proteins were acquired in a linear mode with a MALDI-ToF instrument (Microflex, Bruker, Billerica, Mass., USA). Samples were dissolved in 10% acetonitrile (0.1% trifluoroacetic acid), and sinapinic acid (dissolved in 60% acetonitrile, 0.1% trifluoroacetic acid) was used as a matrix. For sample preparation a 1:1 mixture of protein and matrix solution was deposited onto the target and air-dried.

CD spectra were acquired on a JASCO (Tokyo, Japan) J-810 spectropolarimeter. CD measurements were performed with purified rBet v 1 and rBet v 1 derivatives at room temperature, at protein concentrations of 0.1 mg/ml using a rectangular quartz cuvette with 0.1-cm path length. Far ultraviolet (UV) spectra were recorded in the wavelength ranges between 190 and 260 nm with a resolution of 0.5 nm at a scan speed of 50 nm/min and resulted from averaging of three measurements. The final spectra were baseline-corrected and results were expressed as the mean residue ellipticity (Θ) at a given wavelength. The secondary structure content of rBet v 1 and Bet v 1 derivative molecules was calculated using the secondary structure estimation program CDSSTR[37].

For gel filtration rBet v 1 derivatives which had been stored for 22 months at −20° C. were loaded onto a Superdex™ 200 5/150 GL column (GE Healthcare, Sweden), equilibrated with 10 mM sodium phosphate buffer pH 7.4 containing 150 mM NaCl. Bovine y-globulin (158 kDa), Chicken Ovalbumin (44 kDa) and Horse Myoglobin (17 kDa) from Gel Filtration Standard (BIO-RAD, Richmond, Calif.) were used for calibration. Recombinant Bet v 1 which also had been stored for 22 months at −20° C. was applied to the column under the same conditions to show the elution characteristics of the wild-type protein. The flow rate was 0.3 ml/min. The molecular masses were calculated using linear regression of the logarithm of molecular mass versus elution volumes derived from UV measurements at 280 nm. Recombinant Bet v 1 derivatives were reapplied to gelfiltration with the Superdex™ 200 5/150 GL column to check the stability of the proteins after further storage at −20° C.

Detection of IgG Binding Capacity of rBet v 1 and rBet v 1 Derivatives:

Purified recombinant Bet v 1 and rBet v 1 derivative molecules were tested for reactivity with specific antibodies. Five µg of each protein/slot was separated by SDS-PAGE[20] and blotted onto nitrocellulose[21]. Nitrocellulose blotted proteins were incubated either with a 1:2000 dilution of a rabbit anti-rBet v 1 or the corresponding pre-immune serum, or with a 1:1000 dilution of mouse monoclonal IgG antibodies. Bound IgG antibodies were detected with a 1:1000 dilution of $^{125}$I-labeled goat anti-rabbit antibodies or with a 1:1000 dilution of $^{125}$I-labeled goat anti-mouse antibodies (NEN Life Science Products, Inc., Boston, Mass., USA) and visualized by autoradiography[9].

IgE Reactivity of Dot-Blotted rBet v 1 and Bet v 1 Derivatives:

Two µL aliquots containing 1 µg of purified rBet v 1, each of the rBet v 1 derivatives, bovine serum albumin (BSA) and human serum albumin (HSA) (negative control proteins) (Roth, Karlsruhe, Germany) were dotted onto nitrocellulose. Nitrocellulose strips were incubated with sera from nineteen birch pollen allergic individuals, two non-allergic individuals or buffer without addition of serum. Bound IgE antibodies were detected with a 1:20 dilution of $^{125}$I-labeled anti-human IgE antibodies (RAST RIA, Demeditec Diagnostics, Germany). The presence of rBet v 1 and rBet v 1 derivatives on the nitrocellulose membrane was shown with rabbit anti-rBet v 1 antibodies, which were detected with 1:1000 dilution of $^{125}$I-labeled donkey anti-rabbit antibodies (NEN Life Science Products, Inc., Boston, Mass., USA).

Immunization of Rabbits and Determination of IgG Antibody Levels:

Rabbits were immunized twice, at study day 0 and at day 28, with 200 µg of purified rBet v 1, rBet v 1-rs1, rBet v 1-rs2, or rBet v 1-mosaic initially adsorbed to CFA (Complete Freund's adjuvant) and followed by booster injection using IFA (Incomplete Freund's adjuvant), or with 100 µg of the proteins adsorbed to Al(OH)$_3$. Pre-immune sera were obtained from the rabbits before immunization (Charles River Breeding Laboratories, Kisslegg, Germany).

ELISA plates (Greiner, Kremsmünster, Austria) were coated with rBet v 1, rBet v 1 derivatives or BSA (negative control) (5 µg/ml diluted in PBS) at 4° C. overnight. After washing three times with PBS-T (PBS+0.05% Tween 20) and blocking with 2% bovine serum albumin (BSA) (Roth, Karlsruhe, Germany) in PBS-T for 6 hours, plates were incubated either with rabbit antisera in five different dilutions (PBS-T, 0.5 w/vol % BSA) (1:1000, 1:5000, 1:10000, 1:100000 and 1:1000000) for antibodies generated with CFA adsorbed proteins or in eight different dilutions (1:500, 1:1000, 1:2000, 1:4000, 1:8000, 1:16000, 1:32000 and 1:64000) for antibodies induced with Al(OH)$_3$ adsorbed proteins. Controls were performed with normal rabbit antibodies. Plates were washed five times with PBS-T and bound rabbit IgG antibodies were detected with a 1:1000 diluted anti-rabbit IgG Horseradish Peroxidase linked whole antibody from donkey (GE Healthcare, UK Limited) for 1 hour at 37° C. and 4° C. After washing with PBS-T (5 times) the color development was performed by addition of staining solution ABTS (2,2'-Azino-bis(3-ethylbenzthiazoline-6-sulfonic acid)diammonium salt; Sigma-Aldrich, St. Louis, Mo., USA) (100 µl/well). The optical density was measured using an ELISA Reader (Dynatech, Denkendorf, Germany) at 405 nm.

Allergenic Activity of Allergen Derivatives:

The allergenic activity of allergen derivatives was compared with that of the Bet v 1 wild-type allergen using CD203c assays as follows:

Heparinized peripheral blood samples were obtained from birch pollen allergic individuals after informed consent was given. Blood aliquots (100 µl) from six patients were incubated (unique) with serial dilutions (0.005 to 50 pM) of rBet v1, an equimolar mix of the rBet v 1 fragments (F1+F2), or rBet v 1-rs 1 for 15 minutes at 37° C. Blood aliquots (100 µl) from additional four patients were incubated (unique) with serial dilutions (0.005 to 50 pM) of rBet v1, rBet v 1-rs1, rBet v 1-rs2, or rBet v 1-mosaic as described above. A monoclonal anti-IgE antibody E-124.2.8 (1 µg/ml) (Immunotech, Marseille, France) and PBS (control buffer) were used as controls. Thereafter, samples were washed in PBS containing 20 mM EDTA (Gibco, Carlsbad, Calif., USA) and cells were incubated with 10 µl of PE-conjugated CD203c mAb 97A6 (Immunotech, Marseille, France) for 15 minutes at room temperature. After erythrocyte lysis using FACS™ Lysing Solution (Becton Dickinson Biosciences, San Jose, Calif., USA), cells were washed and resuspended in PBS and then analyzed by two-color flow cytometry on a FACSScan (Becton Dickinson Biosciences, San Jose, Calif., USA) using Flowjo Software (Tree Star Inc., Ashland, Oreg., USA). Anti-IgE-induced up-regulation of CD203c was calculated from mean fluorescence intensities (MFIs) obtained with stimulated ($MFI_{stim}$) and unstimulated ($MFI_{control}$) cells, and is expressed as stimulation index ($MFI_{stim}$: $MFI_{control}$)[3]. Three patients (FIG. 15) were tested in triplicates to analyze the reproducibility of the assay. For those patients results are shown as mean values of triplicate determinations with SD.

Inhibition of Allergic Patients' IgE Binding to Bet v 1 by IgG Antibodies:

The inhibition of allergic patients' IgE binding to Bet v 1 by IgG antibodies was performed using an ELISA competition assay as follows:

ELISA plates (Greiner, Kremsmünster, Austria) were coated with 100 µl of rBet v 1 (5 µg/ml diluted in PBS) overnight at 4° C. Plates were blocked with 2% bovine serum albumin (BSA) (Roth, Karlsruhe, Germany) in PBS-T (PBS 0.05% Tween 20) for 6 hours at 4° C. overnight and then preincubated overnight at 4° C. with 1:50 dilutions (in PBS 0.5% BSA/0.05% Tween) of the rabbit sera anti-rBet v 1, anti-rBet v 1-rs1, anti-rBet v 1-rs2 or anti-rBet v 1-mosaic raised with CFA, or 1:10 dilutions for rabbit sera raised with Al(OH)$_3$, and for control purposes by using the corresponding rabbit pre-immune sera. Plates were washed three times with PBS-T and incubated with 1:10 diluted sera from 18 birch pollen allergic patients sensitized to Bet v 1. Bound human IgE antibodies were detected using a 1:2500 diluted AP-conjugated (alkaline phosphatase) mouse monoclonal anti-human IgE antibody (BD Pharmingen, San Diego, Calif., USA). Color development was performed by addition of staining solution ABTS (2,2'-Azino-bis(3-ethylbenzthiazoline-6-sulfonic acid)diammonium salt; Sigma-Aldrich, St. Louis, Mo., USA) (100 µl/well) and the optical density was measured in an ELISA Reader (Dynatech, Denkendorf, Germany) at 405 nm. The percentage of inhibition of IgE-binding was calculated using the OD values obtained, as follows: percent inhibition of IgE binding=100−(ODs/ODp)×100. ODs, extinction coefficient after preincubation with the rabbit serum. ODp, extinction coefficient after preincubation with the pre-immune serum.

B. Rational Construction of Hypoallergenic rBet v 1 Derivatives

It has been shown that two recombinant fragments of Bet v 1 comprising amino acids 1-74 and 75-160 preserved the Bet v 1-specific T cell epitopes but exhibited an approximately 100 fold reduced allergenic activity compared to rBet v 1 as shown in vitro by basophil activation testing and in several in vivo provocation studies[9, 22-25]. Each of these fragments contains a peptide defined by two monoclonal antibodies mAb#2 (aa 30-59) and mAb#12 (aa 74-104) which induced Bet v 1-specific IgG antibodies inhibiting the binding of birch pollen allergic patients IgE to Bet v 1[26] (FIG. 10A). The first Bet v 1 derivative, designated Bet v 1-rs1, was made by re-assembling the hypoallergenic fragments aa 1-74 and aa 75-160 within one molecule as a tail-to-head construct as described for a Phl p 12 derivative[27] (FIG. 10A). The second Bet v 1 derivative, designated Bet v 1-rs2, was prepared by re-assembling aa 1-109 which contains three peptides (P2: aa 30-59; P3: aa 50-79; and P6: aa 74-104) that had induced strong blocking IgG antibody responses against Bet v 1[26] at the C-terminus and a portion comprising aa 110-160 at the N-terminus. Because of the possibility that the fragment aa 1-109 might regain allergenic activity, it was broken into two pieces, aa 60-109 containing P6 and aa 1-59 containing P2, and a mosaic was constructed from these pieces. This mosaic, designated Bet v 1-mosaic, is composed of Bet v 1 portions aa 110-160, aa 60-109 and aa 1-59 from the N- to the C-terminus (FIG. 10A).

C. Characterization of the Recombinant Bet v 1 Derivatives

Figure 10B:
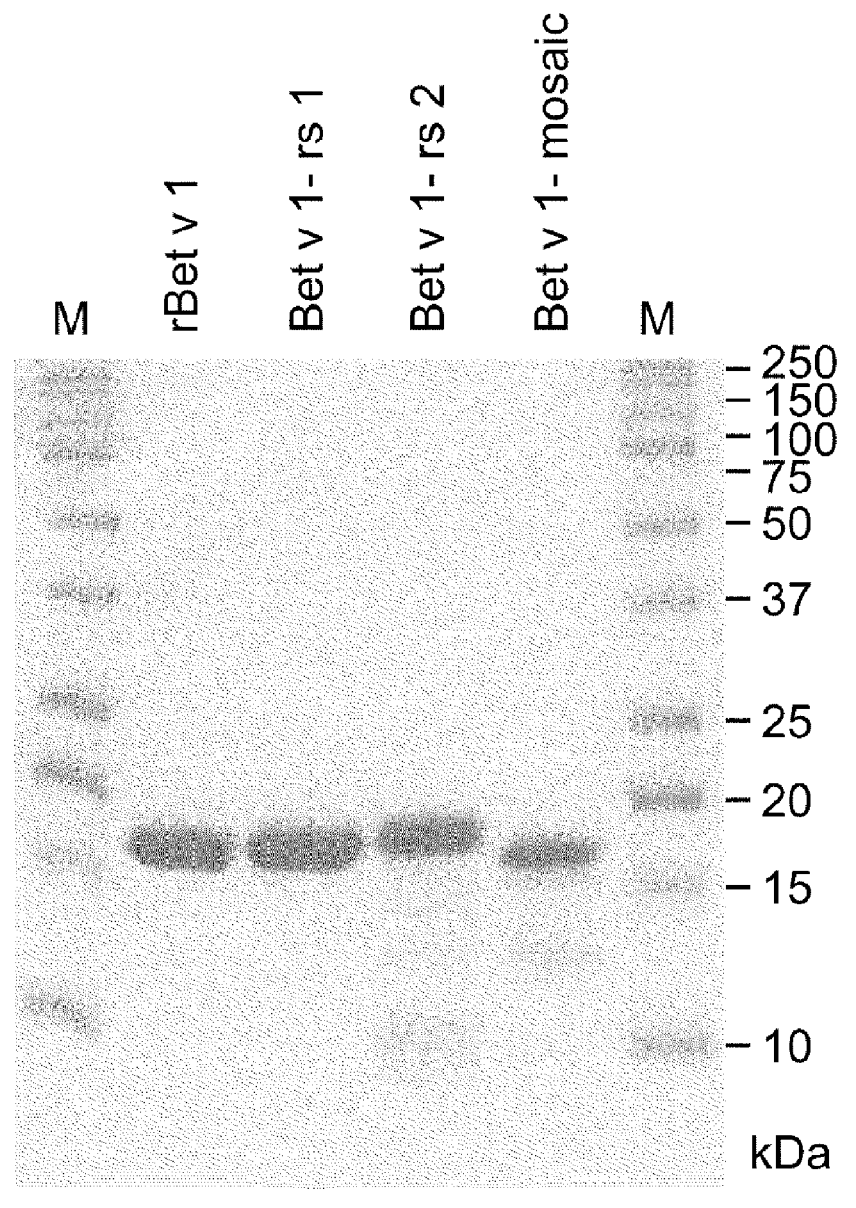

High level expression of the recombinant proteins yielding more than 20% of the total *E. coli* proteins was obtained. Each of the recombinant proteins could be purified from the inclusion body fraction of the bacteria via several chromatography steps to more than 90% purity (FIGS. 10B and 14). When the proteins were analyzed by gel filtration after 22 and 23 months of storage at −20° C., rBet v 1 occurred as monomer (FIG. 14A). Bet v 1-rs2 and Bet v 1-mosaic appeared as stable peaks which may correspond to monomers with higher hydrodynamic radius due to their unfolded condition or to dimers (FIG. 14B, C). Bet v 1-rs1 showed signs of degradation (FIG. 14D). The calculated mass for rBet v 1 and the three derivatives without methionine was (17439.6 Da) which corresponds with mass determined by MALDI-TOF analysis (i.e., Bet v 1-rs1: 17420.3 Da; Bet v 1-rs2: 17421.6 Da; Bet v 1-mosaic: 17452.5 Da; Bet v 1: 17381.6 Da) (data not shown). In contrast to rBet v 1, which exhibited the typical fold of a mixed α helical and β sheet containing protein, all three rBet v 1 derivatives were unfolded in CD analysis (data not shown).

Figure 11A:
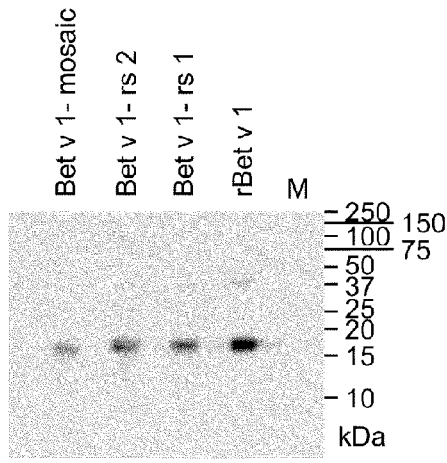
FIG. 11: IgG reactivity of rBet v 1 and rBet v 1 derivatives with Bet v 1-specific antibodies. Nitrocellulose blotted rBet v 1 and rBet v 1 derivatives were probed with rabbit anti-Bet v 1 antibodies (raBet v 1) (A), mAb Bip 1 (B), mAb#2 (C) or mAb#12 (D). Molecular weights are displayed on the right margins in kilo Daltons (kDa).
Figure 11B:
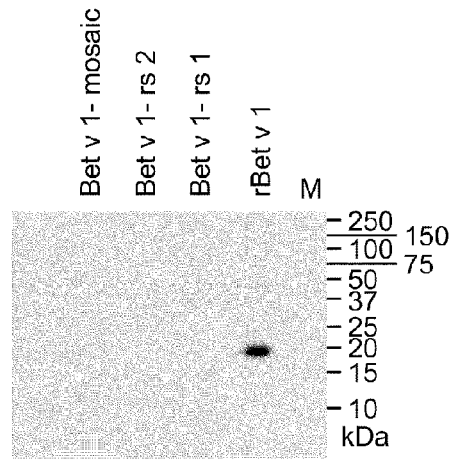
Figure 11C:
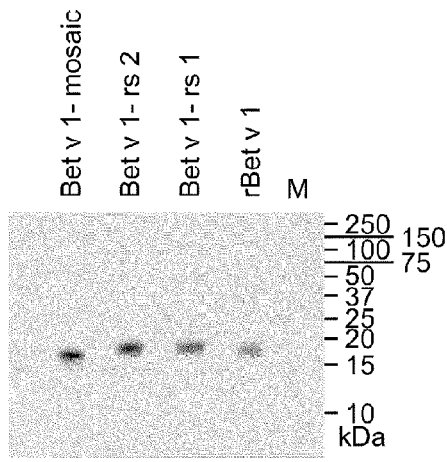
Figure 11D:
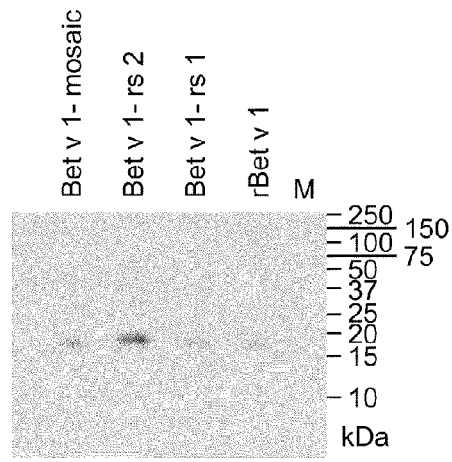

Next, Bet v 1-specific antibody probes were used to test IgG reactivity of the Bet v 1 derivatives. Nitrocellulose-blotted rBet v 1 and rBet v 1 derivatives reacted with the polyclonal rabbit antibodies that had been raised against rBet v 1 (FIG. 11A). Interestingly, the monoclonal antibody Bip 1 which recognizes conformational epitopes of Bet v 1 reacted only with the folded rBet v 1 wild type protein but not with the unfolded rBet v 1 derivatives (FIG. 11B). The mAbs specific for P2 (mAb#2) (aa 30-59) and for P6 (mAb#12) (aa 74-104) reacted with rBet v 1 and each of the three rBet v 1 derivatives (FIG. 11C-D). The rabbit's pre-immune serum and an isotype-matched mouse monoclonal antibody without specificity for Bet v 1 did not show any binding (data not shown).

D. The Bet v 1 Mosaics Lack IgE Reactivity and Allergenic Properties

Figure 12:
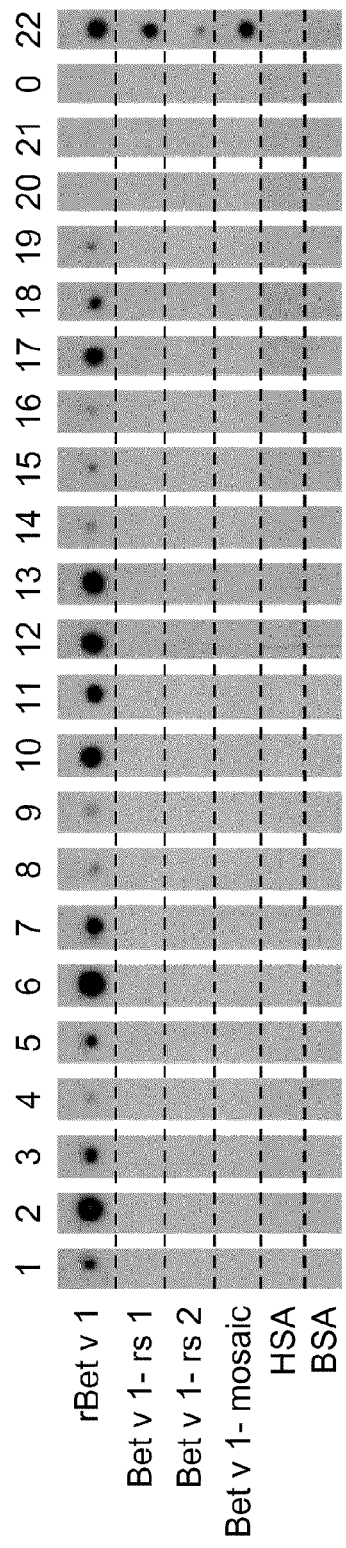
FIG. 12: IgE-reactivity of rBet v 1 and rBet v 1derivatives. Nitrocellulose-dotted rBet v 1, rBet v 1-rs1, rBet v 1-rs2, rBet v 1-mosaic, HSA and BSA were exposed to sera from birch pollen allergic patients (1-19), non-allergic individuals (20-21), buffer (O) or anti-rBet v 1 antibodies (22). Bound IgE and rabbit IgG antibodies were detected and visualized by autoradiography.

None of the 19 birch pollen allergic patients tested exhibited any detectable IgE reactivity to the rBet v 1 derivatives whereas they showed IgE-binding to rBet v 1 (FIG. 12, Patients 1-19). No IgE reactivity to the control proteins HSA and BSA was found. Serum IgE from non-allergic individuals and buffer showed no reactivity to any of the proteins (FIG. 12, patients 20-21, 0). The presence of rBet v 1 and rBet v 1 derivatives on the membrane was confirmed by testing with rabbit anti-rBet v 1 antibodies (FIG. 12, patient 22).

Figure 13A:
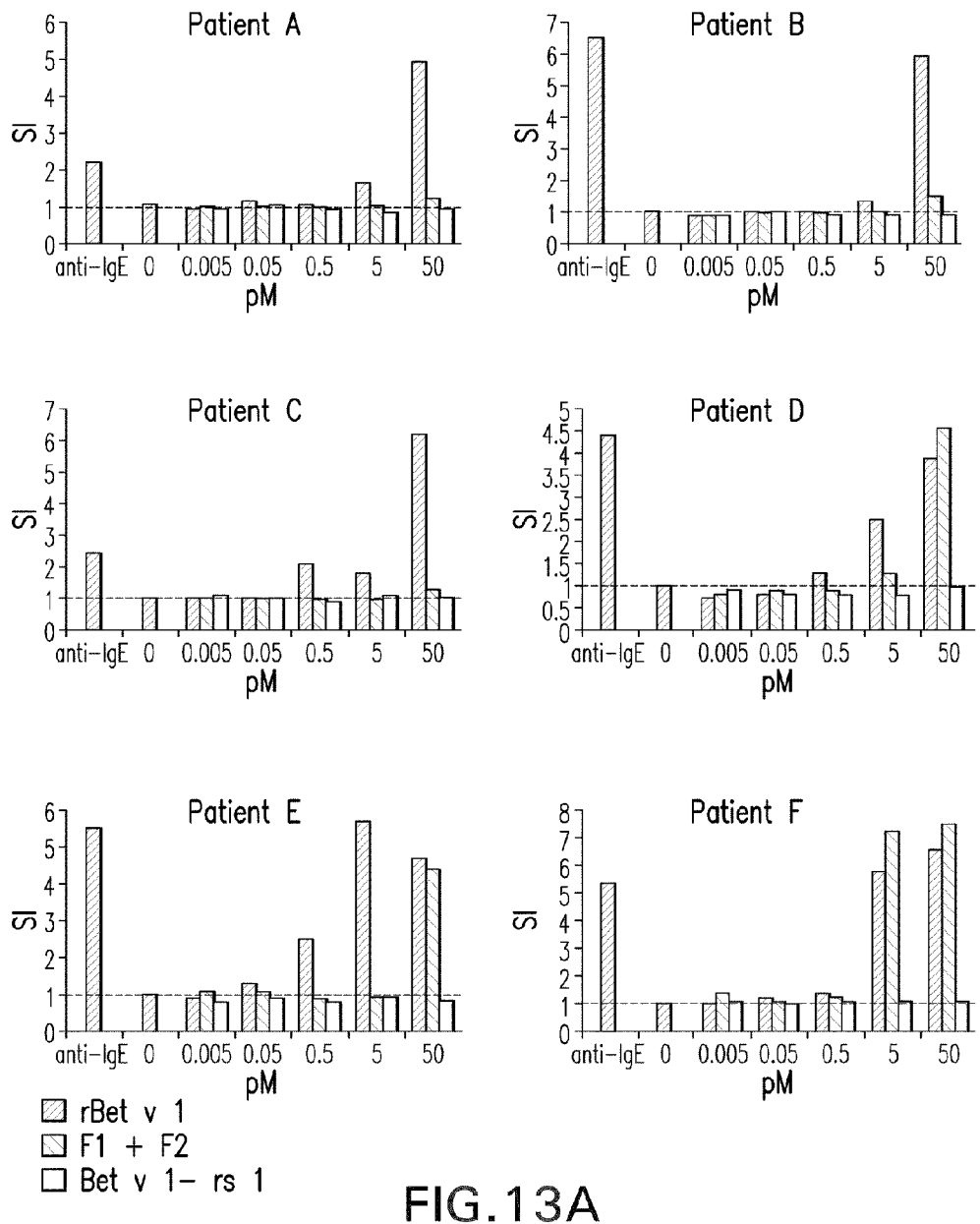
FIG. 13: Allergenic activity of rBet v 1 and rBet v 1 derivatives as determined by CD203c up-regulation. (A) Blood samples from birch-allergic patients (A-F) were exposed to increasing concentrations (0.005 to 50 pM) of rBet v 1, an equimolar mixture of rBet v 1 fragments (F1+F2) or rBet v 1-rs1 (x-axes) and in additional patients (G-J) (B) with rBet v 1, rBet v 1-rs1, rBet v 1-rs2, rBet v 1-mosaic (x-axes). Anti-IgE served as a positive control. The stimulation indices (SI) (y-axis) reflect the up-regulation of CD203c expression compared to buffer (O).
Figure 13B:
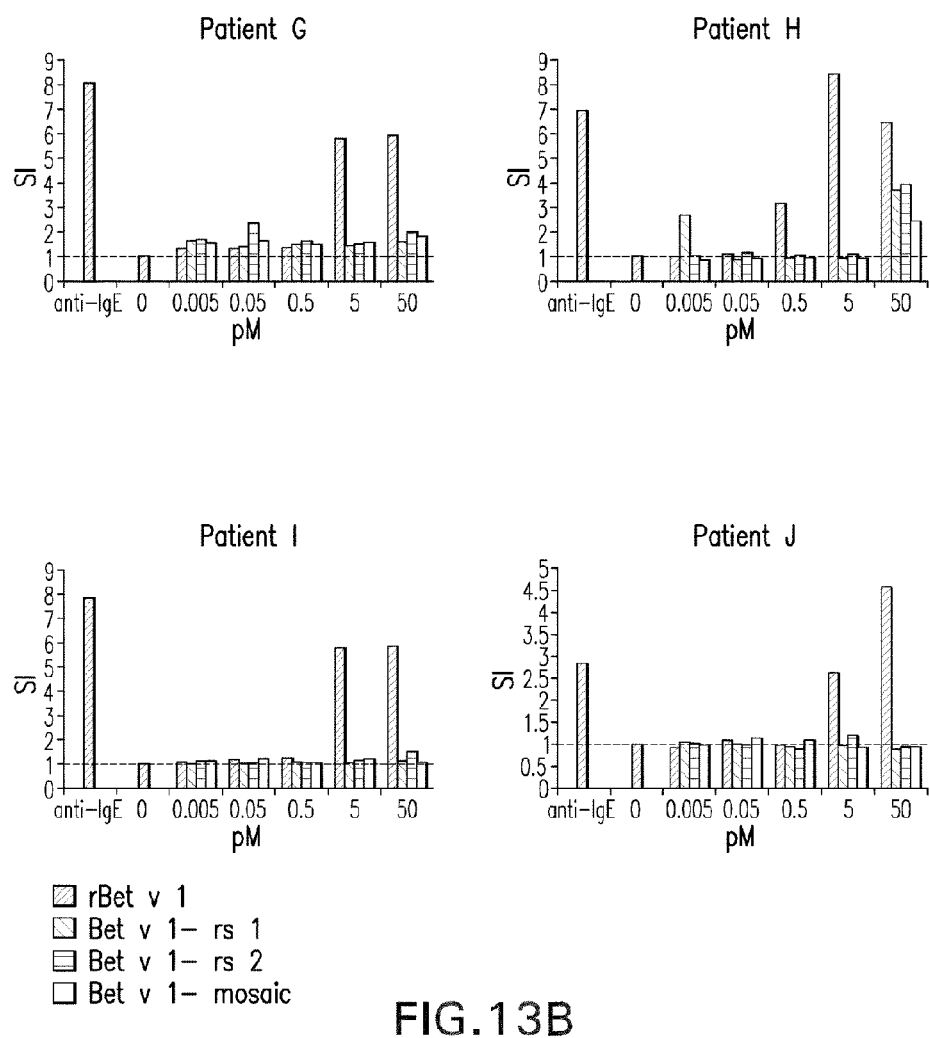
Figure 15:
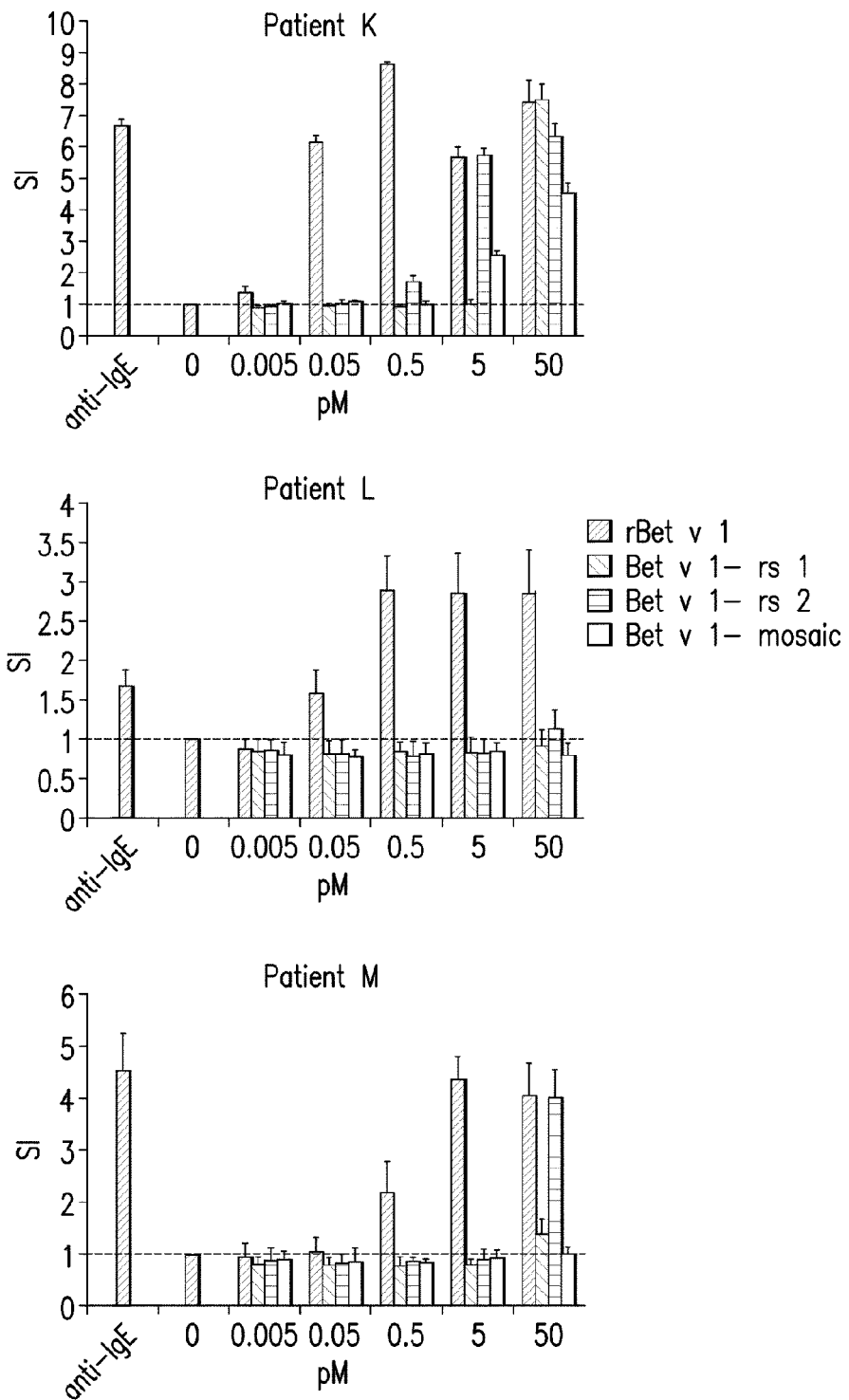
FIG. 15: Allergenic activity of rBet v 1 and rBet v 1 derivatives as determined by CD203c up-regulation Blood samples from three birch-allergic patients (K-M) were exposed to increasing concentrations (0.005 to 50 pM) of rBet v 1, rBet v 1-rs1, rBet v 1-rs2, rBet v 1-mosaic (x-axes). Anti-IgE served as a positive control. The mean stimulation indices (SI) (y-axes) reflect the up-regulation of CD203c expression compared to buffer (O). Standard deviations are indicated.

Next, rBet v 1-rs1 was compared with rBet v 1 and an equimolar mix of rBet v 1 fragments, testing for allergenic activity using basophils from birch pollen allergic patients. rBet v 1-rs1 did not cause any up-regulation of the CD203c expression up to the maximum concentration (i.e., 50 pM) tested in the six patients whereas rBet v 1 started to induce basophil activation at 0.5 pM and each of the patients responded to 50 pM. rBet v 1-rs1 exhibited even lower allergenic activity than the rBet v 1 fragment mix which induced CD203c up-regulation at 5 pM in one patient and at 50 pM in two of the 6 patients (FIG. 13A). Next, the three rBet v 1 derivatives were compared with rBet v 1 regarding allergenic activity using basophils from additional 4 patients (FIG. 13B). In three patients, rBet v 1 derivatives did not induce any CD203c up-regulation up to the maximum concentration of 50 pM, whereas rBet v 1 caused activation at 5 pM. In the fourth patient, the rBet v 1 derivatives showed a 100-fold reduction of allergenic activity compared to rBet v 1 (FIG. 13B). FIG. 15 shows the reproducibility of the CD203c assay when performed in triplicate determinations in three additional birch pollen allergic patients. It confirms the strongly reduced allergenic activity of the rBet v 1 derivatives.

E. Immunization with the rBet v 1 Mosaics Induces IgG Antibodies that Recognize Bet v 1 and Inhibits Allergic Patients' IgE Binding to Bet v 1

Figures 16A, 16B, 16C, 16D:
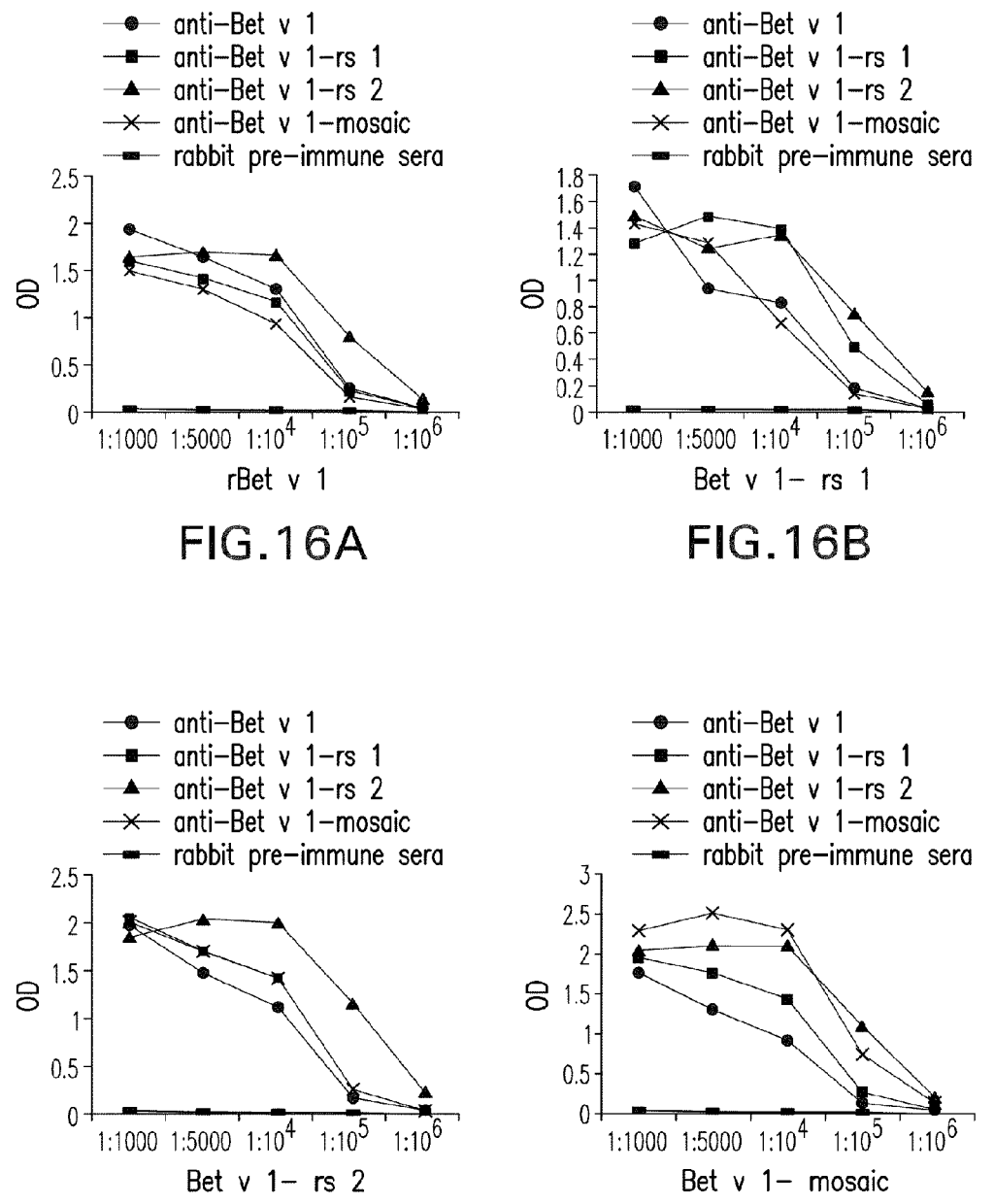
Figure 17:
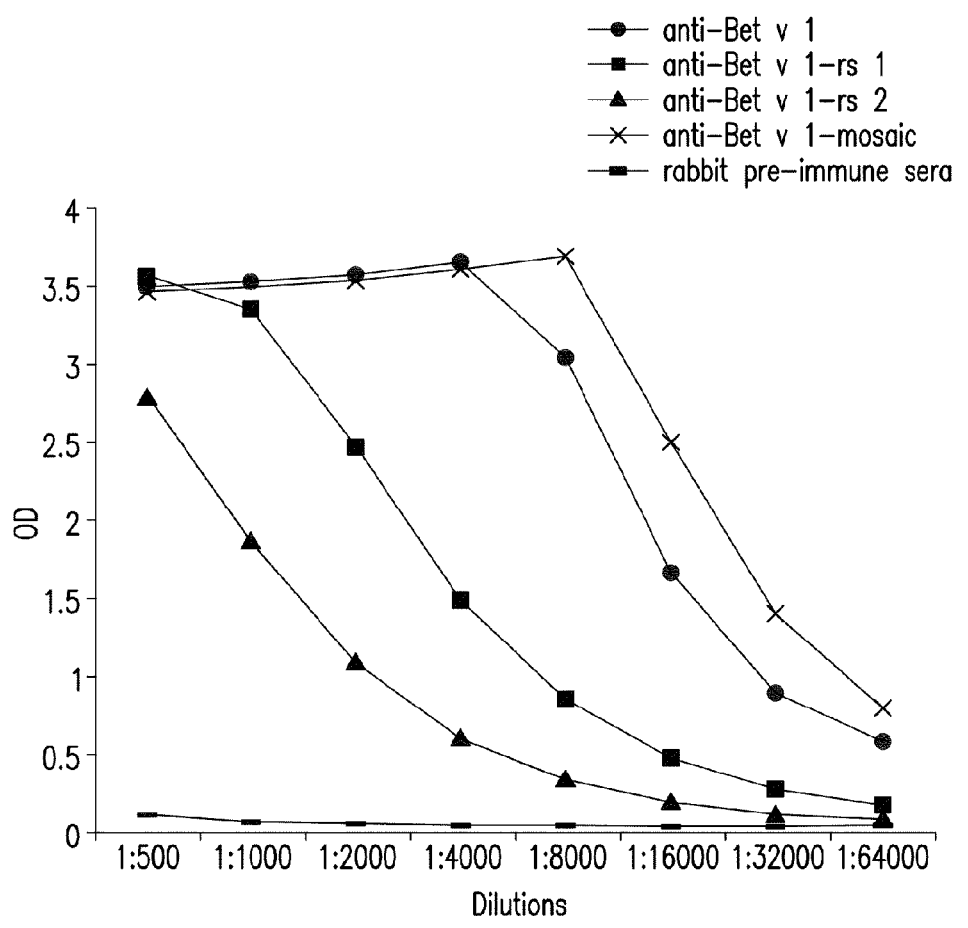

As shown in FIG. 16, rabbits immunized with the CFA adsorbed rBet v 1 derivatives showed an almost comparable IgG response to rBet v 1 wild type as the rabbit immunized with rBet v 1 (FIG. 16A). Rabbit anti-rBet v 1 antibodies reacted with the rBet v 1 derivatives although somewhat less than the anti-rBet v 1 derivative antibodies (FIG. 16B-D). Immunization with Al(OH)$_3$ adsorbed rBet v 1 and rBet v 1-mosaic gave an almost comparable IgG response to rBet v 1 wild type, whereas immunization with rBet v 1-rs 1 and rBet v 1-rs 2 resulted in lower titers of rBet v 1-specific antibodies (FIG. 17).

The derivatives were further investigated to determine whether rBet v 1 derivative-induced rabbit IgG antibodies can inhibit the binding of patients' serum IgE to the wild-type rBet v 1 in an ELISA competition assay. In case of immunization with CFA adsorbed proteins the anti-rBet v 1-rs1 antiserum inhibited the binding of birch pollen allergic patients' IgE to rBet v 1 between 56.5% and 98% (85% mean inhibition). The anti-rBet v 1-rs2 antiserum showed inhibition rates between 59.5% and 98.5% (87% mean inhibition) and the anti-rBet v 1-mosaic inhibited between 58% and 99.5% (82% mean inhibition). Interestingly, the rabbit antiserum against rBet v 1 derivatives showed higher average inhibition rates than the anti-rBet v 1 antibodies which yielded only 62% mean inhibition of IgE binding to rBet v 1 (Table 4, below). Immunization with Al(OH)$_3$ adsorbed rBet v 1 derivatives resulted also in Bet v 1-specific IgG responses which blocked allergic patients IgE binding to Bet v 1 (FIG. 17 and Table 6, below).

REFERENCES

1. Mothes N, Horak F, Valenta R. Transition from a botanical to a molecular classification in tree pollen allergy: Implications for diagnosis and therapy. Int Arch Allergy Immunol 2004; 135:357-73.
2. Breiteneder H, Pettenburger K, Bito A, Valenta R, Kraft D, Rulpold H, et al. The gene coding for the major birch pollen allergen Bet v I, is highly homologous to a pea disease resistance response gene. EMBO J. 1989; 8:1935-8.
3. Niederberger V, Pauli G, Grönlund H, Fröschl R, Rumpold H, Kraft D, et al. Recombinant birch pollen allergens (rBet v 1 and rBet v 2) contain most of the IgE epitopes present in birch, alder, hornbeam, hazel, and oak pollen: a quantitative IgE inhibition study with sera from different populations. J Allergy Clin Immunol 1998; 102:579-91.
4. Kazemi-Shirazi L, Pauli G, Purohit A, Spitzauer S, Fröschl R, Hoffmann-Sommergruber K, et al. Quantitative IgE inhibition experiments with purified recombinant allergens indicate pollen-derived allergens as the sensitizing agents responsible for many forms of plant food allergy. J Allergy Clin Immunol 2000; 105:116-25.
5. Pauli G, Oster J P, Deviller P, Heiss S, Bessot J C, Susani M, et al. Skin testing with recombinant allergens rBet v 1 and birch profilin, rBet v 2: diagnostic value for birch pollen and associated allergies. J Allergy Clin Immunol 1996; 97:1100-9.
6. Movérare R, Westritschnig K, Svensson M, Hayek B, Bende M, Pauli G, et al. Different IgE reactivity profiles in birch pollen-sensitive patients from six European populations revealed by recombinant allergens: an imprint of local sensitization. Int Arch Allergy Immunol 2002; 128: 325-35.
7. Pauli G, Larsen T H, Rak S, Horak F, Patorello E, Valenta R, et al. Efficacy of recombinant birch pollen vaccine for the treatment of birch-allergic rhinoconjunctivitis. J Allergy Clin Immunol 2008; 122:951-960.
8. Linhart B, Valenta R. Molecular design of allergy vaccines. Curr Opin Immunol 2005; 17:646-55.
9. Vrtala S, Hirtenlehner K, Vangelista L, Pastore A, Eichler H G, Sperr W R, et al. Conversion of the major birch pollen allergen, Bet v 1, into two nonanaphylactic T cell epitope-containing fragments: candidates for a novel form of specific immunotherapy. J Clin Invest 1997; 99:1673-81.
10. Vrtala S, Hirtenlehner K, Susani M, Akdis M, Kussebi F, Akdis C A, et al. Genetic engineering of a hypoallergenic trimer of the major birch pollen allergen, Bet v 1. FASEB J 2001; 15:2045-57.
11. Niederberger V, Horak F, Vrtala S, Spitzauer S, Krauth M T, Valent P, et al. Vaccination with genetically engineered allergens prevents progression of allergy disease. Proc Natl Acad Sci USA 2004; 101:14677-82.
12. Purohit A, Niederberger V, Kronqvist M, Horak F, Gronneberg R, Suck R, et al. Clinical effects of immunotherapy with genetically modified recombinant birch pollen Bet v 1 derivatives. Clin Exp Allergy 2008; 38:1514-25.
13. Reisinger J, Horak F, Pauli G, van Hage M, Crommwell O, König F, et al. Allergen-specific nasal IgG antibodies induced by vaccination with genetically modified allergens are associated with reduced nasal allergen sensitivity. J Allergy Clin Immunol 2005; 116:347-54.
14. Kahlert H, Suck R, Weber B, Nandy A, Wald M, Keller W, et al. Characterization of hypoallergenic recombinant Bet v 1 variant as a candidate for allergen-specific immunotherapy. Int Arch Allergy Immunol 2008; 145:193-206.
15. Klimek L, Bachert C, Doerner C, Meyer H, Narkus A. Specific immunotherapy with recombinant birch pollen allergen rBet v 1-FV is clinically efficacious (abstract). Allergy Clin Immunol Int 2005; (suppl 1):15.
16. Rak S. Clinical results with an hypoallergenic recombinant birch pollen allergen derivative (abstract). Congress of European Academy of Allergy and Clinical Immunology 2009.
17. Hoffmann-Sommergruber K, Susani M, Ferreira F, Jertschin P, Ahorn H, Steiner R, et al. High-level expression and purification of the major birch pollen allergen, Bet v 1. Protein Expr Purif 1997; 9:33-39.
18. Laffer S, Vangelista L, Steinberger P, Kraft D, Pastore A, Valenta R. Molecular characterization of Bip 1, a monoclonal antibody that modulates IgE binding to birch pollen allergen, Bet v 1. J Immunol 1996; 157:4953-62.
19. Wiedemann P, Giehl K, Almo S C, Fedorov A A, Girvin M, Steinberger P, et al. Molecular and structural analysis of a continuous birch profilin epitope defined by a monoclonal antibody. J Biol Chem 1996; 271:29915-21.
20. Fling S P, Gregerson D S. Peptide and protein molecular weight determination by electrophoresis using a high-molarity tris buffer system without urea. Anal Biochem 1986; 155:83-88.
21. Towbin H, Staehelin T, Gordon J. Electrophoretic transfer of proteins from polyacrylamide gels to nitrocellulose sheets: procedure and some applications. Proc Natl Acad Sci USA 1979; 76:4350-54.
22. Vrtala S, Akdis C A, Budak F, Akdis M, Blaser K, Kraft D, Valenta R. T cell epitope-containing hypoallergenic recombinant fragments of the major birch pollen allergen, Bet v 1, induce blocking antibodies. J Immunol 2000; 165:6653-59.
23. Pauli G, Purohit A, Oster J P, De Blay F, Vrtala S, Niederberger V, et al. Comparison of genetically engineered hypoallergenic rBet v 1 derivatives with rBet v 1 wild-type by skin prick and intradermal testing: results obtained in a French population. Clin Exp Allergy 2000; 30: 1076-84.
24. van Hage-Hamsten, Kronqvist M, Zetterström O, Johansson E, Niederberger V, Vrtala S, et al. Skin test evaluation of genetically engineered hypoallergenic derivatives of the major birch pollen allergen, Bet v 1: Results obtained with a mix of two recombinant Bet v 1 fragments and recombinant Bet v 1 trimer in a Swedish population before the birch pollen season. J Allergy Clin Immunol 1999; 104:969-77.
25. Nopp A, Halldén G, Lundahl J, Johansson E, Vrtala S, Valenta R, et al. Comparison of inflammatory responses to genetically engineered hypoallergenic derivatives of the major birch pollen allergen, Bet v 1 and to recombinant Bet v 1 wild type in skin chamber fluids collected from birch pollen-allergic patients. J Allergy Clin Immunol 2000; 106:101-9.
26. Focke M, Linhart B, Hartl A, Wiedermann U, Sperr W R, Valent P, et al. Non-anaphylactic surface-exposed peptides of the major birch pollen allergen, Bet v 1, for preventive vaccination. Clin Exp Allergy 2004; 34:1525-33.
27. Westrischnig K, Linhart B, Focke-Tejkl M, Pavkov T, Keller W, Ball T, et al. A hypoallergenic vaccine obtained by tail-to head restructuring of timothy grass pollen profilin, Phl p 12, for the treatment of cross-sensitization to profilin. J Immunol 2007; 179:7624-34.
28. Jahn-Schmid B, Radakovics A, Lüttkopf D, Scheurer S, Vieths S, Ebner C, Bohle B. Bet v $1_{142\text{-}153}$ is the dominant T-cell epitope of the major birch pollen allergen and important for cross-reactivity with Bet v 1-related food allergens. J Allergy clin Immunol 2005; 116:213-19.
29. Wallner M, Stöcklinger A, Thalhamer T, Bohle B, Vogel L, Briza P, Breiteneder H, Vieths S, Hartl A, Mari A, Ebner C, Lackner P, Hammerl P, Thalhamer J, Ferreira F. Allergy multivaccines created by DNA shuffling of tree pollen allergens. J Allergy Clin Immunol 2007; 120:374-80.
30. Ball T, Linhart B, Sonneck K, Blatt K, Herrmann H, Valent P, et al. Reducing allergenicity by altering allergen fold: a mosaic protein of Phl p 1 for allergy vaccination. Allergy 2009; 64:569-580.
31. Mothes-Luksch N, Stumvoll S, Linhart B, Focke M, Krauth M T, Hauswirth A, Valent P, Verdino P, Pavkov T, Keller W, Grote M, Valenta R. Disruption of allergenic activity of the major grass pollen allergen Phl p 2 by reassembly as a mosaic protein. J Immunol 2008; 181:4864-73.

32. Valenta R. The future of antigen-specific immunotherapy of allergy. Nat Rev Immunol 2002; 2:446-53.
33. Wiedermann U. Prophylaxis and therapy of allergy by mucosal tolerance induction with recombinant allergens or allergen constructs. Curr Drug Targets Inflamm Allergy 2005; 4:577-83.
34. Weiss R, Scheiblhofer S, Thalhamer J. DNA vaccines for allergy treatment. Methods Mol Med 2006; 127:253-67.
35. Barany U, Linhart B, Pilat N, Gattringer M, Bagley J, Muehlbacher F, et al. Tolerization of a type I allergic immune response through transplantation of genetically modified hematopoietic stem cells. J Immunol 2008; 180: 8168-75.
36. Fling S P, Gregerson D S. Peptide and protein molecular weight determination by electrophoresis using a high-molarity tris buffer system without urea. Anal Biochem 1986; 155:83-88.
37. Whitmore L, Wallace B A. DICHROWEB, an online server for protein secondary structure analyses from circular dichroism spectroscopic data. Nucleic Acids Res 2004; 32:668-73.
38. Hauswirth A W, Natter S, Ghannadan M, Majlesi Y, Schernthaner G H, Sperr W R, et al. Recombinant allergens promote expression of CD203c on basophils in sensitized individuals. J Allergy Clin Immunol 2002; 110:102-09.

INDUSTRIAL APPLICABILITY

The results herein confirm the utility of the inventive mosaic approach to the design of hypoallergenic allergens particularly suited to immunotherapy for the treatment and prevention of allergic disorders.

All patents and publications mentioned herein are incorporated by reference in their entirety. Nothing herein is to be construed as an admission that the invention is not entitled to antedate such disclosure by virtue of prior invention.

While the invention is herein described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention. Other advantages and features will become apparent from the claims filed hereafter, with the scope of such claims to be determined by their reasonable equivalents, as would be understood by those skilled in the art. Thus, the invention is intended to be defined not by the above description, but by the following claims and their equivalents.

APPENDIX A

Preferred wild-type allergens to be modified in accordance with mosaic approach of the present invention:

| ALLERGENS Species Name | Allergen Name | Biochem.ID or Obsolete name | MW | cDNA or protein | Reference, Acc. No. |
| --- | --- | --- | --- | --- | --- |
| *Ambrosia artemisiifolia* | | | | | |
| short ragweed | Amb a 1 | antigen E | 8 | C | 8, 20 |
| | Amb a 2 | antigen K | 38 | C | 8, 21 |
| | Amb a 3 | Ra3 | 11 | C | 22 |
| | Amb a 5 | Ra5 | 5 | C | 11, 23 |
| | Amb a 6 | Ra6 | 10 | C | 24, 25 |
| | Amb a 7 | Ra7 | 12 | P | 26 |
| *Ambrosia trifida* | | | | | |
| giant ragweed | Amb t 5 | Ra5G | 4.4 | C | 9, 10, 27 |
| *Artemisia vulgaris* | | | | | |
| mugwort | Art v 1 | | 27-29 | C | 28 |
| | Art v 2 | | 35 | P | 28A |
| | Art v 3 | lipid transfer protein | 12 | P | 53 |
| | Art v 4 | profilin | 14 | C | 29 |
| *Helianthus annuus* | | | | | |
| sunflower | Hel a 1 | | 34 | | 29A |
| | Hel a 2 | profilin | 15.7 | C | Y15210 |
| *Mercurialis annua* | Mer a 1 | profilin | 14-15 | C | Y13271 |
| Caryophyllales | | | | | |
| *Chenopodium album* | | | | | |
| lamb's-quarters, pigweed, | Che a 1 | | 17 | C | AY049012, 29B |
| white goosefootChe a 2 | profilin | | 14 | C | AY082337 |
| | Che a 3 | polcalcin | 10 | C | AY082338 |
| *Salsola kali* | | | | | |
| Russian-thistle | Sal k 1 | | 43 | P | 29C |
| Rosales | | | | | |
| *Humulus japonicus* | | | | | |
| Japanese hop | Hum j 4w | | | C | AY335187 |
| *Parietaria judaica* | | | | | |
| | Par j 1 | lipid transfer protein 1 | 15 | C | see list of isoallergens |
| | Par j 2 | lipid transfer protein 2 | | C | see list of isoallergens |
| | Par j 3 | profilin | | C | see list of isoallergens |
| *Parietaria officinalis* | Par o 1 | lipid transfer protein | 15 | | 29D |
| B. Grasses | | | | | |
| Poales | | | | | |
| *Cynodon dactylon* | | | | | |
| Bermuda grass | Cyn d 1 | | 32 | C | 30, S83343 |
| | Cyn d 7 | | | C | 31, X91256 |
| | Cyn d 12 | profilin | 14 | C | 31a, Y08390 |
| | Cyn d 15 | | 9 | C | AF517686 |

| ALLERGENS Species Name | Allergen Name | Biochem.ID or Obsolete name | MW | cDNA or protein | Reference, Acc. No. |
|---|---|---|---|---|---|
| | Cyn d 22w | enolase | data pending | | |
| | Cyn d 23 | Cyn d 14 | 9 | C | AF517685 |
| | Cyn d 24 | Pathogenesis-related p. | 21 | P | pending |
| *Dactylis glomerata* orchard grass | Dac g 1 | AgDg1 | 32 | P | 32 |
| | Dac g 2 | | 11 | C | 33, S45354 |
| | Dac g 3 | | | C | 33A, U25343 |
| | Dac g 5 | | 31 | P | 34 |
| *Festuca pratensis* meadow fescue | Fes p 4w | | 60 | — | |
| *Holcus lanatus* velvet grass | Hol l 1 | | | C | Z27084 |
| *Lolium perenne* rye grass | Lol p 1 | group I | 27 | C | 35, 36 |
| | Lol p 2 | group II | 11 | P | 37, 37A, X73363 |
| | Lol p 3 | group III | 11 | P | 38 |
| | Lol p 5 | Lol p IX, Lol p Ib | 31/35 | C | 34, 39 |
| | Lol p 11 | hom: trypsin inhibitor | 16 | | 39A |
| *Phalaris aquatica* canary grass | Pha a 1 | | | C | 40, S80654 |
| *Phleum pratense* timothy | Phl p 1 | | 27 | C | X78813 |
| | Phl p 2 | | | C | X75925, 41 |
| | Phl p 4 | | | P | 41A |
| | Phl p 5 | Ag25 | 32 | C | 42 |
| | Phl p 6 | | | C | Z27082, 43 |
| | Phl p 11 | trypsin inhibitor hom. | 20 | C | AF521563, 43A |
| | Phl p 12 | profilin | | C | X77583, 44 |
| | Phl p 13 | polygalacturonase | 55-60 | C | AJ238848 |
| *Poa pratensis* Kentucky blue grass | Poa p 1 | group I | 33 | P | 46 |
| | Poa p 5 | | 31/34 | C | 34, 47 |
| *Sorghum halepense* Johnson grass | Sor h 1 | | | C | 48 |
| C. Trees Arecales | | | | | |
| *Phoenix dactylifera* date palm | Pho d 2 | profilin | 14.3 | C | Asturias p.c. |
| Fagales | | | | | |
| *Alnus glutinosa* alder | Aln g 1 | | 17 | C | S50892 |
| *Betula verrucosa* birch | Bet v 1 | | 17 | C | see list of isoallergens |
| | Bet v 2 | profilin | 15 | C | M65179 |
| | Bet v 3 | | | C | X79267 |
| | Bet v 4 | | 8 | C | X87153, S54819 |
| | Bet v 6 | h: isoflavone reductase | 33.5 | C | see list of isoallergens |
| | Bet v 7 | cyclophilin | 18 | P | P81531 |
| *Carpinus betulus* hornbeam | Car b 1 | | 17 | C | see list of isoallergens |
| *Castanea sativa* chestnut | Cas s 1 | | 22 | P | 52 |
| | Cas s 5 | chitinase | | | |
| | Cas s 8 | lipid transfer protein | 9.7 | P | 53 |
| *Corylus avellana* hazel | Cor a 1 | | 17 | C | see list of isoallergens |
| | Cor a 2 | profilin | 14 | C | |
| | Cor a 8 | lipid transfer protein | 9 | C | |
| | Cor a 9 | 11S globulin-like protein | 40/? | C | Beyer p.c. |
| | Cor a 10 | luminal binding prot. | 70 | C | AJ295617 |
| | Cor a 11 | 7S vicilin-like prot. | 48 | C | AF441864 |
| *Quercus alba* White oak. | Que a1 | | 17 | P | 54 |
| Lamiales Oleaceae | | | | | |
| *Fraxinus excelsior* ash | Fra e 1 | | 20 | P | 58A, AF526295 |
| *Ligustrum vulgare* privet | Lig v 1 | | 20 | P | 58A |
| *Olea europea* olive | Ole e 1 | | 16 | C | 59, 60 |
| | Ole e 2 | profilin | 15-18 | C | 60A |
| | Ole e 3 | | 9.2 | | 60B |
| | Ole e 4 | | 32 | P | P80741 |
| | Ole e 5 | superoxide dismutase | 16 | P | P80740 |

-continued

| ALLERGENS Species Name | Allergen Name | Biochem.ID or Obsolete name | MW | cDNA or protein | Reference, Acc. No. |
|---|---|---|---|---|---|
| | Ole e 6 | | 10 | C | 60C, U86342 |
| | Ole e 7 | | ? | P | 60D, P81430 |
| | Ole e 8 | Ca2+-binding protein | 21 | C | 60E, AF078679 |
| | Ole e 9 | beta-1,3-glucanase | 46 | C | AF249675 |
| | Ole e 10 | glycosyl hydrolase hom. | 11 | C | 60F, AY082335 |
| *Syringa vulgaris* lilac Plantaginaceae | Syr v 1 | | 20 | P | 58A |
| *Plantago lanceolata* English plantain Pinales | Pla l 1 | | 18 | P | P842242 |
| *Cryptomeria japonica* sugi | Cry j 1 | | 41-45 | C | 55, 56 |
| | Cry j 2 | | | C | 57, D29772 |
| *Cupressus arizonica* cypress | Cup a 1 | | 43 | C | A1243570 |
| *Cupressus sempervirens* common cypress | Cup s 1 | | 43 | C | see list of isoallergens |
| | Cup s 3w | | 34 | C | ref pending |
| *Juniperus ashei* mountain cedar | Jun a 1 | | 43 | P | P81294 |
| | Jun a 2 | | | C | 57A, AJ404653 |
| | Jun a 3 | | 30 | P | 57B, P81295 |
| *Juniperus oxycedrus* prickly juniper | Jun o 4 | hom: calmodulin | 29 | C | 57C, AF031471 |
| *Juniperus sabinoides* mountain cedar | Jun s 1 | | 50 | P | 58 |
| *Juniperus virginiana* eastern red cedar Platanaceae | Jun v 1 | | 43 | P | P81825, 58B |
| *Platanus acerifolia* London plane tree | Pla a 1 | | 18 | P | P82817 |
| | Pla a 2 | | 43 | P | P82967 |
| | Pla a 3 | lipid transfer protein | 10 | P | Iris p.c. |
| D. Mites *Acarus siro* mite | | | | | |
| fatty acid binding prot. | Aca s 13 | arthropod | 14* | C | AJ006774 |
| *Blomia tropicalis* mite | Blo t 1 | cysteine protease | 39 | C | AF277840 |
| | Blo t 3 | trypsin | 24* | C | Cheong p.c. |
| | Blo t 4 | alpha amylase | 56 | C | Cheong p.c. |
| | Blo t 5 | | | C | U59102 |
| | Blo t 6 | chymotrypsin | 25 | C | Cheong p.c. |
| | Blo t 10 | tropomyosin | 33 | C | 61 |
| | Blo t 11 | paramyosin | 110 | C | AF525465, 61A |
| | Blo t 12 | Bt11a | | C | U27479 |
| | Blo t 13 | Bt6, fatty acid bind prot. | | C | U58106 |
| | Blo t 19 | anti-microbial pep. hom. | 7.2 | C | Cheong p.c. |
| *Dermatophagoides farinae* American house dust mite | Der f 1 | cysteine protease | 25 | C | 69 |
| | Der f 2 | | 14 | C | 70, 70A, see list of isoallergens |
| | Der f 3 | trypsin | 30 | C | 63 |
| | Der f 7 | | 24-31 | C | SW: Q26456, 71 |
| | Der f 10 | tropomyosin | | C | 72 |
| | Der f 11 | paramyosin | 98 | C | 72A |
| | Der f 14 | mag3, apolipophorin | | C | D17686 |
| | Der f 15 | 98k chitinase | 98 | C | AF178772 |
| | Der f 16 | gelsolin/villin | 53 | C | 71A |
| | Der f 17 | Ca binding EF protein | 53 | C | 71A |
| | Der f 18w | 60k chitinase | 60 | C | Weber p.c. |
| *Dermatophagoides microceras* house dust mite | Der m 1 | cysteine protease | 25 | P | 68 |
| *Dermatophagoides pteronyssinus* European house dust mite | Der p 1 | antigen P1, cysteine protease | 25 | C | 62, see list of isoallergens |
| | Der p 2 | | 14 | C | 62A-C, see list of isoallergens |
| | Der p 3 | trypsin | 28/30 | C | 63 |
| | Der p 4 | amylase | 60 | P | 64 |
| | Der p 5 | | 14 | C | 65 |
| | Der p 6 | chymotrypsin | 25 | P | 66 |
| | Der p 7 | | 22/28 | C | 67 |

| ALLERGENS Species Name | Allergen Name | Biochem.ID or Obsolete name | MW | cDNA or protein | Reference, Acc. No. |
|---|---|---|---|---|---|
| | Der p 8 | glutathione transferase | | C | 67A |
| | Der p 9 | collagenolytic serine pro. | | P | 67B |
| | Der p 10 | tropomyosin | 36 | C | Y14906 |
| | Der p 14 | apolipophorin like prot. | | C | Epton p.c. |
| *Euroglyphus maynei* mite | Eur m 2 | | | C | see list of isoallergens |
| | Eur m 14 | apolipophorin | 177 | C | AF149827 |
| *Glycyphagus domesticus* storage mite | Gly d 2 | | | C | 72B, see isoallergen list |
| *Lepidoglyphus destructor* storage mite | Lep d 2 Lep d 1 | | 15 | C | 73, 74, 74A, see isoallergen list |
| | Lep d 5 | | | C | 75, AJ250278 |
| | Lep d 7 | | | C | 75, AJ271058 |
| | Lep d 10 | tropomyosin | | C | 75A, AJ250096 |
| | Lep d 13 | | | C | 75, AJ250279 |
| *Tyrophagus putrescentiae* storage mite | Tyr p 2 | | | C | 75B, Y12690 |
| E. Animals | | | | | |
| *Bos domesticus* domestic cattle | Bos d 2 | Ag3, lipocalin | 20 | C | 76, see isoallergen list (see also foods) |
| | Bos d 3 | Ca-binding S100 hom. | 11 | C | L39834 |
| | Bos d 4 | alpha-lactalbumin | 14.2 | C | M18780 |
| | Bos d 5 | beta-lactoglobulin | 18.3 | C | X14712 |
| | Bos d 6 | serum albumin | 67 | C | M73993 |
| | Bos d 7 | immunoglobulin | 160 | | 77 |
| | Bos d 8 | caseins | 20-30 | | 77 |
| *Canis familiaris* (*Canis domesticus*) dog | Can f 1 | | 25 | C | 78, 79 |
| | Can f 2 | | 27 | C | 78, 79 |
| | Can f 3 | albumin | | C | S72946 |
| | Can f 4 | | 18 | P | A59491 |
| *Equus caballus* domestic horse | Equ c 1 | lipocalin | 25 | C | U70823 |
| | Equ c 2 | lipocalin | 18.5 | P | 79A, 79B |
| | Equ c 3 | Ag3 - albumin | 67 | C | 79C, X74045 |
| | Equ c 4 | | 17 | P | 79D |
| | Equ c 5 | AgX | 17 | P | Goubran Botros p.c. |
| *Felis domesticus* cat (saliva) | Fel d 1 | cat-1 | 38 | C | 15 |
| | Fel d 2 | albumin | | C | 79E, X84842 |
| | Fel d 3 | cystatin | 11 | C | 79F, AF238996 |
| | Fel d 4 | lipocalin | 22 | C | AY497902 |
| | Fel d 5w | immunoglobulin A | 400 | | Adedoyin p.c. |
| | Fel d 6w | immunoglobulin M | 800-1000 | | Adedoyin p.c. |
| | Fel d 7w | immunoglobulin G | 150 | | Adedoyin p.c. |
| *Cavia porcellus* guinea pig | Cav p 1 | lipocalin homologue | 20 | P | SW: P83507, 80 |
| | Cav p 2 | | 17 | P | SW: P83508 |
| *Mus musculus* mouse (urine) | Mus m 1 | MUP | 19 | C | 81, 81A |
| *Rattus norvegius* rat (urine) | Rat n 1 | | 17 | C | 82, 83 |
| F. Fungi (moulds) | | | | | |
| 1. Ascomycota | | | | | |
| 1.1 Dothideales | | | | | |
| *Alternaria alternata* | Alt a 1 | | 28 | C | U82633 |
| | Alt a 2 | | 25 | C | 83A, U62442 |
| | Alt a 3 | heat shock prot. | 70 | C | U87807, U87808 |
| | Alt a 4 | prot. disulfideisomerase | 57 | C | X84217 |
| | Alt a 6 | acid ribosomal prot. P2 | 11 | C | X78222, U87806 |
| | Alt a 7 | YCP4 protein | 22 | C | X78225 |
| | Alt a 10 | aldehyde dehydrogenase | 53 | C | X78227, P42041 |
| | Alt a 11 | enolase | 45 | C | U82437 |
| | Alt a 12 | acid ribosomal prot. P1 | 11 | C | X84216 |
| *Cladosporium herbarum* | Cla h 1 | | 13 | | 83B, 83C |
| | Cla h 2 | | 23 | | 83B, 83C |
| | Cla h 3 | aldehyde dehydrogenase | 53 | C | X78228 |
| | Cla h 4 | acid ribosomal prot. P2 | 11 | C | X78223 |
| | Cla h 5 | YCP4 protein | 22 | C | X78224 |

| ALLERGENS Species Name | Allergen Name | Biochem.ID or Obsolete name | MW | cDNA or protein | Reference, Acc. No. |
|---|---|---|---|---|---|
| | Cla h 6 | enolase | 46 | C | X78226 |
| | Cla h 12 | acid ribosomal prot. P1 | 11 | C | X85180 |
| 1.2 Eurotiales | | | | | |
| *Aspergillus flavus* | Asp fl 13 | alkaline serine protease | 34 | | 84 |
| *Aspergillus fumigatus* | Asp f 1 | | 18 | C | M83781, S39330 |
| | Asp f 2 | | 37 | C | U56938 |
| | Asp f 3 | peroxisomal protein | 19 | C | U20722 |
| | Asp f 4 | | 30 | C | AJ001732 |
| | Asp f 5 | metalloprotease | 40 | C | Z30424 |
| | Asp f 6 | Mn superoxide dismut. | 26.5 | C | U53561 |
| | Asp f 7 | | 12 | C | AJ223315 |
| | Asp f 8 | ribosomal prot. P2 | 11 | C | AJ224333 |
| | Asp f 9 | | 34 | C | AJ223327 |
| | Asp f 10 | aspartic protease | 34 | C | X85092 |
| | Asp f 11 | peptidyl-prolyl isomeras | 24 | | 84A |
| | Asp f 12 | heat shock prot. P90 | 90 | C | 85 |
| | Asp f 13 | alkaline serine protease | 34 | | 84B |
| | Asp f 15 | | 16 | C | AJ002026 |
| | Asp f 16 | | 43 | C | g3643813 |
| | Asp f 17 | | | C | AJ224865 |
| | Asp f 18 | vacuolar serine protease | 34 | | 84C |
| | Asp f 22w | enolase | 46 | C | AF284645 |
| | Asp f 23 | L3 ribosomal protein | 44 | C | 85A, AF464911 |
| *Aspergillus niger* | Asp n 14 | beta-xylosidase | 105 | C | AF108944 |
| | Asp n 18 | vacuolar serine protease | 34 | C | 84B |
| | Asp n 25 | 3-phytase B | 66-100 | C | 85B, P34754 |
| | Asp n ? | | 85 | C | Z84377 |
| *Aspergillus oryzae* | | | | | |
| | Asp o 13 | alkaline serine protease | 34 | C | X17561 |
| | Asp o 21 | TAKA-amylase A | 53 | C | D00434, M33218 |
| *Penicillium brevicompactum* | Pen b 13 | alkaline serine protease | 33 | | 86A |
| *Penicillium chrysogenum* (formerly *P. notatum*) | Pen ch 13 | alkaline serine protease | 34 | | 87 |
| | Pen ch 18 | vacuolar serine protease | 32 | | 87 |
| | Pen ch 20 | N-acetyl glucosaminidas | 68 | | 87A |
| *Penicillium citrinum* | Pen c 3 | peroxisomal mem. prot. | 18 | | 86B |
| | Pen c 13 | alkaline serine protease | 33 | | 86A |
| | Pen c 19 | heat shock prot. P70 | 70 | C | U64207 |
| | Pen c 22w | enolase | 46 | C | AF254643 |
| | Pen c 24 | elongation factor 1 beta | | C | AY363911 |
| *Penicillium oxalicum* | Pen o 18 | vacuolar serine protease | 34 | | 87B |
| 1.3 Hypocreales | | | | | |
| *Fusarium culmorum* | Fus c 1 | ribosomal prot. P2 | 11* | C | AY077706 |
| | Fus c 2 | thioredoxin-like prot. | 13* | C | AY077707 |
| 1.4 Onygenales | | | | | |
| *Trichophyton rubrum* | Tri r 2 | | | C | 88 |
| | Tri r 4 | serine protease | | C | 88 |
| *Trichophyton tonsurans* | Tri t 1 | | 30 | P | 88A |
| | Tri t 4 | serine protease | 83 | C | 88 |
| 1.5 Saccharomycetales | | | | | |
| *Candida albicans* | Cand a 1 | | 40 | C | 89 |
| | Cand a 3 | peroxisomal protein | 29 | C | AY136739 |
| *Candida boidinii* | Cand b 2 | | 20 | C | J04984, J04985 |
| 2. Basidiomycotina | | | | | |
| 2.1 Hymenomycetes | | | | | |
| *Psilocybe cubensis* | Psi c 1 | | | | |
| | Psi c 2 | cyclophilin | 16 | | 89A |
| *Coprinus comatus* shaggy cap | Cop c 1 | leucine zipper protein | 11 | C | AJ132235 |
| | Cop c 2 | | | | AJ242791 |
| | Cop c 3 | | | | AJ242792 |
| | Cop c 5 | | | | AJ242793 |
| | Cop c 7 | | | | AJ242794 |
| 2.2 Urediniomycetes | | | | | |
| *Rhodotorula mucilaginosa* | Rho m 1 | enolase | 47 | C | 89B |
| | Rho m 2 | vacuolar serine protease | 31 | C | AY547285 |
| 2.3 Ustilaginomycetes | | | | | |
| *Malassezia furfur* | Mala f 2 | MF1, peroxisomal membrane protein | 21 | C | AB011804, 90 |
| | Mala f 3 | MF2, peroxisomal membrane protein | 20 | C | AB011805, 90 |
| | Mala f 4 | mitochondrial malate dehydrogenase | 35 | C | AF084828, 90A |
| *Malassezia sympodialis* | Mala s 1 | | | C | X96486, 91 |
| | Mala s 5 | | 18* | C | AJ011955 |

-continued

| ALLERGENS Species Name | Allergen Name | Biochem.ID or Obsolete name | MW | cDNA or protein | Reference, Acc. No. |
|---|---|---|---|---|---|
| | Mala s 6 | | 17* | C | AJ011956 |
| | Mala s 7 | | | C | AJ011957, 91A |
| | Mala s 8 | | 19* | C | AJ011958, 91A |
| | Mala s 9 | | 37* | C | AJ011959, 91A |
| | Mala s 10 | heat shock prot. 70 | 86 | C | AJ428052 |
| | Mala s 11 | Mn superoxide dismut. | 23 | C | AJ548421 |
| 3. Deuteromycotina | | | | | |
| 3.1 Tuberculariales | | | | | |
| *Epicoccum purpurascens* (formerly *E. nigrum*) | Epi p 1 | serine protease | 30 | P | SW: P83340, 91B |
| G. Insects | | | | | |
| *Aedes aegyptii* | | | | | |
| mosquito | Aed a 1 | apyrase | 68 | C | L12389 |
| | Aed a 2 | | 37 | C | M33157 |
| *Apis mellifera* | | | | | |
| honey bee | Api m 1 | phospholipase A2 | 16 | C | 92 |
| | Api m 2 | hyaluronidase | 44 | C | 93 |
| | Api m 4 | melittin | 3 | C | 94 |
| | Api m 6 | | 7-8 | P | Kettner p.c. |
| | Api m 7 | CUB serine protease | 39 | C | AY127579 |
| *Bombus pennsylvanicus* | | | | | |
| bumble bee | Bom p 1 | phospholipase | 16 | P | 95 |
| | Bom p 4 | protease | | P | 95 |
| *Blattella germanica* | | | | | |
| German cockroach | Bla g 1 | Bd90k | | C | |
| | Bla g 2 | aspartic protease | 36 | C | 96 |
| | Bla g 4 | calycin | 21 | C | 97 |
| | Bla g 5 | glutathione transferase | 22 | C | 98 |
| | Bla g 6 | troponin C | 27 | C | 98 |
| *Periplaneta americana* | | | | | |
| American cockroach | Per a 1 | Cr-PII | | C | |
| | Per a 3 | Cr-PI | 72-78 | C | 98A |
| | Per a 7 | tropomyosin | 37 | C | Y14854 |
| *Chironomus kiiensis* | | | | | |
| midge | Chi k 10 | tropomyosin | 32.5* | C | AJ012184 |
| *Chironomus thummi thummi* | | | | | |
| midge | Chi t 1-9 | hemoglobin | 16 | C | 99 |
| | Chi t 1.01 | component III | 16 | C | P02229 |
| | Chi t 1.02 | component IV | 16 | C | P02230 |
| | Chi t 2.0101 | component I | 16 | C | P02221 |
| | Chi t 2.0102 | component IA | 16 | C | P02221 |
| | Chi t 3 | component II-beta | 16 | C | P02222 |
| | Chi t 4 | component IIIA | 16 | C | P02231 |
| | Chi t 5 | component VI | 16 | C | P02224 |
| | Chi t 6.01 | component VIIA | 16 | C | P02226 |
| | Chi t 6.02 | component IX | 16 | C | P02223 |
| | Chi t 7 | component VIIB | 16 | C | P02225 |
| | Chi t 8 | component VIII | 16 | C | P02227 |
| | Chi t 9 | component X | 16 | C | P02228 |
| *Ctenocephalides felis felis* | | | | | |
| cat flea | Cte f 1 | | | C | |
| | Cte f 2 | M1b | 27 | C | AF231352 |
| | Cte f 3 | | 25 | C | |
| *Thaumetopoea pityocampa* | | | | | |
| pine processionary moth | Tha p 1 | | 15 | P | PIR: A59396, 99A |
| *Lepisma saccharina* | | | | | |
| silverfish | Lep s 1 | tropomyosin | 36 | C | AJ309202 |
| *Dolichovespula maculate* | | | | | |
| white face hornet | Dol m 1 | phospholipase A1 | 35 | C | 100 |
| | Dol m 2 | hyaluronidase | 44 | C | 101 |
| | Dol m 5 | antigen 5 | 23 | C | 102, 103 |
| *Dolichovespula arenaria* | | | | | |
| yellow hornet | Dol a 5 | antigen 5 | 23 | C | 104 |
| *Polistes annularies* | | | | | |
| wasp | Pol a 1 | phospholipase A1 | 35 | P | 105 |
| | Pol a 2 | hyaluronidase | 44 | P | 105 |
| | Pol a 5 | antigen 5 | 23 | C | 104 |
| *Polistes dominulus* | | | | | |
| Mediterranean paper wasp | Pol d 1 | | | | Hoffman p.c. |
| | Pol d 4 | serine protease | 32-34 | C | Hoffman p.c. |
| | Pol d 5 | | | | P81656 |
| *Polistes exclamans* | | | | | |
| wasp | Pol e 1 | phospholipase A1 | 34 | P | 107 |
| | Pol e 5 | antigen 5 | 23 | C | 104 |

| ALLERGENS Species Name | Allergen Name | Biochem.ID or Obsolete name | MW | cDNA or protein | Reference, Acc. No. |
|---|---|---|---|---|---|
| *Polistes fuscatus* wasp | Pol f 5 | antigen 5 | 23 | C | 106 |
| *Polistes gallicus* wasp | Pol g 5 | antigen 5 | 24 | C | P83377 |
| *Polistes metricus* wasp | Pol m 5 | antigen 5 | 23 | C | 106 |
| *Vespa crabo* European hornet | Vesp c 1 | phospholipase | 34 | P | 107 |
| | Vesp c 5 | antigen 5 | 23 | C | 106 |
| *Vespa mandarina* giant asian hornet | Vesp m 1 | | | | Hoffman p.c. |
| | Vesp m 5 | | | | P81657 |
| *Vespula flavopilosa* yellowjacket | Ves f 5 | antigen 5 | 23 | C | 106 |
| *Vespula germanica* yellowjacket | Ves g 5 | antigen 5 | 23 | C | 106 |
| *Vespula maculifrons* yellowjacket | Ves m 1 | phospholipase A1 | 33.5 | C | 108 |
| | Ves m 2 | hyaluronidase | 44 | P | 109 |
| | Ves m 5 | antigen 5 | 23 | C | 104 |
| *Vespula pennsylvanica* yellowjacket | Ves p 5 | antigen 5 | 23 | C | 106 |
| *Vespula squamosa* yellowjacket | Ves s 5 | antigen 5 | 23 | C | 106 |
| *Vespula vidua* wasp | Ves vi 5 | antigen 5 | 23 | C | 106 |
| *Vespula vulgaris* yellowjacket | Ves v 1 | phospholipase A1 | 35 | C | 105A |
| | Ves v 2 | hyaluronidase | 44 | P | 105A |
| | Ves v 5 | antigen 5 | 23 | C | 104 |
| *Myrmecia pilosula* Australian jumper ant | Myr p 1 | | | C | X70256 |
| | Myr p 2 | | | C | S81785 |
| *Solenopsis geminata* tropical fire ant | Sol g 2 | | | | Hoffman p.c. |
| | Sol g 4 | | | | Hoffman p.c. |
| *Solenopsis invicta* fire ant | Sol i 2 | | 13 | C | 110, 111 |
| | Sol i 3 | | 24 | C | 110 |
| | Sol i 4 | | 13 | C | 110 |
| *Solenopsis saevissima* Brazilian fire ant | Sol s 2 | | | | Hoffman p.c. |
| *Triatoma protracta* California kissing bug H. Foods | Tria p 1 | Procalin | 20 | C | AF179004, 111A. |
| *Gadus callarias* cod | Gad c 1 | allergen M | 12 | C | 112, 113 |
| *Salmo salar* Atlantic salmon | Sal s 1 | parvalbumin | 12 | C | X97824 |
| *Bos domesticus* domestic cattle (milk) see also animals | Bos d 4 | alpha-lactalbumin | 14.2 | C | M18780 |
| | Bos d 5 | beta-lactoglobulin | 18.3 | C | X14712 |
| | Bos d 6 | serum albumin | 67 | C | M73993 |
| | Bos d 7 | immunoglobulin | 160 | | 77 |
| | Bos d 8 | caseins | 20-30 | | 77 |
| *Gallus domesticus* chicken | Gal d 1 | ovomucoid | 28 | C | 114, 115 |
| | Gal d 2 | ovalbumin | 44 | C | 114, 115 |
| | Gal d 3 | Ag22, conalbumin | 78 | C | 114, 115 |
| | Gal d 4 | lysozyme | 14 | C | 114, 115 |
| | Gal d 5 | serum albumin | 69 | C | X60688 |
| *Metapenaeus ensis* shrimp | Met e 1 | tropomyosin | | C | U08008 |
| *Penaeus aztecus* shrimp | Pen a 1 | tropomyosin | 36 | P | 116 |
| *Penaeus indicus* shrimp | Pen i 1 | tropomyosin | 34 | C | 116A |
| *Penaeus monodon* black tiger shrimp | Pen m 1 | tropomyosin | 38 | C | |
| | Pen m 2 | arginine kinase | 40 | C | AF479772, 117 |
| *Todarodes pacificus* squid | Tod p 1 | tropomyosin | 38 | P | 117A |
| *Helix aspersa* brown garden snail | Hel as 1 | tropomyosin | 36 | C | Y14855, 117B |

| ALLERGENS Species Name | Allergen Name | Biochem.ID or Obsolete name | MW | cDNA or protein | Reference, Acc. No. |
|---|---|---|---|---|---|
| *Haliotis midae* | | | | | |
| abalone | Hal m 1 | | 49 | | 117C |
| *Rana esculenta* | | | | | |
| edible frog | Ran e 1 | parvalbumin alpha | 11.9* | C | AJ315959 |
| | Ran e 2 | parvalbumin beta | 11.7* | C | AJ414730 |
| *Brassica juncea* | | | | | |
| oriental mustard | Bra j 1 | 2S albumin | 14 | C | 118 |
| *Brassica napus* | | | | | |
| rapeseed | Bra n 1 | 2S albumin | 15 | P | 118A, P80208 |
| *Brassica rapa* | | | | | |
| turnip | Bra r 2 | hom: prohevein | 25 | | P81729 |
| *Hordeum vulgare* | | | | | |
| barley | Hor v 15 | BMAI-1 | 15 | C | 119 |
| | Hor v 16 | alpha-amylase | | | |
| | Hor v 17 | beta-amylase | | | |
| | Hor v 21 | gamma-3 hordein | 34 | C | 119A, SW: P80198 |
| *Secale cereale* | | | | | |
| rye | Sec c 20 | secalin | | | see isoall. list |
| *Triticum aestivum* | | | | | |
| wheat | Tri a 18 | agglutinin | | | |
| | Tri a 19 | omega-5 gliadin | 65 | P | PIR: A59156 |
| *Zea mays* | | | | | |
| maize, corn | Zea m 14 | lipid transfer prot. | 9 | P | P19656 |
| *Oryza sativa* | | | | | |
| rice | Ory s 1 | | | C | 119B, U31771 |
| *Apium gravaolens* | | | | | |
| celery | Api g 1 | hom: Bet v 1 | 16* | C | Z48967 |
| | Api g 4 | profilin | | | AF129423 |
| | Api g 5 | | 55/58 | P | P81943 |
| *Daucus carota* | | | | | |
| carrot | Dau c 1 | hom: Bet v 1 | 16 | C | 117D, see isoallergen list |
| | Dau c 4 | profilin | | C | AF456482 |
| *Corylus avellana* | | | | | |
| hazelnut | Cor a 1.04 | hom: Bet v 1 | 17 | C | see list of isoallergens |
| | Cor a 2 | profilin | 14 | C | AF327622 |
| | Cor a 8 | lipid transfer protein | 9 | C | AF329829 |
| *Malus domestica* | | | | | |
| apple | Mal d 1 | hom: Bet v 1 | | C | see list of isoallergens |
| | Mal d 2 | hom: thaumatin | | C | AJ243427 |
| | Mal d 3 | lipid transfer protein | 9 | C | Pastorello p.c. |
| | Mal d 4 | profilin | 14.4* | C | see list of isoallergens |
| *Pyrus communis* | | | | | |
| pear | Pyr c 1 | hom: Bet v 1 | 18 | C | AF05730 |
| | Pyr c 4 | profilin | 14 | C | AF129424 |
| | Pyr c 5 | hom: isoflavone reductas | 33.5 | C | AF071477 |
| *Persea americana* | | | | | |
| avocado | Pers a 1 | endochitinase | 32 | C | Z78202 |
| *Prunus armeniaca* | | | | | |
| apricot | Pru ar 1 | hom: Bet v 1 | | C | U93165 |
| | Pru ar 3 | lipid transfer protein | 9 | P | |
| *Prunus avium* | | | | | |
| sweet cherry | Pru av 1 | hom: Bet v 1 | | C | U66076 |
| | Pru av 2 | hom: thaumatin | | C | U32440 |
| | Pru av 3 | lipid transfer protein | 10 | C | AF221501 |
| | Pru av 4 | profilin | 15 | C | AF129425 |
| *Prunus domestica* | | | | | |
| European plum | Pru d 3 | lipid transfer protein | 9 | P | 119C |
| *Prunus persica* | | | | | |
| peach | Pru p 3 | lipid transfer protein | 10 | P | P81402 |
| | Pru p 4 | profilin | 14 | C | see isoallergen list |
| *Asparagus officinalis* | | | | | |
| Asparagus | Aspa o 1 | lipid transfer protein | 9 | P | 119D |
| *Crocus sativus* | | | | | |
| saffron crocus | Cro s 1 | | 21 | | Varasteh A-R p.c. |
| *Lactuca sativa* | | | | | |
| lettuce | Lac s 1 | lipid transfer protein | 9 | | Vieths p.c. |
| *Vitis vinifera* | | | | | |
| grape | Vit v 1 | lipid transfer protein | 9 | P | P80274 |
| *Musa x paradisiaca* | | | | | |
| banana | Mus xp 1 | profilin | 15 | C | AF377948 |
| *Ananas comosus* | | | | | |
| pineapple | Ana c 1 | profilin | 15 | C | AF377949 |
| | Ana c 2 | bromelain | 22.8* | C | 119E-G, D14059 |
| *Citrus limon* | | | | | |
| lemon | Cit l 3 | lipid transfer protein | 9 | P | Torrejon p.c. |

| ALLERGENS Species Name | Allergen Name | Biochem.ID or Obsolete name | MW | cDNA or protein | Reference, Acc. No. |
|---|---|---|---|---|---|
| *Citrus sinensis* | | | | | |
| sweet orange | Cit s 1 | germin-like protein | 23 | P | Torrejon p.c. |
| | Cit s 2 | profilin | 14 | P | Torrejon p.c. |
| | Cit s 3 | lipid transfer protein | 9 | P | Torrejon p.c. |
| *Litchi chinensis* | | | | | |
| litchi | Lit c 1 | profilin | 15 | C | AY049013 |
| *Sinapis alba* | | | | | |
| yellow mustard | Sin a 1 | 2S albumin | 14 | C | 120 |
| *Glycine max* | | | | | |
| soybean | Gly m 1 | HPS | 7 | P | 120A |
| | Gly m 2 | | 8 | P | A57106 |
| | Gly m 3 | profilin | 14 | C | see list of isoallergens |
| | Gly m 4 | (SAM22) PR-10 prot. | 17 | C | X60043, 120B |
| *Vigna radiata* | | | | | |
| mung bean | Vig r 1 | PR-10 protein | 15 | C | AY792956 |
| *Arachis hypogaea* | | | | | |
| peanut | Ara h 1 | vicilin | 63.5 | C | L34402 |
| | Ara h 2 | conglutin | 17 | C | L77197 |
| | Ara h 3 | glycinin | 60 | C | AF093541 |
| | Ara h 4 | glycinin | 37 | C | AF086821 |
| | Ara h 5 | profilin | 15 | C | AF059616 |
| | Ara h 6 | hom: conglutin | 15 | C | AF092846 |
| | Ara h 7 | hom: conglutin | 15 | C | AF091737 |
| | Ara h 8 | PR-10 protein | 17 | C | AY328088 |
| *Lens culinaris* | | | | | |
| lentil | Len c 1 | vicilin | 47 | C | see list of isoallergens |
| | Len c 2 | seed biotinylated prot. | 66 | P | 120C |
| *Pisum savitum* | | | | | |
| pea | Pis s 1 | vicilin | 44 | C | see list of isoallergens |
| | Pis s 2 | convicilin | 63 | C | pending |
| *Actinidia chinensis* | | | | | |
| kiwi | Act c 1 | cysteine protease | 30 | P | P00785 |
| | Act c 2 | thaumatin-like protein | 24 | P | SW: P81370, 121 |
| *Capsicum annuum* | | | | | |
| bell pepper | Cap a 1w | osmotin-like protein | 23 | C | AJ297410 |
| | Cap a 2 | profilin | 14 | C | AJ417552 |
| *Lycopersicon esculentum* | | | | | |
| tomato | Lyc e 1 | profilin | 14 | C | AJ417553 |
| | Lyc e 2 | b-fructofuranosidase | 50 | C | see isoallergen list |
| | Lyc e 3 | lipid transfer prot. | 6 | C | U81996 |
| *Solanum tuberosum* | | | | | |
| potato | Sola t 1 | patatin | 43 | P | P15476 |
| | Sola t 2 | cathepsin D inhibitor | 21 | P | P16348 |
| | Sola t 3 | cysteine protease inhibitor | 21 | P | P20347 |
| | Sola t 4 | aspartic protease inhibitor | 16 + 4 | P | P30941 |
| *Bertholletia excelsa* | | | | | |
| Brazil nut | Ber e 1 | 2S albumin | 9 | C | P04403, M17146 |
| | Ber e 2 | 11S globulin seed storage protein | 29 | C | AY221641 |
| *Juglans nigra* | | | | | |
| black walnut | Jug n 1 | 2S albumin | 19* | C | AY102930 |
| | Jug n 2 | vicilin-like prot. | 56* | C | AY102931 |
| *Juglans regia* | | | | | |
| English walnut | Jug r 1 | 2S albumin | | C | U66866 |
| | Jug r 2 | vicilin | 44 | C | AF066055 |
| | Jug r 3 | lipid transfer protein | 9 | P | Pastorello |
| *Anacardium occidentale* | | | | | |
| Cashew | Ana o 1 | vicilin-like protein | 50 | C | see isoallergen list |
| | Ana o 2 | legumin-like protein | 55 | C | AF453947 |
| | Ana o 3 | 2S albumin | 14 | C | AY081853 |
| *Ricinus communis* | | | | | |
| Castor bean | Ric c 1 | 2S albumin | | C | P01089 |
| *Sesamum indicum* | | | | | |
| sesame | Ses i 1 | 2S albumin | 9 | C | 121A, AF240005 |
| | Ses i 2 | 2S albumin | 7 | C | AF091841 |
| | Ses i 3 | 7S vicilin-like globulin | 45 | C | AF240006 |
| | Ses i 4 | oleosin | 17 | C | AAG23840 |
| | Ses i 5 | oleosin | 15 | C | AAD42942 |
| *Cucumis melo* | | | | | |
| muskmelon | Cuc m 1 | serine protease | 66 | C | D32206 |
| | Cuc m 2 | profilin | 14 | C | AY271295 |
| | Cuc m 3 | pathogenesis-rel p. PR-1 | 16* | P | P83834 |
| I. Others | | | | | |
| *Anisakis simplex* | | | | | |
| nematode | Ani s 1 | | 24 | P | 121B, A59069 |
| | Ani s 2 | paramyosin | 97 | C | AF173004 |

| ALLERGENS Species Name | Allergen Name | Biochem.ID or Obsolete name | MW | cDNA or protein | Reference, Acc. No. |
| --- | --- | --- | --- | --- | --- |
| | Ani s 3 | tropomyosin | 41 | C | 121C, Y19221 |
| | Ani s 4 | | 9 | P | P83885 |
| *Argas reflexus* pigeon tick | Arg r 1 | | 17 | C | AJ697694 |
| *Ascaris suum* worm | Asc s 1 | | 10 | P | 122 |
| *Carica papaya* papaya | Car p 3w | papain | 23.4* | C | 122A, M15203 |
| *Dendronephthya nipponica* soft coral | Den n 1 | | 53 | P | 122B |
| *Hevea brasiliensis* rubber (latex) | Hev b 1 | elongation factor | 58 | P | 123, 124 |
| | Hev b 2 | 1,3-glucanase | 34/36 | C | 125 |
| | Hev b 3 | | 24 | P | 126, 127 |
| | Hev b 4 | component of microhelix complex | 100-115 | P | 128 |
| | Hev b 5 | | 16 | C | U42640 |
| | Hev b 6.01 | hevein precursor | 20 | C | M36986, p02877 |
| | Hev b 6.02 | hevein | 5 | C | M36986, p02877 |
| | Hev b 6.03 | C-terminal fragment | 14 | C | M36986, p02877 |
| | Hev b 7.01 | hom: patatin from B-serum | 42 | C | U80598 |
| | Hev b 7.02 | hom: patatin from C-serum | 44 | C | AJ223038 |
| | Hev b 8 | profilin | 14 | C | see list of isoallergens |
| | Hev b 9 | enolase | 51 | C | AJ132580 |
| | Hev b 10 | Mn superoxide dismut. | 26 | C | see list of isoallergens |
| | Hev b 11 | class 1 chitinase | | C | see list of isoallergens |
| | Hev b 12 | lipid transfer protein | 9.3 | C | AY057860 |
| | Hev b 13 | esterase | 42 | P | P83269 |
| *Homo sapiens* human autoallergens | Hom s 1 | | 73* | C | Y14314 |
| | Hom s 2 | | 10.3* | C | X80909 |
| | Hom s 3 | | 20.1* | C | X89985 |
| | Hom s 4 | | 36* | C | Y17711 |
| | Hom s 5 | | 42.6* | C | P02538 |
| *Triplochiton scleroxylon* obeche | Trip s 1 | class 1 chitinase | 38.5 | P | Kespohl p.c. |

REFERENCES

1. Marsh, D. G., and L. R. Freidhoff. 1992. ALBE, an allergen database. IUIS, Baltimore, Md., Edition 1.0.
2. Marsh, D. G., L. Goodfriend, T. P. King, H. Lowenstein, and T. A. E. Platts-Mills. 1986. Allergen nomenclature. Bull WHO 64: 767-770.
3. King, T. P., P. S, Norman, and J. T. Cornell. 1964. Isolation and characterization of allergen from ragweed pollen. II. Biochemistry 3: 458-468.
4. Lowenstein, H.1980. Timothy pollen allergens. Allergy 35: 188-191.
5. Aukrust, L. 1980. Purification of allergens in *Cladosporium herbarum*. Allergy 35: 206-207.
6. Demerec, M., E. A. Adelberg, A. J. Clark, and P. E. Hartman. 1966. A proposal for a uniform nomenclature in bacterial genetics. Genetics 54: 61-75.
7. Bodmer, J. G., E. D. Albert, W. F. Bodmer, B. Dupont, H. A. Erlich, B. Mach, S. G. E. Marsh, W. R. Mayr, P. Parham, T. Sasuki, G. M. Th. Schreuder, J. L. Strominger, A. Svejgaard, and P. I. Terasaki. 1991. Nomenclature for factors of the HLA system, 1990. Immunogenetics 33: 301-309.
8. Griffith, I. J., J. Pollock, D. G. Klapper, B. L. Rogers, and A. K. Nault. 1991. Sequence polymorphism of Amb a I and Amb a II, the major allergens in *Ambrosia artemisiifolia* (short ragweed). Int. Arch. Allergy Appl. Immunol. 96: 296-304.
9. Roebber, M., D. G. Klapper, L. Goodfriend, W. B. Bias, S. H. Hsu, and D. G. Marsh. 1985 Immunochemical and genetic studies of Amb t V (Ra5G), an Ra5 homologue from giant ragweed pollen. J. Immunol. 134: 3062-3069.
10. Metzler, W. J., K. Valentine, M. Roebber, M. Friedrichs, D. G. Marsh, and L. Mueller. 1992. Solution structures of ragweed allergen Amb t V. Biochemistry 31: 5117-5127.
11. Metzler, W. J., K. Valentine, M. Roebber, D. G. Marsh, and L. Mueller. 1992. Proton resonance assignments and three-dimensional solution structure of the ragweed allergen Amb a V by nuclear magnetic resonance spectroscopy. Biochemistry 31: 8697-8705.
12. Goodfriend, L., A. M. Choudhury, J. Del Carpio, and T. P. King. 1979. Cytochromes C: New ragweed pollen allergens. Fed. Proc. 38: 1415.
13. Ekramoddoullah, A. K. M., F. T. Kisil, and A. H. Sehon. 1982. Allergenic cross reactivity of cytochrome c from Kentucky bluegrass and perennial ryegrass pollens. Mol. Immunol. 19: 1527-1534.
14. Ansari, A. A., E. A. Killoran, and D. G. Marsh. 1987. An investigation of human response to perennial ryegrass (*Lolium perenne*) pollen cytochrome c (Lol p X). J. Allergy Clin. Immunol. 80: 229-235.
15. Morgenstern, J. P., I. J. Griffith, A. W. Brauer, B. L. Rogers, J. F. Bond, M. D. Chapman, and M. Kuo. 1991. Amino acid sequence of Fel d I, the major allergen of the domestic cat: protein sequence analysis and cDNA cloning. Proc. Natl. Acad. Sci. USA 88: 9690-9694.
16. Griffith, I. J., S. Craig, J. Pollock, X. Yu, J. P. Morgenstern, and B. L. Rogers. 1992. Expression and genomic structure of the genes encoding FdI, the major allergen from the domestic cat. Gene 113: 263-268.
17. Weber, A., L. Marz, and F. Altmann. 1986. Characteristics of the asparagine-linked oligosaccharide from honey-bee venom phospholipase A2. Comp. Biochem. Physiol. 83B: 321-324.

18. Weber, A., H. Schroder, K. Thalberg, and L. Marz. 1987. Specific interaction of IgE antibodies with a carbohydrate epitope of honey bee venom phospholipase A2. Allergy 42: 464-470.
19. Stanworth, D. R., K. J. Dorrington, T. E. Hugli, K. Reid, and M. W. Turner. 1990. Nomenclature for synthetic peptides representative of immunoglobulin chain sequences. Bulletin WHO 68: 109-111.
20. Rafnar, T., I. J. Griffith, M. C. Kuo, J. F. Bond, B. L. Rogers, and D. G. Klapper. 1991. Cloning of Amb a I (Antigen E), the major allergen family of short ragweed pollen. J. Biol. Chem. 266: 1229-1236.
21. Rogers, B. L., J. P. Morgenstern, I. J. Griffith, X. B. Yu, C. M. Counsell, A. W. Brauer, T. P. King, R. D. Garman, and M. C. Kuo. 1991. Complete sequence of the allergen Amb a II: recombinant expression and reactivity with T cells from ragweed allergic patients. J. Immunol. 147: 2547-2552.
22. Klapper, D. G., L. Goodfriend, and J. D. Capra. 1980. Amino acid sequence of ragweed allergen $R^{a3}$. Biochemistry 19: 5729-5734.
23. Ghosh, B., M. P. Perry, T. Rafnar, and D. G. Marsh. 1993. Cloning and expression of immunologically active recombinant Amb a V allergen of short ragweed (*Ambrosia artemisiifolia*) pollen. J. Immunol. 150: 5391-5399.
24. Roebber, M., R. Hussain, D. G. Klapper, and D. G. Marsh. 1983. Isolation and properties of a new short ragweed pollen allergen, Ra6. J. Immunol. 131: 706-711.
25. Lubahn, B., and D. G. Klapper. 1993. Cloning and characterization of ragweed allergen Amb a VI (abst). J. Allergy Clin. Immunol. 91: 338.
26. Roebber, M., and D. G. Marsh. 1991. Isolation and characterization of allergen Amb a VII from short ragweed pollen. J. Allergy Clin. Immunol. 87: 324.
27 Goodfriend L, Choudhury A M, Klapper D G, Coulter K M, Dorval G, DelCarpio J, Osterland C K. Ra5G, a homologue of Ra5 in giant ragweed pollen: isolation, HLA-DR-associated activity and amino acid sequence. Mol Immunol 22: 899-906, 1985.
28 Himly M, Jahn-Schmid B, Dedic A, Kelemen P, Wopfner N, Altmann F, van Ree R, Briza P, Richter K, Ebner C, Ferreira F. Art v 1, the major allergen of mugwort pollen, is a modular glycoprotein with a defensin-like and a hydroxyproline-rich domain. FASEB J 17: 106-108, 2003.
28A Nilsen, B. M., K. Sletten, M. O'Neill, B. Smestead Paulsen, and H. van Halbeek. 1991. Structural analysis of the glycoprotein allergen Art v II from pollen of mugwort (*Artemesia vulgaris*). J. Biol. Chem. 266: 2660-2668.
29 Wopfner N, Willeroidee M, Hebenstreit D, van Ree R, Aalbers M, Briza P, Thalhamer J, Ebner C, Richter K, Ferreira F. Molecular and immunological characterization of profilin from mugwort pollen. Biol Chem 383: 1779-1789, 2002.
29A Jimenez A, Moreno C, Martinez J, Martinez A, Bartolome B, Guerra F, Palacios R 1994. Sensitization to sunflower pollen: only an occupational allergy? Int Arch Allergy Immunol 105: 297-307.
29B Barderas R, Villalba M, Lombardero M, Rodriguez R. Identification and characterization of Che a 1 allergen from *Chenopodium album* pollen. Int Arch Allergy Immunol 127: 47-54, 2002.
29C Carnes J, Fernandez-Caldas E, Casanovas M, Lahoz C, Colas C Immunochemical characterization of Salsola kali-pollen extracts. Allergy 56, Supplement 68: 274, 2001.
29D Giuliani A, Pini C, Bonini S, Mucci N, Ferroni L, Vicari G: Isolation and purification of a major allergen from *Parietaria officinalis* pollen. Allergy 42: 434-440, 1987.

Smith, P. M., Suphioglu, C., Griffith, I. J., Theriault, K., Knox, R. B. and Singh, M. B. 1996. Cloning and expression in yeast *Pichia pastoris* of a biologically active form of Cyn d 1, the major allergen of Bermuda grass pollen. J. Allergy Clin. Immunol. 98: 331-343.
31 Suphioglu, C., Ferreira, F. and Knox, R. B. 1997. Molecular cloning and immunological characterisation of Cyn d 7, a novel calcium-binding allergen from Bermuda grass pollen. FEBS Lett. 402: 167-172.
31a. Asturias J A, Arilla M C, Gomez-Bayon N, Martinez J, Martinez A, and Palacios R. 1997. Cloning and high level expression of *Cynodon* dactylon (Bermuda grass) pollen profilin (Cyn d 12) in *Escherichia coli*: purification and characterization of the allergen. Clin Exp Allergy 27: 1307-1313.
32. Mecheri, S., G. Peltre, and B. David. 1985. Purification and characterization of a major allergen from *Dactylis glomerata* pollen: The Ag Dg 1. Int. Arch. Allergy Appl. Immunol. 78: 283-289.
33. Roberts, A. M., L. J. Bevan, P. S. Flora, I. Jepson, and M. R. Walker. 1993. Nucleotide sequence of cDNA encoding the Group II allergen of Cocksfoot/Orchard grass (*Dactylis glomerata*), Dac g II. Allergy 48: 615-623.
33a. Guerin-Marchand, C., Senechal, H., Bouin, A. P., Leduc-Brodard, V., Taudou, G., Weyer, A., Peltre, G. and David, B. 1996. Cloning, sequencing and immunological characterization of Dac g 3, a major allergen from *Dactylis glomerata* pollen. Mol. Immunol. 33: 797-806.
34. Klysner, S., K. Welinder, H. Lowenstein, and F. Matthiesen. 1992. Group V allergens in grass pollen IV. Similarities in amino acid compositions and amino terminal sequences of the group V allergens from *Lolium perenne*, *Poa pratensis* and *Dactylis glomerata*. Clin. Exp. Allergy 22: 491-497.
35. Perez, M., G. Y. Ishioka, L. E. Walker, and R. W. Chesnut. 1990. cDNA cloning and immunological characterization of the rye grass allergen Lol p I. J. Biol. Chem. 265: 16210-16215.
36. Griffith, I. J., P. M. Smith, J. Pollock, P. Theerakulpisut, A. Avjioglu, S. Davies, T. Hough, M. B. Singh, R. J. Simpson, L. D. Ward, and R. B. Knox. 1991. Cloning and sequencing of Lol p I, the major allergenic protein of rye-grass pollen. FEBS Letters 279: 210-215.
37. Ansari, A. A., P. Shenbagamurthi, and D. G. Marsh. 1989. Complete amino acid sequence of a *Lolium perenne* (perennial rye grass) pollen allergen, Lol p II. J. Biol. Chem. 264: 11181-11185.
37a. Sidoli, A., Tamborini, E., Giuntini, I., Levi, S., Volonte, G., Paini, C., De Lalla, C., Siccardi, A. G., Baralle, F. E., Galliani, S, and Arosio, P. 1993. Cloning, expression, and immunological characterization of recombinant *Lolium perenne* allergen Lol p II. J. Biol. Chem. 268: 21819-21825.
38. Ansari, A. A., P. Shenbagamurthi, and D. G. Marsh. 1989. Complete primary structure of a *Lolium perenne* (perennial rye grass) pollen allergen, Lol p III: Comparison with known Lol p I and II sequences. Biochemistry 28: 8665-8670.
39. Singh, M. B., T. Hough, P. Theerakulpisut, A. Avjioglu, S. Davies, P. M. Smith, P. Taylor, R. J. Simpson, L. D. Ward, J. McCluskey, R. Puy, and R. B. Knox. 1991. Isolation of cDNA encoding a newly identified major allergenic protein of rye-grass pollen: Intracellular targeting to the amyloplost. Proc. Natl. Acad. Sci. 88: 1384-1388.
39a. van Ree R, Hoffman D R, van Dijk W, Brodard V, Mahieu K, Koeleman C A, Grande M, van Leeuwen W A, Aalberse R C. 1995. Lol p XI, a new major grass pollen 39. allergen, is a member of a family of soybean trypsin inhibitor-related proteins. J Allergy Clin Immunol 95: 970-978.
40. Suphioglu, C. and Singh, M. B. 1995. Cloning, sequencing and expression in *Escherichia coli* of Pha a 1 and four isoforms of Pha a 5, the major allergens of canary grass pollen. Clin. Exp. Allergy 25: 853-865.
41 Dolecek, C., Vrtala, S., Laffer, S., Steinberger, P., Kraft, D., Scheiner, O. and Valenta, R. 1993. Molecular characterization of Phl p II, a major timothy grass (*Phleum pratense*) pollen allergen. FEBS Lett. 335: 299-304.
41A Fischer S, Grote M, Fahlbusch B, Muller W D, Kraft D, Valenta R. 1996. Characterization of Phl p 4, a major timothy grass (*Phleum pratense*) pollen allergen. J Allergy Clin Immunol 98: 189-198.
42 Matthiesen, F., and H. Lowenstein. 1991. Group V allergens in grass pollens. I. Purification and characterization of the group V allergen from *Phleum pratense* pollen, Phl p V. Clin. Exp. Allergy 21: 297-307.
43 Petersen, A., Bufe, A., Schramm, G., Schlaak, M. and Becker, W. M. 1995. Characterization of the allergen group VI in timothy grass pollen (Phl p 6). II. cDNA cloning of Phl p 6 and structural comparison to grass group V. Int. Arch. Allergy Immunol. 108: 55-59.
43A Marknell DeWitt A, Niederberger V, Lehtonen P, Spitzauer S, Sperr W R, Valent P, Valenta R, Lidholm J. Molecular and immunological characterization of a novel timothy grass (*Phleum pratense*) pollen allergen, Phl p 11. Clin Exp Allergy 32: 1329-1340, 2002.
44 Valenta, R., Ball, T., Vrtala, S., Duchene, M., Kraft, D. and Scheiner, 0. 1994. cDNA cloning and expression of timothy grass (*Phleum pratense*) pollen profilin in *Escherichia coli*: comparison with birch pollen profilin. Biochem. Biophys. Res. Commun. 199: 106-118.
46 Esch, R. E., and D. G. Klapper. 1989. Isolation and characterization of a major cross-reactive grass group I allergenic determinant. Mol. Immunol. 26: 557-561.
47. Olsen, E., L. Zhang, R. D. Hill, F. T. Kisil, A. H. Sehon, and S. Mohapatra. 1991. Identification and characterization of the Poa p IX group of basic allergens of Kentucky bluegrass pollen. J. Immunol. 147: 205-211.
48. Avjioglu, A., M. Singh, and R. B. Knox. 1993. Sequence analysis of Sor h I, the group I allergen of Johnson grass pollen and it comparison to rye-grass Lol p I (abst). J. Allergy Clin. Immunol. 91: 340.
52. Kos T, Hoffmann-Sommergruber K, Ferreira F, Hirschwehr R, Ahorn H, Horak F, Jager S, Sperr W, Kraft D, Scheiner O. 1993. Purification, characterization and N-terminal amino acid sequence of a new major allergen from European chestnut pollen-Cas s 1. Biochem Biophys Res Commun 196: 1086-92.
53. Diaz-Perales A, Lombardero M, Sanchez-Monge R, Garcia-Selles F J, Pernas M, Fernandez-Rivas M, Barber D, Salcedo G. 2000. Lipid-transfer proteins as potential plant panallergens: cross-reactivity among proteins of *Artemisia* pollen, Castaneae nut and Rosaceae fruits, with different IgE-binding capacities. Clin Exp Allergy 30: 1403-1410.
54. Ipsen, H., and O. C. Hansen. 1991. The $NH_2$-terminal amino acid sequence of the immuno-chemically partial identical major allergens of alder (*Alnus glutinosa*) Aln g I, birch (*Betula verrucosa*) Bet v I, hornbeam (*Carpinus betulus*) Car b I and oak (*Quercus alba*) Que a I pollens. Mol. Immunol. 28: 1279-1288.
55. Taniai, M., S. Ando, M. Usui, M. Kurimoto, M. Sakaguchi, S. Inouye, and T. Matuhasi. 1988. N-terminal amino acid sequence of a major allergen of Japanese cedar pollen (Cry j I). FEBS Lett. 239: 329-332.
56. Griffith, I. J., A. Lussier, R. Garman, R. Koury, H. Yeung, and J. Pollock. 1993. The cDNA cloning of Cry j I, the major allergen of *Cryptomeria japonica* (Japanese cedar) (abst). J. Allergy Clin. Immunol. 91: 339.
57. Sakaguchi, M., S. Inouye, M. Taniai, S. Ando, M. Usui, and T. Matuhasi. Identification of the second major allergen of Japanese cedar pollen. Allergy 45: 309-312, 1990.
57A Yokoyama M, Miyahara M, Shimizu K, Kino K, Tsunoo H. Purification, identification, and cDNA cloning of Jun a 2, the second major allergen of mountain cedar pollen. Biochem Biophys Res Commun 275: 195-202, 2000.
57B Midoro-Horiuti T, Goldblum R M, Kurosky A, Wood T G, Brooks E G. Variable Expression of Patho-genesis-Related Protein Allergen in Mountain Cedar (*Juniperus ashei*) Pollen. J Immunol 164: 2188-2192, 2000.
57C Tinghino R., Barletta B., Palumbo S., Afferni C., Iacovacci P., Mari A., Di Felice G., Pini, C. Molecular characterization of a cross-reactive *Juniperus* oxycedrus pollen allergen, Jun o 2: a novel calcium-binding allergen J. Allergy Clin. Immunol. 101: 772-777, 1998.
58 Gross G N, Zimburean J M, Capra J D. Isolation and partial characterization of the allergen in mountain cedar pollen. Scand J Immunol 8: 437-441, 1978.
58A Obispo T M, Melero J A, Carpizo J A, Carreira J, Lombardero M. The main allergen of *Olea europaea* (Ole e I) is also present in other species of the oleaceae family. Clin Exp Allergy 23: 311-316, 1993.
58B Midoro-Horiuti T, Goldblum R M, Brooks E G. Identification of mutations in the genes for the pollen allergens of eastern red cedar (*Juniperus virginiana*). Clin Exp Allergy 31: 771-778, 2001.
59 Lombardero M., Barbas J. A., Moscoso del Prado J., Carreira J. cDNA sequence analysis of the main olive allergen, Ole e I. Clin. Exp. Allergy 24: 765-770, 1994.
60 Villalba, M., E. Batanero, C. Lopez-Otin, L. M. Sanchez, R. I. Monsalve, M. A. Gonzalez de la Pena, C. Lahoz, and R. Rodriguez. Amino acid sequence of Ole e I, the major allergen from olive tree pollen (*Olea europaea*). Eur. J. Biochem. 216: 863-869, 1993.
60A Asturias J A, Arilla M C, Gomez-Bayon N, Martinez J, Martinez A, Palacios R. Cloning and expression of the panallergen profilin and the major allergen (Ole e 1) from olive tree pollen. J Allergy Clin Immunol 100: 365-372, 1997.
60B Batanero E, Villalba M, Ledesma A Puente X S, Rodriguez R. Ole e 3, an olive-tree allergen, belongs to a widespread family of pollen proteins. Eur J Biochem 241: 772-778, 1996.
60C Batanero E, Ledesma A, Villalba M, Rodriguez R. Purification, amino acid sequence and immunological characterization of Ole e 6, a cysteine-enriched allergen from olive tree pollen. FEBS Lett. 410: 293-296, 1997.
60D Tejera M L, Villalba M, Batanero E, Rodriguez R. Identification, isolation, and characterization of Ole e 7, a new allergen of olive tree pollen. J Allergy Clin Immunol 104: 797-802, 1999.
60E Ledesma A, Villalba M, Rodriguez R. Cloning, expression and characterization of a novel four EF-hand Ca(2+)-binding protein from olive pollen with allergenic activity. FEBS Lett 466: 192-196, 2000.
60F Barral P, Batanero E, Palomares O, Quiralte J, Villalba M, Rodriguez R. A major allergen from pollen defines a novel family of plant proteins end shows intra- and interspecies [correction of interspecie] cross-reactivity. J Immunol 172: 3644-3651, 2004.
61 Yi F C, Cheong N, Shek P C, Wang D Y, Chua K Y, Lee B W. Identification of shared and unique immunoglobulin E epitopes of the highly conserved tropomyosins in *Blomia tropicalis* and *Dermatophagoides pteronyssinus*. Clin Exp Allergy 32: 1203-1210, 2002.

61A Ramos J D, Cheong N, Lee B W, Chua K Y. cDNA cloning and expression of Blo t 11, the *Blomia tropicalis* allergen homologous to paramyosin. Int Arch Allergy Immunol 126: 286-293, 2001.

62 Chua, K. Y., G. A. Stewart, and W. R. Thomas. Sequence analysisof cDNA encoding for a major house dust mite allergen, Der p I. J. Exp. Med. 167: 175-182, 1988.

62A Chua, K. Y., C. R. Doyle, R. J. Simpson, K. J. Turner, G. A. Stewart, and W. R. Thomas. Isolation of cDNA coding for the major mite allergen Der p II by IgE plaque immunoassay. Int. Arch. Allergy Appl. Immunol. 91: 118-123, 1990.

62B Smith A M, Benjamin D C, Derewenda U, Smith W A, Thomas W R, Chapman M D. Sequence polymorphisms and antibody binding to the group 2 dust mite allergens. Int Arch Allergy Immunol 124: 61-63, 2001.

62C Smith A M, Benjamin D C, Hozic N, Derewenda U, Smith W A, Thomas W R, Gafvelin G, van Hage-Hamsten M, Chapman M D. The molecular basis of antigenic cross-reactivity between the group 2 mite allergens. J Allergy Clin Immunol 107: 977-984, 2001.

63 Smith W A, Thomas W R. Comparative analysis of the genes encoding group 3 allergens from *Dermatophagoides pteronyssinus* and *Dermatophagoides farinae*. Int Arch Allergy Immunol 109: 133-140, 1996.

64 Lake, F. R., L. D. Ward, R. J. Simpson, P. J. Thompson, and G. A. Stewart. House dust mite-derived amylase: Allergenicity and physicochemical characterisation. J. Allergy Clin. Immunol. 87: 1035-1042, 1991.

65 Tovey, E. R., M. C. Johnson, A. L. Roche, G. S. Cobon, and B. A. Baldo. Cloning and sequencing of a cDNA expressing a recombinant house dust mite protein that binds human IgE and corresponds to an important low molecular weight allergen. J. Exp. Med. 170: 1457-1462, 1989.

66 Yasueda, H., T. Shida, T. Ando, S. Sugiyama, and H. Yamakawa. 1991. Allergenic and proteolytic properties of fourth allergens from *Dermatophagoides* mites. In: "Dust Mite Allergens and Asthma. Report of the 2nd international workshop" A. Todt, Ed., UCB Institute of Allergy, Brussels, Belgium, pp. 63-64.

67 Shen, H.-D., K.-Y. Chua, K.-.L. Lin, K.-H. Hsieh, and W. R. Thomas. Molecular cloning of a house dust mite allergen with common antibody binding specificities with multiple components in mite extracts. Clin. Exp. Allergy 23: 934-940, 1993.

67A O'Neil G M, Donovan G R, Baldo B A. Cloning and charaterisation of a major allergen of the house dust mite *Dermatophagoides pteronyssinus*, homologous with glutathione 5-transferase. Biochim Bio-phys Acta, 1219: 521-528, 1994.

67B King C, Simpson R J, Moritz R L, Reed G E, Thompson P J, Stewart G A. The isolation and characterization of a novel collagenolytic serine protease allergen (Der p 9) from the dust mite *Dermatophagoides pteronyssinus*. J Allergy Clin Immunol 98: 739-747, 1996.

68 Lind P, Hansen O C, Horn N. The binding of mouse hybridoma and human IgE antibodies to the major fecal allergen, Der p I of *D. pteronyssinus*. J. Immunol. 140: 4256-4262, 1988.

69 Dilworth, R. J., K. Y. Chua, and W. R. Thomas. Sequence analysis of cDNA coding for a mojor house dust allergn Der f I. Clin. Exp. Allergy 21: 25-32, 1991.

70 Nishiyama, C., T. Yunki, T. Takai, Y. Okumura, and H. Okudaira. Determination of three disulfide bonds in a major house dust mite allergen, Der f II. Int. Arch. Allergy Immunol. 101: 159-166, 1993.

70A Trudinger, M., K. Y. Chua, and W. R. Thomas. cDNA encoding the major dust mite allergen Der f II. Clin. Exp. Allergy 21: 33-38, 1991.

71 Shen H D, Chua K Y, Lin W L, Hsieh K H, Thomas W R. Molecular cloning and immunological characterization of the house dust mite allergen Der f 7. Clin Exp Allergy 25: 1000-1006, 1995.

71A Tategaki A, Kawamoto S, Aki T, Jyo T, Suzuki O, Shigeta S, Ono K. Newly described house dust mite allergens. ACI International suppl. 1: 74-76, 2000.

72 Aki T, Kodama T, Fujikawa A, Miura K, Shigeta S, Wada T, Jyo T, Murooka Y, Oka S, Ono K. Immunochemical characteristion of recombinant and native tropomyosins as a new allergen from the house dust mite *Dermatophagoides farinae*. J Allergy Clin Immunol 96: 74-83, 1995.

72A Tsai L, Sun Y, Chao P, Ng H, Hung M, Hsieh K, Liaw S, Chua K. Sequence analysis and expression of a cDNA clone encoding a 98-kDa allergen in *Dermatophagoides farinae*. Clin Exp Allergy 29: 1606-1613, 1999.

72B Gafvelin G, Johansson E, Lundin A, Smith A M, Chapman M D, Benjamin D C, Derewenda U, Van Hage-Hamsten M. Cross-reactivity studies of a new group 2 allergen from the dust mite *Glycyphagus domesticus*, Gly d 2, and group 2 allergens from *Dermatophagoides pteronyssinus, Lepidoglyphus destructor*, and *Tyrophagus putrescentiae* with recombinant allergens. J Allergy Clin Immunol 107: 511-518, 2001.

73 van Hage-Hamsten, M., T. Bergman, E. Johansson, B. Persson, H. Jornvall, B. Harfast, and S. G. O. Johansson. N-terminal amino acid sequence of major allergen of the mite *lepidoglyphus destructor* (abst). J. Allergy Clin. Immunol. 91: 353, 1993.

74 Varela J, Ventas P, Carreira J, Barbas J A, Gimenez-Gallego G, Polo F. Primary structure of Lep d I, the main *Lepidoglyphus destructor* allergen. Eur J Biochem 225: 93-98, 1994.

74A Schmidt M, van der Ploeg I, Olsson S, van Hage Hamsten M. The complete cDNA encoding the *Lepidoglyphus destructor* major allergen Lep d 1. FEBS Lett 370: 11-14, 1995.

75 Eriksson T L J, Rasool O, Huecas S, Whitley P, Crameri R, Appenzeller U, Gafvelin G, van Hage-Hamsten M. Cloning of three new allergens from the dust mite *Lepidoglyphus destructor* using phage surface display technology. Eur. J. Biochem. 268: 287-294, 2001.

75A Saarne T, Kaiser L, Rasool 0, Huecas S, van Hage-Hamsten M, Gafvelin G: Cloning and characterisation of two IgE-binding proteins, homologous to tropomyosin and α-tubulin, from the mite *Lepidoglyphus destructor*. Int Arch Allergy Immunol 130: 258-265, 2003.

75B Eriksson T L, Johansson E, Whitley P, Schmidt M, Elsayed S, van Hage-Hamsten M. Cloning and characterisation of a group II allergen from the dust mite *Tyrophagus putrescentiae*. Eur. J. Biochem. 251 (1-2), 443-447, 1998.

76. Rautiainen J, Rytkonen M, Pelkonen J, Pentikainen J, Perola O, Virtanen T, Zeiler T, Mantyjarvi R. BDA20, a major bovine dander allergen characterized at the sequence level is Bos d 2. Submitted.

77. Gjesing B, Lowenstein H. Immunochemistry of food antigens. Ann Allergy 53: 602, 1984.

78. de Groot, H., K. G. H. Goei, P. van Swieten, and R. C. Aalberse. Affinity purification of a major and a minor allergen from dog extract: Serologic activity of affiity-purified Can f I and Can f I-depleted extract. J. Allergy Clin. Immunol. 87: 1056-1065, 1991.

79. Konieczny, A. Personal communication; Immunologic Pharmaceutical Corp.

79A. Bulone, V. Separation of horse dander allergen proteins by two-dimensional electrophoresis. Molecular characterisation and identification of Equ c 2.0101 and Equ c 2.0102 as lipocalin proteins. Eur J Biochem 253: 202-211, 1998.

79B. Swiss-Prot acc. P81216, P81217.

79C. Dandeu J. P., Rabillon J., Divanovic A., Carmi-Leroy A., David B. (1993). Hydrophobic interaction chromatography for isolation and purification of Equ c 1, the horse major allergen. J. Chromatogr. 621: 23-31.

79D. Goubran Botros H., Rabillon J., Gregoire C., David B., Dandeu J. P. 1998. Thiophilic absorption chromatography: purification of Equ c 2 and Equ c 3, two horse allergens from horse sweat. J. Chromatogr. B 710: 57-65.

79E. Hilger C, Kohnen M, Grigioni F, Lehners C, Hentges F. Allergic cross-reactions between cat and pig serum albumin. Allergy 52: 179-187, 1997; and Hilger C, Grigioni F, Hentges F. Sequence of the gene encoding cat (Felts domesticus) serum albumin. Gene 169: 295-296, 1996.

79F. Ichikawa K, Vailes L D, Pomes A, Chapman M D. Molecular cloning, expression and modeling of cat allergen, cystatin (Fel d 3), a cysteine protease inhibitor. Clin Exp Allergy, In Press 2001.

80 Fahlbusch B, Rudeschko O, Szilagyi U, Schlott B, Henzgen M, Schlenvoigt G, Schubert H. Purification and partial characterization of the major allergen, Cav p 1, from guinea pig *Cavia porcellus*. Allergy 57: 417-422, 2002.

81 McDonald, B., M. C. Kuo, J. L. Ohman, and L. J. Rosenwasser. 1988. A 29 amino acid peptide derived from rat alpha 2 euglobulin triggers murine allergen specific human T cells (abst). J. Allergy Clin. Immunol. 83: 251.

81A Clarke, A. J., P. M. Cissold, R. A. Shawi, P. Beattie, and J. Bishop. 1984. Structure of mouse urinary protein genes: differential splicing configurations in the 3'-non-coding region. EMBO J. 3: 1045-1052.

82. Longbottom, J. L. 1983. Chracterization of allergens from the urines of experimental animals. McMillan Press, London, pp. 525-529.

83. Laperche, Y., K. R. Lynch, K. P. Dolans, and P. Feigelsen. 1983. Tissue-specific control of alpha 2u globulin gene expression: constitutive synthesis in submaxillary gland. Cell 32: 453-460.

83A. Bush R K, Sanchez H, Geisler D. 1999. Molecular cloning of a major *Alternaria alternata* allergen, rAlt a 2. J Allergy Clin Immunol 104: 665-671.

83B. Aukrust L, Borch S M. 1979. Partial purification and characterization of two *Cladosporium* herbarum allergens. Int Arch Allergy Appl Immunol 60: 68-79.

83C. Sward-Nordmo M, Paulsen B S, Wold J K. 1988. The glycoprotein allergen Ag-54 (Cla h II) from *Cladosporium herbarum*. Structural studies of the carbohydrate moiety. Int Arch Allergy Appl Immunol 85: 288-294.

84 Shen, et al. J. Allergy Clin. Immunol. 103: S157, 1999.

84A Crameri R. Epidemiology and molecular basis of the involvement of *Aspergillus fumigatus* in allergic diseases. Contrib. Microbiol. Vol. 2, Karger, Basel (in press).

84B Shen, et al. (manuscript submitted), 1999

84C Shen H D, Ling W L, Tan M F, Wang S R, Chou H, Han S I H. Vacuolar serine proteinase: A major allergen of *Aspergillus fumigatus*. 10th International Congress of Immunology, Abstract, 1998.

85 Kumar A, Reddy L V, Sochanik A, Kurup V P. 1993. Isolation and characterization of a recombinant heat shock protein of *Aspergillus fumigatus*. J. Allergy Clin. Immunol. 91: 1024-1030.

85A Saxena S, Madan T, Muralidhar K, Sarma P U. 2003. cDNA cloning, expression and characterization of an allergenic L3 ribosomal protein of *Aspergillus fumigatus*. Clin Exp Immunol 134: 86-91.

85B Baur X, Melching-Kollmuss S, Koops F, Strassburger K, Zober A. IgE-mediated allergy to phytase—a new animal feed additive. Allergy 57: 943-945, 2002.

86A Shen H D, Lin W L, Tsai J J, Liaw S F, Han S H. 1996. Allergenic components in three different species of *Penicillium*: crossreactivity among major allergens. Clin Exp Allergy 26: 444-451.

86B. Shen, et al. Abstract; The XVIII Congress of the European Academy of Allergology and Clinical Immunology, Brussels, Belgium, 3-7 Jul. 1999.

87 Shen H D, Lin W L, Tam M F, Wang S R, Tzean S S, Huang M H, Han S H. Characterization of allergens from *Penicillium oxalicum* and *P. notatum* by immunoblotting and N-terminal amino acid sequence analysis. Clin Exp Allergy 29: 642-651, 1999.

87A Shen H D, Liaw S F, Lin W L, Ro L H, Yang H L, Han S H. Molecular cloning of cDNA coding for the 68 kDa allergen of *Penicillium notatum* using MoAbs. Clin Exp Allergy 25: 350-356, 1995.

87B Shen H D, Wang C W, Lin W L, Lai H Y, Tam M F, Chou H, Wang S R, Han S H. cDNA cloning and immunologic characterization of Pen o 18, the vacuolar serine protease major allergen of *Penicillium oxalicum*. J Lab Clin Med 137: 115-124, 2001.

88 Woodfolk J A, Wheatley L M, Piyasena R V, Benjamin D C, Platts-Mills T A. 1998. *Trichophyton* antigens associated with IgE antibodies and delayed type hypersensitivity. Sequence homology to two families of serine proteinases. J Biol Chem 273: 29489-96.

88A Deuell, B., L. K. Arruda, M. L. Hayden, M. D. Chapman and T. A. E. Platts-Mills. 1991. *Trichophyton tonsurans* Allergen I. J. Immunol. 147: 96-101.

89 Shen, H. D., K. B. Choo, H. H. Lee, J. C. Hsieh, and S. H. Han. 1991. The 40 kd allergen of *Candida albicans* is an alcohol dehydrogenease: molecular cloning and immunological analysis using monoclonal antibodies. Clin. Exp. Allergy 21: 675-681.

89A Horner W E, Reese G, Lehrer S B. 1995. Identification of the allergen Psi c 2 from the basidiomycete *Psilocybe cubensisas* a fungal cyclophilin Int Arch Allergy Immunol 107: 298-300.

89B Chang C Y, Chou H, Tam M F, Tang R B, Lai H Y, Shen H D. Characterization of Enolase Allergen from *Rhodotorula mucilaginosa*. J Biomed Sci 9: 645-655, 2002.

90 Yasueda H, Hashida-Okado T, Saito A, Uchida K, Kuroda M, Onishi Y, Takahashi K, Yamaguchi H, Takesako K, Akiyama K. Identification and cloning of two novel allergens from the lipophilic yeast, *Malassezia furfur*. Biochem Biophys Res Commun 248: 240-244, 1998. NB: strain TIMM2782 (Teikyo University Institute for Medical Mycology) equal to strain CBS1878 (Central Bureau von Schimmelkulturen).

90A Onishi Y, Kuroda M, Yasueda H, Saito A, Sono-Koyama E, Tunasawa S, Hashida-Okado T, Yagihara T, Uchida K, Yamaguchi H, Akiyama K, Kato I, Takesako K. Two-dimensional electrophoresis of *Malassezia* allergens for atopic dermatitis and isolation of Mal f 4 homologs with mitochondrial malate dehydrogenase. Eur J Biochem 261: 148-154, 1999. NB: strain TIMM2782 (Teikyo University Institute for Medical Mycology) equal to strain CBS1878 (Central Bureau von Schimmelkulturen).

91 Schmidt M, Zargari A, Holt P, Lindbom L, Hellman U, Whitley P, van der Ploeg I, Harfast B, Scheynius A. The complete cDNA sequence and expression of the first major allergenic protein of *Malassezia furfur*, Mal f 1. Eur J Biochem 246: 181-185, 1997. NB: strain ATCC no. 42132 (American Type Culture Collection).

91A Rasool O, Zargari A, Almqvist J, Eshaghi H, Whitley P, Scheynius A. Cloning, characterization and expression of complete coding sequences of three IgE binding *Malassezia furfur* allergens, Mal f 7, Mal f 8 and Mal f 9. Eur J Biochem 267: 4355-4361, 2000. NB: strain ATCC no. 42132 (American Type Culture Collection).

91B NB: strain 4625 (Indian Agricultural Research Institute, PUSA; New Delhi, India).

92 Kuchler, K., M. Gmachl, M. J. Sippl, and G. Kreil. 1989. Analysis of the cDNA for phospholipase A2 from honey bee venom glands: The deduced amino acid sequence reveals homology to the corresponding vertebrate enzymes. Eur. J. Biochem. 184: 249-254.

93 Gmachl, M., and G. Kreil. 1993. Bee venom hyaluronidase is homologous to a membrane protein of mammalian sperm. Proc. Natl. Acad. Sci. USA 90: 3569-3573.

93A Hoffman D R. 1977. Allergens in bee venom III. Identification of allergen B as an acid phosphatase. J. Allergy Clin. Immunol. 59: 364-366.

94 Habermann, E. 1972. Bee and wasp venoms. Science 177: 314-322.

95 Hoffman D R, Jacobson R S. 1996. Allergens in *Hymenoptera* venom XXVII: Bumblebee venom allergy and allergens. J. Allergy Clin. Immunol. 97: 812-821.

95A Hoffman D R, El-Choufani A E, Smith M M, de Groot H.2001. Occupational allergy to bumblebee venom: Allergens of *Bombus terrestris*. J Allergy Clin Immunol In press.

95B Helm R, Cockrell G, Stanley J S, Brenner R J, Burks W, Bannon G A. 1996. Isolation snd characterization of a clone encoding a majore allergen (Bla g Bd90K) involved in IgE mediated cockroach hypersensitivity. J Allerg Clin Immunol 98: 172-180.

95C Pomes A, Melen E, Vailes L D, Retief J D, Arruda L K, Chapman M D. 1998. Novel allergen structures with tandem amino acid repeats derived from German and American cockroach. J Biol Chem 273: 30801-30807.

96 Arruda L K, Vailes L D, Mann B J, Shannon J, Fox J W, Vedvick T S, Hayden M L, Chapman M D. Molecular cloning of a major cockroach (*Blattella germanica*) allergen, Bla g 2. Sequence homology to the aspartic proteases. Biol Chem 270: 19563-19568, 1995.

97 Arruda L K, Vailes L D, Hayden M L, Benjamin D C, Chapman M D. Cloning of cockroach allergen, Bla g 4, identifies ligand binding proteins (or calycins) as a cause of IgE antibody responses. J Biol Chem 270: 31196-31201, 1995.

98 Arruda L K, Vailes L D, Benjamin D C, Chapman M D. Molecular cloning of German Cockroach (*Blattella germanica*) allergens. Int Arch Allergy Immunol 107: 295-297, 1995.

98A Wu C M, Wang N M, Lee M F, Kao C Y Y, Luo S F. 1998. Cloning of the American cockroach Cr-PII allergens: Evidence for the existence of cross-reactive allergens between species. J Allergy Clin Immunol 101: 832-840.

98B Melen E, Pomes A, Vailes L D, Arruda L K, Chapman M D. 1999. Molecular cloning of Per a 1 and definition of the cross-reactive Group 1 cockroach allergens. J Allergy Clin Immunol 103: 859-64.

98C Wu C H, Lee M F, Liao S C, Luo S F. Sequencing analysis of cDNA clones encoding the American cockroach Cr-PI allergens. J Biol Chem 271: 17937-17943, 1996.

98D Wu C H, Lee M F, Wang N M, Luo S F. Sequencing and immunochemical characterization of the American cockroach Per a 3 (Cr-PI) isoallergenic variants. Molecular Immunol 34: 1-8, 1997.

98E Santos A B R, Chapman M D, Aalberse R C, Vailes L D, Ferriani V P L, Oliver C, Rizzo M C, Naspitz C K, Arruda L K. 1999. Cockroach allergens and asthma in Brazil: Identification of tropomyosin as a major allergen with potential cross-reactivity with mite and shrimp allergens. J Allergy Clin Immunol 104: 329-337.

98F Asturias J A, Gomez-Bayon N, Arilla M C, Martinez A, Palacios R, Sanchez-Gascon, Martinez J. 1999. Molecular characterization of American cockroach tropomyosin (*Periplaneta americana* allergen 7), a cross-reactive allergen. J Immunol 162: 4342-4348.

99 Mazur, G., X. Baur, and V. Liebers. 1990. Hypersensitivity to hemoglobins of the Diptera family Chironomidae: Structural and functional studies of their immunogenic/allergenic sites. Monog. Allergy 28: 121-137.

99A Moneo I, Vega J M, Caballero M L, Vega J, Alday E. Isolation and characterization of Tha p 1, a major allergen from the pine processionary caterpillar *Thaumetopoea pityocampa*. Allergy 58: 34-37, 2003.

100 Soldatova, L., L. Kochoumian, and T. P. King. 1993. Sequence similarity of a hornet (*D. maculata*) venom allergen phospholipase A1 with mammalian lipases. FEBS Letters 320: 145-149.

101 Lu, G., L. Kochoumian and T. P. King. Whiteface hornet venom allergen hyaluronidase: cloning and its sequence similarity with other proteins (abst.). 1994. J. Allergy Clin. Immunol. 93: 224.

102 Fang, K. S. F., M. Vitale, P. Fehlner, and T. P. King. 1988. cDNA cloning and primary structure of a white-faced hornet venom allergen, antigen 5. Proc. Natl. Acad. Sci., USA 85: 895-899.

103 King, T. P., D. C. Moran, D. F. Wang, L. Kochoumian, and B. T. Chait. 1990. Structural studies of a hornet venom allergen antigen 5, Dol m V and its sequence similarity with other proteins. Prot. Seq. Data Anal. 3: 263-266.

104. Lu, G., M. Villalba, M. R. Coscia, D. R. Hoffman, and T. P. King. 1993. Sequence analysis and antigen cross reactivity of a venom allergen antigen 5 from hornets, wasps and yellowjackets. J. Immunol. 150: 2823-2830.

105. King, T. P. and Lu, G. 1997. Unpublished data.

105A. King T P, Lu G, Gonzalez M, Qian N and Soldatova L. 1996. Yellow jacket venom allergens, hyaluronidase and phospholipase: sequence similarity and antigenic cross-reactivity with their hornet and wasp homologs and possible implications for clinical allergy. J. Allergy Clin. Immunol. 98: 588-600.

106. Hoffman, D. R. 1993. Allergens in *hymenoptera* venom XXV: The amino acid sequences of antigen 5 molecules and the structural basis of antigenic cross-reactivity. J. Allergy Clin. Immunol. 92: 707-716.

107. Hoffman D R. 1992. Unpublished data.

108. Hoffman D R. The complete amino acid sequence of a yellowjacket venom phospholipase (abst). J. Allergy Clin. Immunol. 91: 187, 1993.

109. Jacobson R S, Hoffman D R, Kemeny D M. The cross-reactivity between bee and vespid hyaluronidases has a structural basis (abst). J. Allergy Clin. Immunol. 89: 292, 1992.

110. Hoffman D R. Allergens in *Hymenoptera* venom XXIV: The amino acid sequences of imported fire ant venom allergens Sol i II, Sol i III, and Sol i IV. J. Allergy Clin. Immunol 91: 71-78, 1993.

111. Schmidt M, Walker R B, Hoffman D R, McConnell T J. Nucleotide sequence of cDNA encoding the fire ant venom protein Sol i II. FEBS Letters 319: 138-140, 1993.

111A. Paddock C D, McKerrow J H, Hansell E, Foreman K W, Hsieh I, Marshall N. Identification, cloning, and recombinant expression of procalin, a major triatomine allergen. J Immunol 167: 2694-2699, 2001.

112. Elsayed S, Bennich H. The primary structure of Allergen M from cod. Scand J Immunol 3: 683-686, 1974.

113. Elsayed S, Aas K, Sletten K, Johansson S G O. Tryptic cleavage of a homogeneous cod fish allergen and isolation of two active polypeptide fragments. Immunochemistry 9: 647-661, 1972.

114. Hoffman, D. R. 1983. Immunochemical identification of the allergens in egg white. J. Allergy Clin. Immunol. 71: 481-486.

115. Langeland, T. 1983. A clinical and immunological study of allergy to hen's egg white. IV. specific IgE antibodies to individual allergens in hen's egg white related to clinical and immunolgical parameters in egg-allergic patients. Allergy 38: 493-500.

116 Daul C B, Slattery M, Morgan J E, Lehrer S B. 1993. Common crustacea allergens: identification of B cell epitopes with the shrimp specific monoclonal antibodies. In: "Molecular Biology and Immunology of Allergens" (D. Kraft and A. Sehon, eds.). CRC Press, Boca Raton. pp. 291-293.

116A Shanti K N, Martin B M, Nagpal S, Metcalfe D D, Subba Rao P V. *Identification* of tropomyosin as the major shrimp allergen and characterization of its IgE-binding epitopes. J. Immunol. 151: 5354-5363, 1993.

117 Yu C J, Lin Y F, Chiang B L, Chow L P. Proteomics and Immunological Analysis of a Novel Shrimp Allergen, Pen m 2. J Immunol 170: 445-453, 2003.

117A Miyazawa M, Fukamachi H, Inagaki Y, Reese G, Daul C B, Lehrer S B, Inouye S, Sakaguchi M. Identification of the first major allergen of a squid (Todarodes pacificus). J. Allergy Clin. Immunol. 98: 948-953, 1996.

117B Asturias J A, Eraso E, Arilla M C, Gomez-Bayon N, Inacio F, Martinez A. Cloning, isolation, and IgE-binding properties of *Helix aspersa* (brown garden snail) tropomyosin. Int Arch Allergy Immunol 128: 90-96, 2002.

117C Lopata A L, Zinn C, Potter P C. Characteristics of hypersensitivity reactions and identification of a unique 49 kd IgE-binding protein (Hal-m−1) in abalone (Haliotis cnidae). J. Allergy Clin. Immunol. 100: 642-648, 1997.

117D Hoffmann-Sommergruber K, O'Riordain G, Ahorn H, Ebner C, Laimer Da Camara Mechado M, Puhringer H, Scheiner O, Breiteneder H. Molecular characterization of Dau c 1, the Bet v 1 homologous protein from carrot and its cross-reactivity with Bet v 1 and Api g 1. Clin. Exp. Allergy 29: 840-847, 1999.

118 Monsalve R I, Gonzalez de la Pena M A, Menendez-Arias L, Lopez-Otin C, Villalba M, Rodriguez R. Characterization of a new mustard allergen, Bra j IE. Detection of an allergenic epitope. Biochem. J. 293: 625-632 1993.

118A. Monsalve R I, Gonzalez de la Pena M A, Lopez-Otin C, Fiandor A, Fernandez C, Villalba M, Rodriguez R. 1997. Detection, isolation and complete amino acid sequence of an aeroallergenic protein from rapeseed flour. Clin Exp Allergy 27: 833-841.

119. Mena, M., R. Sanchez-Monge, L. Gomez, G. Salcedo, and P. Carbonero. A major barley allergen associated with baker's asthma disease is a glycosylated monomeric inhibitor of insect alpha-amylase: cDNA cloning and chromosomal location of the gene. Plant Molec. Biol. 20: 451-458, 1992.

119A. Palosuo K, Varjonen E, Kekki O M, Klemola T, Kalkkinen N, Alenius H, Reunala T. Wheat omega-5 gliadin is a major allergen in children with immediate allergy to ingested wheat. J. Allergy Clin. Immunol. 108: 634-638, 2001.

119B. Xu H, Theerakulpisut P, Goulding N, Suphioglu C, Singh M. B. Bhalla P. L. Cloning expression and immunological characterization of Ory s 1, the major allergen of rice pollen. Gene 164: 255-259, 1995.

119C. Pastorello E A, Ortolani C, Farioli L, Pravettoni V, Ispano M, Borga A, Bengtsson A, Incorvaia C, Berti C, Zanussi C. Allergenic cross-reactivity among peach, apricot, plum, and cherry in patients with oral allergy syndrome: an in vivo and in vitro study. J. Allergy Clin. Immunol. 94: 699-707, 1994.

119D. Diaz-Perales A, Tabar A I, Sanchez-Monge R, Garcia B E, Gomez B, Barber D, Salcedo G. Characterization of asparagus allergens: a relevant role of lipid transfer proteins. J Allergy Clin Immunol 110: 790-796, 2002.

119E Galleguillos F, Rodriguez J C. Asthma caused by bromelin inhalation. Clin Allergy 8: 21-24, 1978.

119F Baur X. Studies on the specificity of human IgE-antibodies to the plant proteases papain and bromelain. Clin Allergy 9: 451-457, 1979.

119G Gailhofer G, Wilders-Truschnig M, Smolle J, Ludvan M. Asthma caused by bromelain: an occupational allergy. Clin Allergy 18: 445-450, 1988.

120. Menendez-Arias, L., I. Moneo, J. Dominguez, and R. Rodriguez. 1988. Primary structure of the major allergen of yellow mustard (*Sinapis alba* L.) seed, Sin a I. Eur. J. Biochem. 177: 159-166.

120A Gonzalez R, Varela J, Carreira J, Polo F. Soybean hydrophobic protein and soybean hull allergy. Lancet 346: 48-49, 1995.

120B Kleine-Tebbe J, Vogel L, Crowell D N, Haustein U F, Vieths S. Severe oral allergy syndrome and anaphylactic reactions caused by a Bet v 1-related PR-10 protein in soybean, SAM22. J Allergy Clin Immunol 110: 797-804, 2002.

120C Sanchez-Monge R, Pascual C Y, Diaz-Perales A, Fernandez-Crespo J, Martin-Esteban M, Salcedo G. Isolation and characterization of relevant allergens from boiled lentils. J. Allergy Clin. Immunol. 106: 955-961, 2000.

121 Gavrovic-Jankulovic M, cIrkovic T, Vuckovic O, Atanaskovic-Markovic M, Petersen A, Gojgic G, Burazer L, Jankov R M. Isolation and biochemical characterization of a thaumatin-like kiwi allergen. J Allergy Clin Immunol 110: 805-810, 2002.

121A Pastorello E A, Varin E, Farioli L, Pravettoni V, Ortolani C, Trambaioli C, Fortunato D, Giuffrida M G, Rivolta F, Robino A, Calamari A M, Lacava L, Conti A. The major allergen of sesame seeds (Sesamum indicum) is a 2S albumin. J. Chromatogr. B Biomed. Sci. Appl. 756: 85-93, 2001.

121B Moneo I, Caballero M L, Gomez F, Ortega E, Alonso M J. Isolation and characterization of a major allergen from the fish parasite *Anisakis simplex*. J. Allergy Clin. Immunol. 106: 177-182, 2000.

121C Asturias J A, Eraso E, Martinez A. 2000. Is tropomysoin an allergen in Anisakis? Allergy 55: 898-890.

122 Christie, J. F., B. Dunbar, I. Davidson, and M. W. Kennedy. 1990. N-terminal amino acid sequence identity between a major allergen of *Ascaris lumbricoides* and *Ascaris suum* and MHC-restricted IgE responses to it. Immunology 69: 596-602.

122A Baur X, Konig G, Bencze K, Fruhmann G. Clinical symptoms and results of skin test, RAST and bronchial provocation test in thirty-three papain workers: evidence for strong immunogenic potency and clinically relevant 'proteolytic effects of airborne papain'. Clin Allergy 12: 9-17, 1982.

122B Onizuka R, Kamiya H, Muramoto K, Goto R, Inoue K, Kumamoto K, Nakajima Y, Lida S, Ishigami F. Purification of the major allergen of red soft coral (Dendronephthya nipponica). Int Arch Allergy Immunol 125: 135-143, 2001.

123. Czuppon A B, Chen Z, Rennert S, Engelke T, Meyer H E, Heber M, Baur X. The rubber elongation factor of rubber trees (*Hevea brasiliensis*) is the major allergen in latex. J Allergy Clin Immunol 92: 690-697, 1993.

124. Attanayaka D P S T G, Kekwick R G O, Franklin F C H. 1991. Molecular cloning and nucleotide sequencing of the rubber elongation factor gene from *hevea brasiliensis*. Plant Mol Biol 16: 1079-1081.

125. Chye M L, Cheung K Y. 1995. J 1,3-glucanase is highly expressed in Laticifers of *Hevea brasiliensis*. Plant Mol Biol 26: 397-402.

126. Alenius H, Palosuo T, Kelly K, Kurup V, Reunala T, Makinen-Kiljunen S, Turjanmaa K Fink J. 1993. IgE reactivity to 14-kD and 27-kD natural rubber proteins in Latex-allergic children with Spina bifida and other congenital anomalies. Int Arch Allergy Immunol 102: 61-66.

127. Yeang H Y, Cheong K F, Sunderasan E, Hamzah S, Chew N P, Hamid S, Hamilton R G, Cardosa M J. 1996. The 14.6 kD (REF, Hey b 1) and 24 kD (Hey b 3) rubber particle proteins are recognized by IgE from Spina Bifida patients with Latex allergy. J Allerg Clin Immunol in press.

128. Sunderasan E, Hamzah S, Hamid S, Ward M A, Yeang H Y, Cardosa M J. 1995. Latex B-serum J-1,3-glucanase (Hey b 2) and a component of the microhelix (Hey b 4) are major Latex allergens. J nat Rubb Res 10: 82-99.

TABLE 4

Inhibition of allergic patients' IgE-binding to rBet v 1 by IgG antibodies raised with CFA adsorbed proteins

| Patient | OD values nrs | OD values rαBet v 1 | % inhibition rαBet v 1 | OD values nrs | OD values αBet v 1rs 1 | % inhibition αBet v 1rs1 | OD values nrs | OD values αBet v 1rs 2 | % inhibition αBet v 1rs2 | OD values nrs | αBet v 1mosaic | % inhibition αBet v 1mosaic |
|---|---|---|---|---|---|---|---|---|---|---|---|---|
| 1 | 0.111 | 0.066 | 40.5 | 0.121 | 0.037 | 69.5 | 0.13 | 0.036 | 72 | 0.131 | 0.044 | 66.5 |
| 2 | 0.353 | 0.15 | 57.5 | 0.404 | 0.082 | 79.7 | 0.433 | 0.071 | 83.5 | 0.477 | 0.117 | 75.5 |
| 3 | 1.055 | 0.269 | 74.5 | 1.193 | 0.06 | 95 | 1.248 | 0.049 | 96 | 1.445 | 0.085 | 94 |
| 4 | 0.306 | 0.093 | 69.6 | 0.336 | 0.038 | 89 | 0.357 | 0.035 | 90 | 0.391 | 0.047 | 88 |
| 5 | 0.508 | 0.14 | 72.5 | 0.612 | 0.052 | 91.5 | 0.657 | 0.049 | 92.5 | 0.674 | 0.061 | 91 |
| 6 | 3.211 | 0.466 | 85.5 | 3.335 | 0.095 | 98 | 3.471 | 0.047 | 98.5 | 3.601 | 0.408 | 89 |
| 7 | 1.662 | 0.483 | 71 | 1.902 | 0.074 | 96 | 2.026 | 0.063 | 97 | 2.098 | 0.154 | 93 |
| 8 | 0.125 | 0.086 | 31 | 0.14 | 0.033 | 76.5 | 0.142 | 0.033 | 77 | 0.149 | 0.045 | 70 |
| 9 | 0.991 | 0.374 | 62 | 0.442 | 0.128 | 71 | 0.452 | 0.092 | 79.6 | 0.466 | 0.171 | 64 |
| 10 | 1.571 | 0.315 | 80 | 1.546 | 0.063 | 96 | 1.817 | 0.04 | 98 | 1.977 | 0.219 | 89 |
| 11 | 0.582 | 0.245 | 58 | 0.655 | 0.039 | 94 | 0.689 | 0.027 | 96 | 0.704 | 0.074 | 89.5 |
| 12 | 1.32 | 0.154 | 88.5 | 1.641 | 0.063 | 96 | 1.833 | 0.048 | 97 | 2.051 | 0.109 | 95 |
| 13 | 1.424 | 0.361 | 74.7 | 1.573 | 0.048 | 97 | 1.682 | 0.038 | 98 | 1.705 | 0.12 | 99.5 |
| 14 | 0.158 | 0.127 | 19.6 | 0.16 | 0.06 | 62.5 | 0.177 | 0.061 | 65.5 | 0.198 | 0.068 | 66 |
| 15 | 0.098 | 0.057 | 41.8 | 0.106 | 0.046 | 56.5 | 0.111 | 0.045 | 59.5 | 0.111 | 0.047 | 58 |
| 16 | 0.617 | 0.073 | 88 | 0.738 | 0.049 | 93 | 0.805 | 0.047 | 94 | 0.805 | 0.086 | 89 |
| 17 | 0.523 | 0.134 | 74.4 | 0.546 | 0.048 | 91 | 0.586 | 0.041 | 93 | 0.602 | 0.071 | 88 |
| 18 | 0.118 | 0.083 | 29.7 | 0.126 | 0.035 | 72 | 0.135 | 0.033 | 75.5 | 0.144 | 0.04 | 72 |
| % mean inhibition | | | 62 | | | 85 | | | 87 | | | 82 | nrs, rabbit pre-immune sera;
rαBet v 1, rabbit IgG antibody raised against rBet v 1;
rαBet v 1-rs1, rabbit IgG antibody raised against rBet v 1-rs1;
rαBet v 1-rs2, rabbit IgG antibody raised against rBet v 1-rs2;
rαBet v 1-mosaic, rabbit IgG antibody raised against rBet v 1-mosaic.
(1-18), birch pollen allergic patients.
OD values correspond to the amounts of bound IgE antibodies and percentages (%) inhibition of patients' IgE-binding to rBet v 1 obtained with each antiserum versus the pre-immune sera as well as the mean inhibition values are displayed.

TABLE 5

Inhibition of allergic patients' IgE-binding to rBet v 1 by IgG antibodies raised with Al(OH)₃ adsorbed proteins

| Patient | OD values nrs | OD values rαBet v 1 | % inhibition rαBet v 1 | OD values nrs | OD values αBet v 1rs 1 | % inhibition αBet v 1rs1 | OD values nrs | OD values αBet v 1rs 2 | % inhibition αBet v 1rs2 | OD values nrs | αBet v 1mosaic | % inhibition αBet v 1mosaic |
|---|---|---|---|---|---|---|---|---|---|---|---|---|
| 1 | 0.471 | 0.268 | 43.1 | 0.536 | 0.241 | 55 | 0.529 | 0.359 | 32.1 | 0.553 | 0.07 | 87.3 |
| 2 | 0.153 | 0.132 | 13.7 | 0.142 | 0.128 | 9.8 | 0.141 | 0.126 | 10.6 | 0.86 | 0.608 | 6 |
| 3 | 1.674 | 0.535 | 68 | 1.874 | 0.415 | 77.8 | 1.885 | 1.043 | 44.7 | 2.128 | 0.102 | 95.2 |
| 4 | 0.621 | 0.218 | 73.5 | 0.926 | 0.189 | 79.6 | 0.924 | 0.497 | 46.2 | 0.95 | 0.073 | 92.3 |
| 5 | 0.769 | 0.269 | 65 | 0.933 | 0.211 | 77.4 | 0.932 | 0.798 | 14.4 | 0.953 | 0.087 | 90.9 |
| 6 | 3.448 | 1.426 | 58.6 | 3.447 | 2.393 | 30.6 | 0.091 | 0.065 | 28.6 | 3.42 | 0.143 | 95.9 |
| 7 | 0.739 | 0.348 | 53 | 0.794 | 0.259 | 67.4 | 0.813 | 0.477 | 41.3 | 0.096 | 0.054 | 44.9 |
| 8 | 0.274 | 0.191 | 3.01 | 0.291 | 0.118 | 59.4 | 0.298 | 0.199 | 33.2 | 0.317 | 0.052 | 83.6 |
| 9 | 0.088 | 0.063 | 28.4 | 1.171 | 0.667 | 43 | 1.12 | 0.94 | 16.1 | 1.153 | 0.329 | 71.5 |

TABLE 5-continued

Inhibition of allergic patients' IgE-binding to rBet v 1 by IgG antibodies raised with Al(OH)₃ adsorbed proteins

| Patient | OD values nrs | OD values rαBet v 1 | % inhibition rαBet v 1 | nrs | OD values αBet v 1rs 1 | % inhibition αBet v 1rs1 | nrs | OD values αBet v 1rs 2 | % inhibition αBet v 1rs2 | nrs | OD values αBet v 1mosaic | % inhibition αBet v 1mosaic |
|---|---|---|---|---|---|---|---|---|---|---|---|---|
| 10 | 2.676 | 0.774 | 71.1 | 2.906 | 0.903 | 68.9 | 3.125 | 2.088 | 33.2 | 3.167 | 0.115 | 96.4 |
| 11 | 1.39 | 0.694 | 50.1 | 1.51 | 0.44 | 70.9 | 1.535 | 0.889 | 42.1 | 1.587 | 0.05 | 96.8 |
| 12 | 3.629 | 0.348 | 90.4 | 3.619 | 1.026 | 71.6 | 3.63 | 1.985 | 45.3 | 3.618 | 0.11 | 96.9 |
| 13 | 2.566 | 0.675 | 73.7 | 2.876 | 0.7 | 75.7 | 2.949 | 1.582 | 46.3 | 2.929 | 0.141 | 95.2 |
| 14 | 0.218 | 0.097 | 55.5 | 0.234 | 0.065 | 72.2 | 0.342 | 0.126 | 63.1 | 0.237 | 0.043 | 81.8 |
| 15 | 0.302 | 0.145 | 52 | 0.31 | 0.114 | 63.2 | 0.324 | 0.178 | 45.1 | 0.331 | 0.107 | 67.7 |
| 16 | 1.397 | 0.183 | 87 | 1.529 | 0.415 | 72.8 | 1.49 | 0.833 | 44.1 | 1.563 | 0.142 | 91 |
| 17 | 1.02 | 0.289 | 71.6 | 1.113 | 0.308 | 72.3 | 1.157 | 0.665 | 42.5 | 1.155 | 0.095 | 91.8 |
| 18 | 0.306 | 0.137 | 55.2 | 0.329 | 0.1 | 69.6 | 0.318 | 0.182 | 42.8 | 0.332 | 0.096 | 71.1 |
| % mean inhibition | | | 58 | | | 59 | | | 37 | | | 81 | nrs, rabbit pre-immune sera;
rαBet v 1, rabbit IgG antibody raised against rBet v 1;
rαBet v 1-rs1, rabbit IgG antibody raised against rBet v 1-rs1;
rαBet v 1-rs2, rabbit IgG antibody raised against rBet v 1-rs2;
rαBet v 1-mosaic, rabbit IgG antibody raised against rBet v 1-mosaic.
(1-18), birch pollen allergic patients.
OD values correspond to the amounts of bound IgE antibodies and percentages (%) inhibition of patients' IgE-binding to rBet v 1 obtained with each antiserum versus the pre-immune sera as well as the mean inhibition values are displayed.

TABLE 6

Demographic, serologic, and clinical characterization of the individuals

| | Sex/Age | Birch pollen related symptoms | Type of treatment | IgE CAP (kUA/L) Birch | IgE CAP (kUA/L) rBet v 1 | Total IgE (kU/L) | Other allergies |
|---|---|---|---|---|---|---|---|
| Allergic Subjects | | | | | | | |
| 1 | M/56 | RC, AD, AS, OAS | AH, TCt | 15.7 | 14.6 | 860 | a, g, pf, npf, mo, mi |
| 2 | M/44 | RC, AD | AH | 27.4 | 27.1 | 69.3 | pf |
| 3 (C) | M/28 | RC, AD | AH, TCt, SIT | 76.4 | 16.84 | >5000 | a, g, pf, npf, mo, mi, w |
| 4 (H) | M/27 | RC, AD | AH, TCt | 15.4 | 10.1 | 281 | a, pf, mi |
| 5 | M/47 | RC, AD, OAS | no | 25.6 | 20.2 | 114 | a, g, pf, mi |
| 6 | M/38 | RC, AD | AH, TCt | >200 | >200 | >10000 | a, g, pf, npf, mo, mi, w |
| 7 | F/46 | RC, AD | TCt | >100 | 26 | >5000 | a, g, pf, npf, mo, mi, w |
| 8 | M | RC, AD | AH, TCt, UV | 12 | 13.66 | 3674 | a, g, pf, npf, mi, w |
| 9 | F/42 | RC, AD, AS | AH, SIT | 145.4 | 47.8 | >10000 | a, g, pf, npf, mi, w |
| 10 (F) | M/29 | RC | AH | 98.1 | >100 | 760 | a, g, pf, npf, mo, mi, w |
| 11 | F | RC, AD | no | 170.6 | 85.2 | 6192 | a, g, pf, npf, mo, mi, w |
| 12 | F/46 | RC, AS, OAS | no | 57.5 | 60.5 | 466 | a, g, pf, mi |
| 13 (A) | F/30 | RC, OAS | AH | >100 | >100 | >5000 | a, g, pf, npf, mo, mi, w |
| 14 (B) | M/29 | RC | no | 12.4 | 10.4 | 285 | pf |
| 15 (E) | M/42 | RC | no | 1.01 | 1 | 36.1 | mi |
| 16 (D) | F/30 | RC | no | 4.87 | 3.41 | 144 | a, g, pf, npf, mi |
| 17 | M/47 | RC, OAS | no | 37.1 | 28.7 | 144 | a, g, pf, mo, w |
| 18 | M/52 | RC | AH, BD, TCt | 36.9 | 36 | 115 | pf |
| 19 | M/51 | RC | AH, TCt | 8.45 | 7.41 | 29.7 | g, pf, mi |
| (G) | M/32 | RC | AH, SIT | 6.61 | 3.88 | 102 | a, g, pf, npf, mi, mo, w |
| (I) | M/23 | RC | AH | 24.8 | 21.7 | 233 | a, g, pf, npf, mo, mi, w |
| (J) | F/30 | RC, AD, AS, OAS | AH, BD | 58.7 | 47 | 4886 | a, pf, mo, w |
| Non-Allergic Subjects | | | | | | | |
| 20 | F/28 | — | no | <0.35 | <0.35 | <2.00 | 0 |
| 21 | F/34 | — | no | <0.35 | <0.35 | 2.65 | 0 |

(A-J) represent the subjects studied by CD203c expression experiments
M, male;
F, female,
RC, rhinoconjunctivitis;
AD, atopic dermatitis;
AS, asthma;
OAS, oral allergy syndrome
AH, antihistamines;
BD, bronchodilator;

TABLE 6-continued

| | | | IgE CAP (kUA/L) | | | |
|---|---|---|---|---|---|---|
| Sex/Age | Birch pollen related symptoms | Type of treatment | Birch | rBet v 1 | Total IgE (kU/L) | Other allergies |

TCt, topical corticosteroids;
SIT, specific-immunotherapy;
UV, ultraviolet-light therapy;
no, no therapy at the time of analysis
a, animals;
g, grass;
pf, plant food;
npf, non-plant-derived food;
mo, molds;
mi, mites;
w, weeds,
0, no allergy

What is claimed:

1. A hypoallergenic mosaic antigen assembled from all of the amino acids comprising a naturally-occurring allergen, though rearranged into a different order, wherein said mosaic allergen is designed to retain at least one T-cell epitope specific to said naturally-occurring allergen and is capable of inducing IgG antibodies that hinder IgE binding to said naturally-occurring allergen, wherein said naturally-occurring allergen is the major birch pollen allergen Bet v 1 and the amino acid sequence of said mosaic antigen comprises SEQ ID NO: 15, SEQ ID NO: 17, or SEQ ID NO: 19.

2. The hypoallergenic mosaic antigen of claim 1, wherein said antigen is obtained by (a) cleaving the naturally-occurring allergen into two or three peptide fragments, wherein said fragments are selected for their reduced allergenic activity as compared to that of the naturally-occurring allergen; and (b) reassembling the peptide fragments to yield an amino acid sequence that is different from that of the naturally-occurring allergen.

3. The mosaic antigen of claim 2, wherein said peptide fragments are non-overlapping.

4. The hypoallergenic mosaic antigen according to claim 1, wherein said different order arises from exchanging an allergen fragment that includes the naturally-occurring N-terminus with an allergen fragment that includes the naturally-occurring C-terminus.

5. The mosaic antigen of claim 1, wherein said mosaic antigen has reduced allergenic activity as compared to the naturally-occurring allergen.

6. The mosaic antigen of claim 5, wherein the IgE reactivity of the mosaic antigen is no more than 10% of an IgE reactivity value obtained for the naturally-occurring allergen.

7. The mosaic antigen of claim 5, wherein the IgE reactivity of the mosaic antigen is no more than 5% of an IgE reactivity value obtained for the naturally-occurring allergen.

8. The mosaic antigen of claim 1, wherein the mosaic antigen is capable of inducing allergen-specific IgG antibodies that recognize the naturally-occurring allergen and inhibit recognition of the naturally-occurring allergen by serum IgE from allergic patients.

9. An immunogenic composition for the treatment of an allergic disorder characterized in that it comprises the hypoallergenic mosaic antigen of claim 1.

10. A method for treating an allergic disorder comprising the step of administering the mosaic antigen of claim 1 to a subject in need thereof.

11. The method of claim 10, wherein the allergic disorder is a pollen allergy.

12. The method of claim 10, wherein the allergic disorder is a birch pollen allergy.

13. The method of claim 10, wherein the allergic disorder is caused by reaction to the major birch pollen allergen Bet v 1.

14. The mosaic antigen of claim 1, wherein the amino acid sequence of the mosaic antigen comprises SEQ ID NO: 15.

15. The mosaic antigen of claim 1, wherein the amino acid sequence of the mosaic antigen comprises SEQ ID NO: 17.

16. The mosaic antigen of claim 1, wherein the amino acid sequence of the mosaic antigen comprises SEQ ID NO: 19.

* * * * *

SEQUENCE LISTING

```
<160> NUMBER OF SEQ ID NOS: 23

<210> SEQ ID NO 1
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Val Pro Lys Val Thr Phe Thr Val Glu Lys Gly Ser Asn Glu Lys
1               5                   10                  15

His Leu Ala Val Leu Val Lys Tyr Glu Gly Asp Thr Met Ala Glu Val
            20                  25                  30

Glu Leu Phe Arg Phe Leu Thr Glu Lys Gly Met Lys Asn Val Phe Asp
        35                  40                  45

Asp Val Val Pro Glu Lys Tyr Thr Ile Gly Ala Thr Tyr Ala Pro Glu
    50                  55                  60

Glu Arg Glu His Gly Ser Asp Glu Trp Val Ala Met Thr Lys Gly Glu
65                  70                  75                  80

Gly Gly Val Trp Thr Phe Asp Ser Glu Glu Pro Leu Gln Gly Pro Phe
                85                  90                  95

Asn His His His His His His
            100

<210> SEQ ID NO 2
<211> LENGTH: 309
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(309)

<400> SEQUENCE: 2 atg gtc ccg aag gtg acg ttc acg gtg gag aag ggg tcc aac gag aag       48
Met Val Pro Lys Val Thr Phe Thr Val Glu Lys Gly Ser Asn Glu Lys
1               5                   10                  15 cac ctg gcg gtg ctg gtg aag tac gag ggg gac acc atg gcg gag gtg       96
His Leu Ala Val Leu Val Lys Tyr Glu Gly Asp Thr Met Ala Glu Val
```

-continued

```
                20                  25                  30
gag ctc ttc cgg ttc ctc acc gag aag ggc atg aag aac gtc ttc gac         144
Glu Leu Phe Arg Phe Leu Thr Glu Lys Gly Met Lys Asn Val Phe Asp
            35                  40                  45 gac gtc gtc cca gag aag tac acc att ggg gcc acc tac gcg cca gaa         192
Asp Val Val Pro Glu Lys Tyr Thr Ile Gly Ala Thr Tyr Ala Pro Glu
 50                  55                  60 gag cgg gag cac ggc tcc gac gag tgg gtc gcc atg acc aag ggg gag         240
Glu Arg Glu His Gly Ser Asp Glu Trp Val Ala Met Thr Lys Gly Glu
 65                  70                  75                  80 ggc ggc gtg tgg acg ttc gac agc gag gag ccg ctc cag ggg ccc ttc         288
Gly Gly Val Trp Thr Phe Asp Ser Glu Glu Pro Leu Gln Gly Pro Phe
                85                  90                  95 aac cac cac cac cac cac cac                                             309
Asn His His His His His His
            100

<210> SEQ ID NO 3
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Val Pro Lys Val Thr Phe Thr Val Glu Lys Gly Ser Asn Glu Lys His
 1               5                  10                  15

Leu Ala Val Leu Val Lys Tyr Glu Gly Asp Thr Met Ala Glu Val Glu
            20                  25                  30

Leu Cys

<210> SEQ ID NO 4
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Arg Glu His Gly Ser Asp Glu Trp Val Ala Met Thr Lys Gly Glu Gly
 1               5                  10                  15

Gly Val Trp Thr Phe Asp Ser Glu Glu Pro Leu Gln Gly Pro Phe Asn
            20                  25                  30

Cys

<210> SEQ ID NO 5
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Cys Phe Arg Phe Leu Thr Glu Lys Gly Met Lys Asn Val Phe Asp Asp
 1               5                  10                  15

Val Val Pro Glu Lys Tyr Thr Ile Gly Ala Thr Tyr Ala Pro Glu Glu
            20                  25                  30

<210> SEQ ID NO 6
<211> LENGTH: 34
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggatttccat atggtcccga aggtgacgtt cacg                              34

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggtgaggaac cggaagagct ccacctccgc catggt                            36

<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gcggaggtgg agctcttccg gttcctcacc gagaag                            36

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggagccgtgc tcccgctctt ctggcgcgta ggtggc                            36

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tacgcgccag aagagcggga gcacggctcc gacgag                            36

<210> SEQ ID NO 11
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cgcgaattct cagtggtggt ggtggtggtg gttgaagggc ccctggagcg g           51

<210> SEQ ID NO 12
<211> LENGTH: 51
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 12
cgcgaattct cagtggtggt ggtggtggtg ctcttctggc gcgtaggtgg c            51

<210> SEQ ID NO 13
<211> LENGTH: 160
<212> TYPE: PRT
<213> ORGANISM: Betula sp.

<400> SEQUENCE: 13

Met Gly Val Phe Asn Tyr Glu Thr Glu Thr Thr Ser Val Ile Pro Ala
1               5                   10                  15

Ala Arg Leu Phe Lys Ala Phe Ile Leu Asp Gly Asp Asn Leu Phe Pro
            20                  25                  30

Lys Val Ala Pro Gln Ala Ile Ser Ser Val Glu Asn Ile Glu Gly Asn
        35                  40                  45

Gly Gly Pro Gly Thr Ile Lys Lys Ile Ser Phe Pro Glu Gly Phe Pro
    50                  55                  60

Phe Lys Tyr Val Lys Asp Arg Val Asp Glu Val Asp His Thr Asn Phe
65                  70                  75                  80

Lys Tyr Asn Tyr Ser Val Ile Glu Gly Gly Pro Ile Gly Asp Thr Leu
                85                  90                  95

Glu Lys Ile Ser Asn Glu Ile Lys Ile Val Ala Thr Pro Asp Gly Gly
            100                 105                 110

Ser Ile Leu Lys Ile Ser Asn Lys Tyr His Thr Lys Gly Asp His Glu
        115                 120                 125

Val Lys Ala Glu Gln Val Lys Ala Ser Lys Glu Met Gly Glu Thr Leu
    130                 135                 140

Leu Arg Ala Val Glu Ser Tyr Leu Leu Ala His Ser Asp Ala Tyr Asn
145                 150                 155                 160

<210> SEQ ID NO 14
<211> LENGTH: 483
<212> TYPE: DNA
<213> ORGANISM: Betula sp.

<400> SEQUENCE: 14
atgggtgttt tcaattacga aactgagacc acctctgtta tcccagcagc tcgactgttc      60
aaggccttta tccttgatgg cgataatctc tttccaaagg ttgcacccca agccattagc     120
agtgttgaaa acattgaagg aaatggaggg cctggaacca ttaagaagat cagctttccc     180
gaaggcttcc ctttcaagta cgtgaaggac agagttgatg aggtggacca cacaaacttc     240
aaatacaatt acagcgtgat cgagggcggt cccataggcg acacattgga agatctcc       300 aacgagataa agatagtggc aacccctgat ggagatccat cttgaagat cagcaacaag      360 taccacacca aggtgaccat gaggtgaag gcagagcagg ttaaggcaag taaagaaatg      420
ggcgagacac ttttgagggc cgttgagagc tacctcttgg cacactccga tgcctacaac    480
taa                                                                   483

<210> SEQ ID NO 15
<211> LENGTH: 160
<212> TYPE: PRT
<213> ORGANISM: Artificial Sequence
<220> FEATURE:
<223> OTHER INFORMATION: Description of Artificial Sequence: Synthetic
      polypeptide
```

-continued

<400> SEQUENCE: 15

Met Val Asp His Thr Asn Phe Lys Tyr Asn Tyr Ser Val Ile Glu Gly
1               5                   10                  15

Gly Pro Ile Gly Asp Thr Leu Glu Lys Ile Ser Asn Glu Ile Lys Ile
            20                  25                  30

Val Ala Thr Pro Asp Gly Gly Ser Ile Leu Lys Ile Ser Asn Lys Tyr
        35                  40                  45

His Thr Lys Gly Asp His Glu Val Lys Ala Glu Gln Val Lys Ala Ser
    50                  55                  60

Lys Glu Met Gly Glu Thr Leu Leu Arg Ala Val Glu Ser Tyr Leu Leu
65                  70                  75                  80

Ala His Ser Asp Ala Tyr Asn Gly Val Phe Asn Tyr Glu Thr Glu Thr
                85                  90                  95

Thr Ser Val Ile Pro Ala Ala Arg Leu Phe Lys Ala Phe Ile Leu Asp
            100                 105                 110

Gly Asp Asn Leu Phe Pro Lys Val Ala Pro Gln Ala Ile Ser Ser Val
        115                 120                 125

Glu Asn Ile Glu Gly Asn Gly Gly Pro Gly Thr Ile Lys Lys Ile Ser
    130                 135                 140

Phe Pro Glu Gly Phe Pro Phe Lys Tyr Val Lys Asp Arg Val Asp Glu
145                 150                 155                 160

<210> SEQ ID NO 16
<211> LENGTH: 483
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
atggtggacc acacaaactt caaatacaat tacagcgtga tcgagggcgg tcccataggc      60
gacacattgg agaagatctc caacgagata aagatagtgg caacccctga tggaggatcc     120
atcttgaaga tcagcaacaa gtaccacacc aaaggtgacc atgaggtgaa ggcagagcag     180
gttaaggcaa gtaaagaaat gggcgagaca cttttgaggg ccgttgagag ctacctcttg     240
gcacactccg atgcctacaa cggtgttttc aattacgaaa ctgagaccac ctctgttatc     300
ccagcagctc gactgttcaa ggcctttatc cttgatggcg ataatctctt tccaaaggtt     360
gcaccccaag ccattagcag tgttgaaaac attgaaggaa atggagggcc tggaaccatt     420
aagaagatca gctttcccga aggcttccct ttcaagtacg tgaaggacag agttgatgag     480
taa                                                                   483

<210> SEQ ID NO 17
<211> LENGTH: 160
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Asp Gly Gly Ser Ile Leu Lys Ile Ser Asn Lys Tyr His Thr Lys
1               5                   10                  15

Gly Asp His Glu Val Lys Ala Glu Gln Val Lys Ala Ser Lys Glu Met
            20                  25                  30

Gly Glu Thr Leu Leu Arg Ala Val Glu Ser Tyr Leu Leu Ala His Ser

```
                    35                  40                  45
Asp Ala Tyr Asn Gly Val Phe Asn Tyr Glu Thr Glu Thr Ser Val
 50                  55                  60
Ile Pro Ala Ala Arg Leu Phe Lys Ala Phe Ile Leu Asp Gly Asp Asn
 65                  70                  75                  80
Leu Phe Pro Lys Val Ala Pro Gln Ala Ile Ser Ser Val Glu Asn Ile
                     85                  90                  95
Glu Gly Asn Gly Gly Pro Gly Thr Ile Lys Lys Ile Ser Phe Pro Glu
                    100                 105                 110
Gly Phe Pro Phe Lys Tyr Val Lys Asp Arg Val Asp Glu Val Asp His
                    115                 120                 125
Thr Asn Phe Lys Tyr Asn Tyr Ser Val Ile Glu Gly Pro Ile Gly
                    130                 135                 140
Asp Thr Leu Glu Lys Ile Ser Asn Glu Ile Lys Ile Val Ala Thr Pro
145                 150                 155                 160

<210> SEQ ID NO 18
<211> LENGTH: 483
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
atggatggag gatccatctt gaagatcagc aacaagtacc acaccaaagg tgaccatgag      60
gtgaaggcag agcaggttaa ggcaagtaaa gaaatgggcg agacactttt gagggccgtt     120
gagagctacc tcttggcaca ctccgatgcc tacaacggtg ttttcaatta cgaaactgag     180
accacctctg ttatcccagc agctcgactg ttcaaggcct ttatccttga tggcgataat     240
ctctttccaa aggttgcacc ccaagccatt agcagtgttg aaaacattga aggaaatgga     300
gggcctggaa ccattaagaa gatcagctttt cccgaaggct cccttttcaa gtacgtgaag     360
gacagagttg atgaggtgga ccacacaaac ttcaaataca attacagcgt gatcgagggc     420
ggtcccatag cgacacatt ggagaagatc tccaacgaga taaagatagt ggcaaccct     480 taa                                                                   483

<210> SEQ ID NO 19
<211> LENGTH: 160
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Asp Gly Gly Ser Ile Leu Lys Ile Ser Asn Lys Tyr His Thr Lys
 1               5                  10                  15
Gly Asp His Glu Val Lys Ala Glu Gln Val Lys Ala Ser Lys Glu Met
                 20                  25                  30
Gly Glu Thr Leu Leu Arg Ala Val Glu Ser Tyr Leu Leu Ala His Ser
                 35                  40                  45
Asp Ala Tyr Asn Pro Glu Gly Phe Pro Phe Lys Tyr Val Lys Asp Arg
 50                  55                  60
Val Asp Glu Val Asp His Thr Asn Phe Lys Tyr Asn Tyr Ser Val Ile
 65                  70                  75                  80
Glu Gly Gly Pro Ile Gly Asp Thr Leu Glu Lys Ile Ser Asn Glu Ile
                 85                  90                  95
```

```
Lys Ile Val Ala Thr Pro Gly Val Phe Asn Tyr Glu Thr Glu Thr Thr
            100                 105                 110

Ser Val Ile Pro Ala Ala Arg Leu Phe Lys Ala Phe Ile Leu Asp Gly
        115                 120                 125

Asp Asn Leu Phe Pro Lys Val Ala Pro Gln Ala Ile Ser Ser Val Glu
    130                 135                 140

Asn Ile Glu Gly Asn Gly Gly Pro Gly Thr Ile Lys Lys Ile Ser Phe
145                 150                 155                 160

<210> SEQ ID NO 20
<211> LENGTH: 483
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
atggatggag gatccatctt gaagatcagc aacaagtacc acaccaaagg tgaccatgag      60
gtgaaggcag agcaggttaa ggcaagtaaa gaaatgggcg agacactttt gagggccgtt    120
gagagctacc tcttggcaca ctccgatgcc tacaaccccg aaggcttccc tttcaagtac    180
gtgaaggaca gagttgatga ggtggaccac acaaacttca atacaattca gcgtgatc     240 gagggcggtc ccataggcga cacattggag aagatctcca acgagataaa gatagtggca    300 accctggtg ttttcaatta cgaaactgag accacctctg ttatcccagc agctcgactg    360
ttcaaggcct ttatccttga tggcgataat ctctttccaa aggttgcacc ccaagccatt    420
agcagtgttg aaaacattga aggaaatgga gggcctggaa ccattaagaa gatcagcttt    480
taa                                                                   483

<210> SEQ ID NO 21
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Leu Phe Pro Lys Val Ala Pro Gln Ala Ile Ser Ser Val Glu Asn Ile
1               5                   10                  15

Glu Gly Asn Gly Gly Pro Pro Thr Ile Lys Lys Ile Ser Phe
            20                  25                  30

<210> SEQ ID NO 22
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Glu Asp Val His Thr Asn Phe Lys Tyr Asn Tyr Ser Val Ile Glu Gly
1               5                   10                  15

Gly Pro Ile Gly Asp Thr Leu Glu Lys Ile Ser Asn Glu Ile Lys
            20                  25                  30

<210> SEQ ID NO 23
<211> LENGTH: 6
<212> TYPE: PRT
```

-continued

```
<213> ORGANISM: Artificial Sequence
<220> FEATURE:
<223> OTHER INFORMATION: Description of Artificial Sequence: Synthetic
      6xHis tag

<400> SEQUENCE: 23

His His His His His His
1               5
```